United States Patent
Christianson et al.

(10) Patent No.: US 10,118,936 B2
(45) Date of Patent: *Nov. 6, 2018

(54) ARGINASE INHIBITORS AND METHODS OF USE

(71) Applicants: ASTRAZENECA AB, Sodertalje (SE); THE TRUSTEES OF THE UNIVERSITY OF PENNSYLVANIA, Philadelphia, PA (US)

(72) Inventors: David W. Christianson, Media, PA (US); Bruce Edward Tomczuk, Collegeville, PA (US); Richard Scott Pottorf, Belle Mead, NJ (US); Andrew Vargha Colasanti, Scotch Plains, NJ (US); Gary Lee Olson, Mountainside, NJ (US)

(73) Assignees: The Trustees of the University of Pennsylvania, Philadelphia, PA (US); AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,765

(22) Filed: Dec. 4, 2015

(65) Prior Publication Data

US 2016/0194340 A1     Jul. 7, 2016

Related U.S. Application Data

(63) Continuation of application No. 12/693,863, filed on Jan. 26, 2010.

(60) Provisional application No. 61/147,270, filed on Jan. 26, 2009.

(51) Int. Cl.
  *C07F 5/02* (2006.01)
  *A61K 49/00* (2006.01)

(52) U.S. Cl.
  CPC .......... *C07F 5/025* (2013.01); *A61K 49/0002* (2013.01)

(58) Field of Classification Search
  None
  See application file for complete search history.

(56) References Cited

U.S. PATENT DOCUMENTS

| 4,477,391 A | 10/1984 | Collins |
| 4,483,853 A | 11/1984 | Collins et al. |
| 6,723,710 B2 * | 4/2004 | Christianson ........ A61K 31/195 514/64 |

FOREIGN PATENT DOCUMENTS

| WO | 1999/019295 A1 | 4/1999 |
| WO | 20051025620 A1 | 3/2005 |
| WO | WO 2005/025620 | * 3/2005 |
| WO | 20081061612 A1 | 5/2008 |

OTHER PUBLICATIONS

Ito et al. in Cancer Science 94(1), 3-8 (2003).*
Feng et al. in Angewandte Chemie International Edition 46, 3033-3036 (2007).
English translation of Official Action dated Mar. 12, 2014 from copending Japanese Application No. 2011-548216.
Sekiyama et al., "Structure-activity relationships of new agonists and antagonists of different metabotropic glutamate receptor subtypes," British Journal of Pharmacology, 117:1493-1503 (1996).
Jara et al., "Inhibition by analogues of L-tyrosine transport by B16/F10 melanoma cells," Melanoma Research, 1:15-21 (1991).
Khosla et al., "Synthesis of [alpha-methyltyrosine-4]angiotensin II: studies of its conformation, pressor activity, and mode of enzymatic degradation," Proc. Natl. Acad. Sci. USA, 78(2):757-776 (1981).
Goldstein et al., "Oral Sildenafil in the Treatment of Erectile Dysfunction," The New England Journal of Medicine, 338 (20):1397-1404 (1998).
International Search Report for PCT/US201 0/022090, dated Sep. 14, 2010.
Busnel et al., "Synthesis and evaluation of new omega-borono-alpha-amino acids as rat liver arginase inhibitors," Bioorganic & Medicinal Chemistry, 13(7):2373-2379 (2005).
Moali et al., "Recognition of alpha-amino acids bearing various C=NOH functions by nitric oxide synthase and arginase involves very different structural determinants," Biochemistry, 39(28):8208-8218 (2000).
Collet et al., "Synthesis and evaluation of omega-borono-alpha-amino acids as active-site probes of arginase and nitric oxide synthases," J. Chern. Soc., Perkin Trans. 1, 2:177-182 (2000).
Kabasawa et al., "Divergent synthesis of N-hydroxy-l-indospicine, the carbon isostere of N-hydroxy-1-arginine, and N-hydroxy-1-homoarginine from l-glutamate", ARKIVOC (Gainesville, FL, United States), viii:180-187 (2003).

(Continued)

*Primary Examiner* — Dennis Heyer
(74) *Attorney, Agent, or Firm* — Morgan, Lewis & Bockius LLP

(57) ABSTRACT

The present invention is directed to arginase inhibitor compounds of formula IA or formula IB:

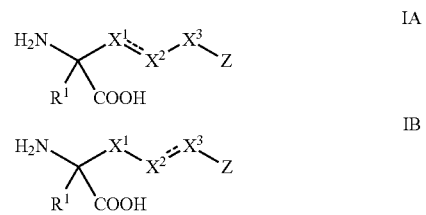

or a pharmaceutically acceptable salt thereof, compositions containing these compounds, and methods of their use for the treatment and diagnosis of conditions characterized by upregulation of arginase, abnormally high arginase activity, or by abnormally low nitric oxide synthase activity.

22 Claims, 24 Drawing Sheets

(56) References Cited

OTHER PUBLICATIONS

Hey et al., "Inhibition of arginase in rat and rabbit alveolar macrophages by Nomega-hydroxy-D,L-indospicine, effects on L-arginine utilization by nitric oxide synthase," British Journal of Pharmacology, 121(3):395-400 (1997).

Reddy et al., "Concise synthesis of omega-borono-alpha-amino acids", Organic & Biomolecular Chemistry, 5(6):889-891 (2007).

Kim et al., "Probing erectile function: S-(2-boronoethyl)-L-cysteine binds to arginase as a transition state analogue and enhances smooth muscle relaxation in human penile corpus cavernosum," Biochemestry, 40(9):2678-2688 (2001).

Cama et al., "Human arginase II: crystal structure and physiological role in male and female sexual arousal," Biochemistry, 42(28):8445-8451 (2003).

Cox et al., "Mechanistic and metabolic inferences from the binding of substrate analogues and products to arginase," Biochemistry, 40(9):2689-2701 (2001).

Cama et al., "Structural and functional importance of first-shell metal ligands in the binuclear manganese cluster of arginase I," Biochemistry, 42(25):7748-7758 (2003).

Cama et al., "Inhibitor coordination interactions in the binuclear manganese cluster of arginase," Biochemistry, 43:8987-8999 (2004).

Baggio et al., "Inhibition of $Mn^{2+}$ 2-arginase by borate leads to the design of a transition state analogue inhibitor, 2(S)-amino-6-boronohexanoic acid," J. Am. Chem. Soc., 119:8107-8108 (1997).

Jew et al., "Highly enantioselective phase-transfer-catalytic alkylation of 2-phenyl-2-oxazoline-4-carboxylic acid tert-butyl ester for the asymmetric synthesis of alpha-alkyl serines," Angew. Chem. Int. Ed., 43(18):2382-2385 (2004).

Lee et al., "Highly Enantioselective Synthesis of (R)-a-Aikylserines via Phase-Transfer Catalytic Alkylation of lo-Biphenyl-2-oxazollne-4-carboxytic Acid tert-Butyl Ester Using Cinchona-Derived Catalysts," American Chemical Society, Organic Letters, 7(8):1557-1560 (2005).

\* cited by examiner

ARGINASE INHIBITORS AND METHODS OF USE

CROSS-REFERENCE TO RELATED APPLICATIONS

This application claims the priority of U.S. 61/147,270 (filed Jan. 26, 2009), the entire contents of which application are incorporated herein by reference.

STATEMENT OF FEDERALLY SPONSORED RESEARCH

This research was supported in part by U.S. Government funds (U.S. National Institutes of Health Contract No. GM49758), and the U.S. Government may therefore have certain rights in the invention.

SUMMARY OF THE INVENTION

The present invention generally relates to enzyme inhibitors, particularly to arginase inhibitors, compositions containing these arginase inhibitors, and methods of their use for the treatment and diagnosis of conditions characterized either by abnormally high arginase activity or by abnormally low nitric oxide synthase activity.

There is a need for inhibitors of arginase activity, which are useful for treating diseases or disorders characterized either by abnormally high arginase activity in a tissue of a mammal or by abnormally low nitric oxide synthase activity in a tissue of the mammal. The methods, compositions, dosage forms, and kits of the present invention are directed toward these, as well as other, important ends.

The present invention, therefore, is directed to inhibitors of arginase activity, which are useful for treating diseases or disorders characterized either by abnormally high arginase activity in a tissue of a mammal or by abnormally low nitric oxide synthase activity in a tissue of the mammal.

Embodiments of the invention provide new inhibitors of arginase, especially α,α-disubstituted α-amino carboxylic acids, particularly L-amino acids. Without wishing to be bound by theory, it is suggested that, of the two substituents at the α-position, one binds to the enzyme active site, and the other α-position sidechain, which is referred to herein as $R^1$, beneficially affects the pharmacological characteristics of the compound. Some exemplary embodiments of chemical structures of some arginase inhibitors of the invention are discussed below.

In one embodiment, the invention is directed to compounds of formula IA or formula IB:

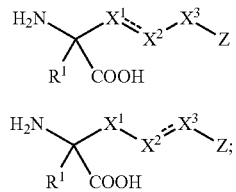

or stereoisomers (especially the L-stereoisomers at the amino acid carbon), lactone prodrugs, or pharmaceutically-acceptable salts thereof;

wherein:
said dashed line represents an optional double bond;
Z is

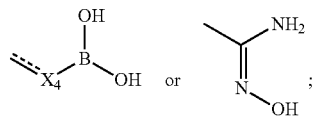

$X^1$ is —(CH$_2$)— or, when said double bond is present between $X^1$ and $X^2$, $X^1$ is —(CH)—;
$X^2$ is —(CH$_2$)— or —(NR$^2$)—, or, when said double bond is present between $X^1$ and $X^2$ or between $X^2$ and $X^3$, $X^2$ is —(CH)— or N;
$X^3$ is —(CH$_2$)—, a heteroatom moiety selected from the group consisting of —S—, —O— and —(NR$^2$)— or, when said double bond is present between $X^2$ and $X^3$ or between $X^3$ and $X^4$, $X^3$ is —(CH)= or N;
$X^4$ is —(CH$_2$)— or, when said double bond is present between $X^3$ and $X^4$, $X^4$ is —(CH)— and is in the trans configuration;
provided that not more than one of $X^2$ and $X^3$ is said —(NR$^2$)— or said heteroatom moiety;
provided that $X^3$ is —(NR$^2$)— when Z is

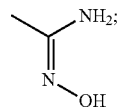

provided that there are no more than two double bonds between $X^1$, $X^2$, $X^3$, and $X^4$ and no two double bonds share a common carbon atom;
$R^1$ is a monovalent moiety other than H; or $R^1$ and said α-carboxylate, when taken together, form a lactone; and
$R^2$ is, independently, H, methyl, or ethyl.

In certain preferred embodiments, the compounds of formula IA and IB are the L-stereoisomer forms (as illustrated below) of the compounds, defined herein as compounds of formula Ia and Ib, respectively:

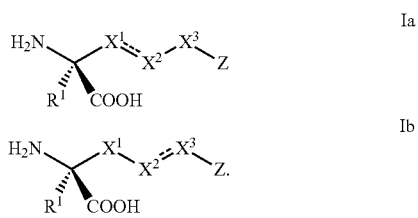

Structural and functional studies conducted by the inventors have established that the "L" stereochemistry of each amino acid (as defined immediately above) is required for tight binding in the enzyme active site; "D" stereoisomers do not bind as tightly or are less efficacious.

In certain embodiments,
$R^1$ is (C$_1$-C$_{20}$)alkyl, hydroxy(C$_1$-C$_{20}$)alkyl, hydroxy(C$_2$-C$_{20}$)alkenyl, (C$_2$-C$_{20}$)alkenyl, (C$_2$-C$_{20}$)alkynyl, (C$_5$-C$_{50}$)aryl, (C$_3$-C$_{50}$)heteroaryl having at least one heteroatom selected from N, O, and S; (C$_5$-C$_{50}$)aryl(C$_1$-C$_{20}$)alkyl, (C$_3$-C$_{50}$)heteroaryl(C$_1$-C$_{20}$)alkyl, (C$_2$-C$_{50}$)heterocycloalkyl(C$_1$-C$_{50}$)alkyl, (C$_5$-C$_{50}$)aryloxy(C$_1$-C$_{20}$)alkyl, (C$_5$-C$_{50}$)arylthio ($C_1$-$C_{50}$)alkyl, ($C_3$-$C_{50}$)heteroaryloxy($C_1$-$C_{20}$)alkyl, ($C_5$-$C_{50}$)arylamino($C_1$-$C_{20}$)alkyl, ($C_3$-$C_{50}$)heteroarylamino($C_1$-$C_{20}$)alkyl, amino($C_1$-$C_{20}$)alkyl, —$R^x$—C(=O)—$R^y$, —$R^x$—O—$R^z$, —$R^x$—O—$R^x$—$NR^3R^5$, —$R^x$—$NR^3R^5$, —$R^x$—O—C(=O)—$R^y$, ($C_1$-$C_6$)alkyl-B—(OH)$_2$, -L-Y, or labeled derivative thereof; or $R^1$ and said α-carboxylate, when taken together, form a lactone having 4 to 7 ring atoms;

each $R^x$ is independently ($C_1$-$C_{20}$)alkylenyl;

$R^y$ is ($C_1$-$C_6$)alkyl, ($C_5$-$C_{50}$)aryl($C_1$-$C_6$)alkyl, ($C_5$-$C_{50}$)aryloxy($C_1$-$C_6$)alkyl, hydroxyl, ($C_1$-$C_6$)alkoxy, ($C_3$-$C_5$)cycloalkyl, $N(R^3)_2$, ($C_5$-$C_{50}$)aryl, ($C_3$-$C_{50}$)heteroaryl having at least one heteroatom selected from N, O, and S; heterocyclyl, ($C_5$-$C_{50}$)aryl($C_1$-$C_6$)alkyl, or ($C_3$-$C_{50}$)heteroaryl($C_1$-$C_6$)alkyl;

$R^z$ is ($C_1$-$C_6$)alkyl, ($C_3$-$C_5$)cycloalkyl, —$R^x$—O—($C_1$-$C_6$)alkyl, ($C_5$-$C_{50}$)aryl, ($C_3$-$C_{50}$)heteroaryl having at least one heteroatom selected from N, O, and S; ($C_5$-$C_{50}$)aryl($C_1$-$C_6$)alkyl, or ($C_3$-$C_{50}$)heteroaryl($C_1$-$C_6$)alkyl;

$R^3$ is, independently, H, ($C_1$-$C_6$)alkyl, or ($C_1$-$C_6$)alkyl-N($R^4$)$_2$;

$R^4$ is, independently, H or ($C_1$-$C_6$)alkyl;

$R^5$ is —C(=O)—($C_1$-$C_6$)alkyl, —C(=O)—($C_5$-$C_{50}$)aryl, —$SO_2$—($C_5$-$C_{50}$)aryl, —C(=O)$NR^3R^4$, —C(=O)—$NR^4$($C_5$-$C_{50}$)aryl, or —C(=O)-heterocycle;

or $R^3$ and $R^5$ together form a ($C_2$-$C_{10}$)heterocycloalkyl;

L is an aliphatic or aromatic linkage; and

Y is a residue of an imageable moiety, peptide, peptidomimetic, or carbohydrate.

In other embodiments, the invention is directed to compositions, comprising:

at least one compound of the invention or a pharmaceutically acceptable salt thereof; and a pharmaceutically-acceptable carrier.

In yet other embodiments, the invention is directed to methods of inhibiting arginase in a mammal, comprising the step of:

administering to said mammal an effective amount of a compound of the invention or a pharmaceutically acceptable salt thereof.

In yet other embodiments, the invention is directed to methods of treating an arginase-related disorder in a mammal, comprising the step of:

administering to said mammal an effective amount of a compound of the invention or a pharmaceutically acceptable salt thereof.

In other embodiments, the invention is directed to methods of diagnosing arginase overexpression in a patient, comprising the step of:

administering to said patient a diagnostically-effective amount of a compound of the invention or a pharmaceutically acceptable salt thereof;

where $R^1$ is a labeled derivative thereof; and imaging said patient.

In other aspects, the invention is directed to methods of diagnosing arginase overexpression in a patient, comprising the step of:

administering to said patient a diagnostically-effective amount of a compound of the invention or a pharmaceutically acceptable salt thereof;

where Y is an imageable moiety; and imaging said patient.

In certain aspects, the invention is directed to methods for radioimaging a patient, comprising the steps of:

administering to said patient an effective amount of a compound of the invention;

wherein Y is an imageable moiety; and scanning said patient using a radioimaging device.

In certain aspects, the invention is directed to methods of inhibiting arginase, comprising the step of:

contacting said arginase with a compound of the invention or a salt thereof. In certain embodiments, the arginase is a yeast, bacterial, parasitic, or mammalian arginase. In certain other embodiments, the mammalian arginase is human type I arginase or human type II arginase (e.g., human penile arginase).

In certain aspects, the invention is directed to diagnostic compositions, comprising:

a diagnostically-effective amount of the compound of the invention or a pharmaceutically acceptable salt thereof; and a pharmaceutically acceptable carrier;

where $R^1$ is a labeled derivative thereof.

In certain aspects, the invention is directed to diagnostic compositions, comprising: a diagnostically-effective amount of the compound of the invention or a pharmaceutically acceptable salt thereof; and a pharmaceutically acceptable carrier;

where Y is an imageable moiety.

In certain embodiments, the invention is directed to methods of treating a disease or condition associated with up-regulation of arginase in a mammal, comprising the step of:

administering to said mammal an effective amount of a compound of the invention or a pharmaceutically acceptable salt thereof;

wherein said disease or condition is a gastrointestinal disease, a pulmonary inflammatory disease, a sexual arousal disorder, a cardiovascular disorder, a hemolytic disorder, an autoimmune disease, wound healing, a disease caused by parasitic protozoa, a disease caused by bacteria, a cancer, pre-term labor, psoriasis, or a combination thereof.

In certain embodiments, the invention is directed to methods of providing relief from immune suppression in a mammal, comprising the step of:

administering to said mammal an effective amount of a compound of the invention or a pharmaceutically acceptable salt thereof;

wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

In certain embodiments, the invention is directed to methods of inhibiting the production of ornithine in a mammal suffering from at least one tumor, comprising the step of:

administering to said mammal an effective amount of a compound of the invention or a pharmaceutically acceptable salt thereof.

In certain embodiments, the invention is directed to compositions, comprising:

a compound of formula Ia or formula Ib or a pharmaceutically acceptable salt thereof;

a phosphodiesterase-1 (PDE1) inhibitor, a phosphodiesterase-2 (PDE2) inhibitor, a phosphodiesterase-5 (PDE5) inhibitor, or a non-specific PDE inhibitor that inhibits PDE1, PDE2, PDE5, or a combination thereof; and optional pharmaceutically-acceptable excipient.

Synthesis of α,α-disubstituted amino acids is well known to be difficult, at least in part because the α-nitrogen atom can act as a nucleophile and therefore interfere with alkylation of the α-carbon atom. In order to temporarily mask this functionality, the nitrogen atom is protected with diphenylmethylene group, which does not interfere with the subsequent alkylation and, in some cases, hydroboration. Accordingly, in certain embodiments, the invention is directed to processes for preparing a substituted boronic acid of formula I:

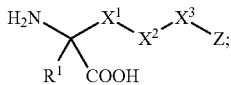

or stereoisomer, lactone prodrug, or pharmaceutically-acceptable salt thereof;
said process comprising:
reacting in a solution phase, in the presence of a iridium catalyst, preferably [Ir(cod)Cl]$_2$, 4,4,5,5-tetramethyl-1,3,2-dioxaborolane with a compound of formula II:

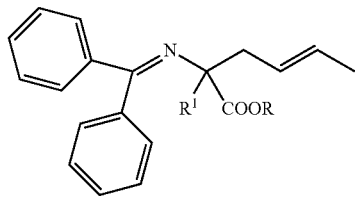

to form a boronate ester product; and
deprotecting said boronate ester product, preferably with a strong aqueous acid, to form said compound of formula I;
wherein:
R is methyl, ethyl, or t-butyl;
Z is

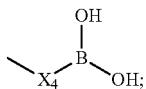

$X^1$ is —(CH$_2$)—;
$X^2$ is —(CH$_2$)—;
$X^3$ is —(CH$_2$)—;
$X^4$ is —(CH$_2$)—;
$R^1$ is a monovalent moiety other than H; or $R^1$ and said α-carboxylate, when taken together, form a lactone.

DETAILED DESCRIPTION OF THE INVENTION

Figure 1:
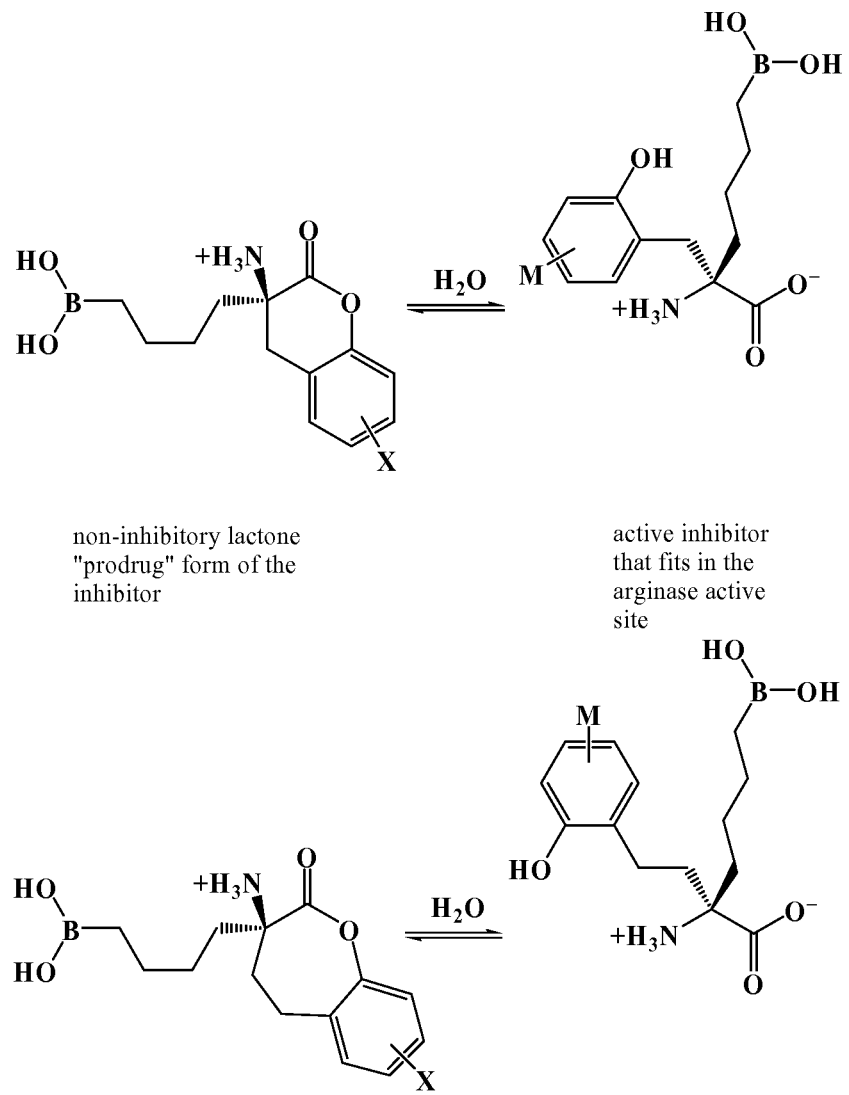
FIGS. 1 and 2 illustrate some exemplary arginase inhibitors in prodrug form according to certain exemplary embodiments hereof.

Embodiments of the present invention relates to enzyme inhibitors, particularly to arginase inhibitors, compositions thereof, and methods of their use for the treatment and diagnosis of conditions characterized either by abnormally high arginase activity or by abnormally low nitric oxide synthase activity.

Definitions

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations of 20%, preferably +10%, more preferably +5%, even more preferably +1%, and yet even more preferably +0.1% from the specified value, as such variations are appropriate to perform the disclosed methods and compositions.

As used herein, "administering" refers to the act of giving or providing a composition or compound to a patient by the patient themselves or by a caregiver, such as a medical professional or the like, including the act of ingestion by or application to the patient or the like wherein the composition or compound can exert its effects.

As used herein, "effective amount" refers to an amount of the active ingredient as described herein that may be effective to prevent, reduce or eliminate the symptoms or condition.

As used herein, "treating" and "treatment" refer to the preventative, curative, and palliative treatment of a condition malady or affliction, especially in a human patient in need of such treatment.

As used herein, "pharmaceutically-acceptable" refers to those compounds, materials, compositions, or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically-acceptable salts" refer to derivatives of the disclosed compounds wherein the parent compound is modified by making acid or base salts thereof, including acid addition salts and base addition salts. Examples of pharmaceutically-acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, glycerophosphoric, hemisulfanic, heptanoic, hexanoic, hydrochloric, hydrobromic, hydroiodic, 2-hydroxyethanesulfonic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like. Thus, the term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. The pharmaceutically-acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperizine, pyrrolidine, ethanolamine, morpholine, diazapine, ethylene diamine, pyridine, quinoline, quinuclidine, and the like.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "patient" refers to an animal, including a mammal, preferably a human.

$R^a$, as used herein, is, independently, H, OH, alkyl (optionally substituted with one or more $R^4$), alkoxy (optionally substituted with one or more $R^4$), halo, trifluoromethyl, alkanoyloxy (optionally substituted with one or more $R^4$), methylenedioxy, benzyloxy (optionally substituted with one or more $R^4$), phenyloxy (optionally substituted with one or more $R^4$), naphthyloxy (optionally substituted with one or more $R^4$), nitro, trifluoromethoxy, nitrile, alkenyl (optionally substituted with one or more $R^4$), alkynyl, sulfoxide, sulfonyl, sulfonamido, aryl (optionally substituted with one or more $R^4$), heteroaryl (optionally substituted with one or more $R^4$), aryloyl (optionally substituted with one or more $R^4$), heteroaryloyl (optionally substituted with one or more $R^4$), heteroaryloxy (optionally substituted with one or more $R^4$), heteroarylmethyloxy (optionally substituted with one or more $R^4$), alkanoyl, alkoxycarbonyl, alkylaminocarbonyl, or amino. $R^4$ is $(C_1-C_{20})$alkyl, $(C_2-C_{20})$alkenyl, $(C_2-C_{20})$alkynyl, halo, nitrile, nitro, $(C_5-C_{50})$aryl, $(C_3-C_{50})$heteroaryl having at least one heteroatom selected from N, O, and S; $(C_5-C_{50})$aryl$(C_1-C_{20})$alkyl, heteroaryl$(C_1-C_{20})$alkyl, $(C_5-C_{50})$aryloxy$(C_1-C_{20})$alkyl, heteroaryloxy$(C_1-C_{20})$alkyl, $(C_5-C_{50})$arylamino$(C_1-C_{20})$alkyl, heteroarylamino$(C_1-C_{20})$alkyl, amino$(C_1-C_{20})$alkyl, —$R^x$—C(=O)—$R^y$, or —$R^x$—O—$R^z$, -L-Y.

"Alkyl," as used herein, refers to an aliphatic hydrocarbon chain of 1 to about 20 carbon atoms, preferably 1 to 10 carbon atoms, more preferably, 1 to 6 carbon atoms, and even more preferably, 1 to 4 carbon atoms and includes straight and branched chains such as methyl, ethyl, n-propyl, isopropyl, n-butyl, isobutyl, sec-butyl, tert-butyl, n-pentyl, isopentyl, neo-pentyl, n-hexyl, and isohexyl. Lower alkyl refers to alkyl having 1 to 4 carbon atoms. Alkyl groups can be optionally substituted with one or more $R^a$, as defined herein.

"Alkylenyl," as used herein, refers to a divalent counterpart of "alkyl," as defined herein (e.g., methyleneyl, ethyleneyl, propyleneyl, etc.). Alkylenyl groups can be optionally substituted with one or more $R^a$, as defined herein.

"Alkenyl" or "olefinic," as used herein, refers to an alkyl group of at least two carbon atoms having one or more double bonds, wherein alkyl is as defined herein. Alkenyl groups can be optionally substituted with one or more $R^a$, as defined herein.

"Hydroxy$(C_1-C_{20})$alkyl," as used herein, refers to an alkyl group, as defined herein, substituted with at least one hydroxy group.

"Hydroxy$(C_2-C_{20})$alkenyl," as used herein, refers to an alkenyl group, as defined herein, substituted with at least one hydroxy group.

"Alkynyl," as used herein, refers to an alkyl group of at least two carbon atoms having one or more triple bonds, wherein alkyl is as defined herein. Alkynyl groups can be optionally substituted with one or more $R^a$, as defined herein.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. Aryl groups can be optionally substituted with one or more $R^a$, as defined herein.

"Heteroaryl," as used herein, refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups can be optionally substituted with one or with one or more $R^a$, as defined herein.

"$(C_5-C_{50})$Aryl$(C_1-C_{20})$alkyl," as used herein, refers to the group R—R'— where R is an aryl group and R' is an alkylenyl, as defined herein.

"Heteroaryl$(C_1-C_{20})$alkyl," as used herein, refers to the group R—R'— where R is a heteroaryl group and R' is an alkylenyl, as defined herein.

"($C_5$-$C_{50}$)aryloxy($C_1$-$C_{20}$)alkyl," as used herein, refers to the group R—O—R'— where R is an aryl group and R' is an alkylenyl, as defined herein.

"Heteroaryloxy($C_1$-$C_{20}$)alkyl," as used herein, refers to the group R—O—R'— where R is a heteroaryl group and R' is an alkylenyl, as defined herein.

"($C_5$-$C_{50}$)arylamino($C_1$-$C_{20}$)alkyl," as used herein, refers to the group R—NH—R'— where R is an aryl group and R' is an alkylenyl, as defined herein.

"Heteroaryloxyamino($C_1$-$C_{20}$)alkyl," as used herein, refers to the group R—NH—R'— where R is a heteroaryl group and R' is an alkylenyl, as defined herein.

"Amino($C_1$-$C_{20}$)alkyl," as used herein, refers to the group N(R")—R'— where R" is a hydrogen or ($C_1$-$C_6$)alkyl group and R' is an alkylenyl, as defined herein.

"Cycloalkyl," as used herein, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

"Heterocycloalkyl," as used herein, refers to an optionally substituted, cycloalkyl group having one or more rings in their structures having from 2 to about 20 carbon atoms (and all combinations and subcombinations of ranges and specific numbers of carbon atoms therein), with from 2 to about 10 carbon atoms being preferred, in addition to at least one heteroatom independently selected from the group consisting of N, O and S. Multi-ring structures may be bridged or fused ring structures. Groups include, but are not limited to, aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl.

"Halo" or "halogen," as used herein, refers to chloro, bromo, fluoro, and iodo.

"Alkoxy," as used herein, refers to the group R—O— where R is an alkyl group of 1 to 6 carbon atoms.

"Alkoxycarbonyl," as used herein, refers to the group R—O—C(=O)— where R is an alkyl group of 1 to 6 carbon atoms.

"Alkanoyl," as used herein, refers to the group R—C(=O)— where R is an alkyl group of 1 to 6 carbon atoms.

"Alkanoyloxy," as used herein, refers to the group R—C(=O)—O— where R is an alkyl group of 1 to 6 carbon atoms.

"Alkylaminocarbonyl," as used herein, refers to the group R—NH—C(=O)— where R is an alkyl group of 1 to 6 carbon atoms.

"Alkylcarbonylamino," as used herein, refers to the group R—C(=O)—NH where R is an alkyl group of 1 to 6 carbon atoms.

"Heteroarylmethyl," as used herein, refers to the group R—$CH_2$— where R is a heteroaryl group, as defined herein.

"Heteroarylmethyloxy," as used herein, refers to the group R—$CH_2$—O— where R is a heteroaryl group, as defined herein.

"Heteroaryloxy," as used herein, refers to the group R—O— where R is a heteroaryl group, as defined herein.

"Heteroarylmethyloxy," as used herein, refers to the group R—$CH_2$—O— where R is a heteroaryl group, as defined herein.

"Heterocycle" or "heterocyclyl," as used herein, refers to a stable 5- to 7-membered monocyclic or bicyclic or 7- to 10-membered bicyclic heterocyclic ring, or radical thereof, that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2 dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2 dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Sulfoxide," as used herein, refers to a compound or moiety containing the group —S(=O)—.

"Sulfonamido," as used herein, refers to a moiety containing the group —S(O)$_2$—NH—.

"Sulfonyl," as used herein, refers to a moiety containing the group —S(O)$_2$—.

"Aliphatic linkage," as used herein, refers to any divalent alkylenyl group (e.g., methyleneyl, ethyleneyl, propyleneyl, etc.), including groups having the general formula —(CH$_2$)$_m$—, wherein m is an integer from 1 to 6.

"Aromatic linkage," as used herein, refers to any divalent aryl group, such as a —(C$_4$H$_4$)— group.

"Residue of an imageable moiety," or simply "imageable moiety," as used herein, refers to any moiety, as generally known in the art and as specifically defined herein, that comprises one or more groups capable of detection either directly or indirectly in an in vivo or in vitro diagnostic imaging procedure, and comprises, e.g., one or more moieties that emit or may be caused to emit detectable radiation (e.g., by radioactive decay, fluorescence excitation, spin resonance excitation, etc.), groups that affect local electromagnetic fields (e.g., paramagnetic, superparamagnetic, ferromagnetic, or ferromagnetic species), groups that absorb or scatter radiation energy (e.g., chromophores, particles (including gas or liquid containing vesicles), heavy elements and compounds thereof, etc.), and groups that generate a detectable substance (e.g., gas microbubble generators). Examples of imageable moieties may be selected from the group consisting of a gamma ray emitting radioisotopes, positron emitting radioisotopes, a magnetic resonance imaging contrast agents (e.g., gadolinium chelates), X-ray contrast agents (e.g., iodinated radioopaque aromatic compounds), or an ultrasound contrast agent (e.g., liposomes comprising an echogenic compound).

"Peptide," as used herein, means a linear compound that consists of two or more amino acids (as defined herein) that are linked by means of a peptide bond. A "peptide" as used in the presently claimed invention is intended to refer to a moiety with a molecular weight of less than about 10,000 Daltons, preferable less than about 5,000 Daltons, and more preferably less than about 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog." A "residue of peptide" means that a molecule where a portion of a peptide has been removed to accommodate a bond to another molecule, such as in the R$^1$ group of the compounds of the invention.

"Pseudopeptide" or "peptidomimetic," as used herein, means a compound that mimics the structure of an amino acid residue or a peptide, for example, by using linking groups other than amide linkages between the peptide mimetic and an amino acid residue (pseudopeptide bonds) or by using non-amino acid substituents or a modified amino acid residue. A "residue of peptidomimetic" means that a molecule where a portion of a pseudopeptide or peptidomimetic has been removed to accommodate a bond to another molecule, such as in the R$^1$ group of the compounds of the invention.

"Carbohydrate," as used herein, means an organic compound having aldehydes or ketones with many hydroxyl groups added, usually one on each carbon atom that is not part of the aldehyde or ketone functional group, including sugars, starches, celluloses, and gums. A "residue of carbohydrate" means that a molecule where a portion of a carbohydrate has been removed to accommodate a bond to another molecule, such as in the R$^1$ group of the compounds of the invention.

Biological Activity of Arginase

Each individual excretes roughly ten kilograms of urea per year, as a result of the hydrolysis of arginine in the final cytosolic step of the urea cycle. The activity of the liver enzyme, arginase, permits disposal of nitrogenous wastes that result from protein catabolism. In tissues lacking a complete complement of the enzymes that catalyze the reactions of the urea cycle, arginase regulates cellular concentrations of arginine and ornithine, which are used for biosynthetic reactions. Arginine is used, by way of example, in the synthesis of nitric oxide. In macrophages, arginase activity is reciprocally coordinated with the activity of the enzyme, nitric oxide synthase. Reciprocal coordination of the activities of arginase and nitric oxide synthase (NOS) modulates NO-dependent cytotoxicity.

Arginase catalyzes divalent cation-dependent hydrolysis of L-arginine to form L-ornithine and urea. The enzyme is currently known to serve three important functions: (1) production of urea, (2) production of ornithine, and (3) regulation of substrate arginine levels for nitric oxide synthase. Urea production provides a mechanism to excrete nitrogen in the form of a highly soluble, non-toxic compound, thus avoiding the potentially dangerous consequences of high ammonia levels. L-Ornithine is a precursor for the biosynthesis of polyamines, spermine, and spermidine, which have important roles in cell proliferation and differentiation. Finally, arginase modulates production of nitric oxide by regulating the levels of arginine present within tissues.

Synthesis and evaluation of non-reactive arginine analogs for use as enzyme inhibitors or receptor antagonists is a rapidly growing area of medicinal chemical research. Since both NO synthase and arginase compete for the same substrate, the possibility of reciprocal regulation of both arginine metabolic pathways has been explored. Furthermore, N-hydroxy-L-arginine (L-HO-Arg), an intermediate in the NO synthase reaction, is an endogenous arginase inhibitor. The phenomenon of reciprocal regulation between arginase and NO synthase has only recently been examined. In the internal anal sphincter (IAS), it was shown that exogenous administration of arginase attenuates NO synthase-mediated non-adrenergic and non-cholinergic (NANC) nerve-mediated relaxation.

As discussed in more detail below, an excess of arginase has also recently been associated with a number of pathological conditions that include gastric cancer, certain forms of liver injury, and pulmonary hypertension following orthotopic liver transplantation. Furthermore, high levels of arginase can cause impairment in NANC-mediated relaxation of the IAS. Previous studies have demonstrated that arginase pre-treatment causes significant suppression of the NANC nerve-mediated relaxation of the IAS that is mediated primarily via the L-arginine-NO synthase pathway. Impairment in NANC relaxation by excess arginase may be related to L-arginine depletion. Furthermore, suppressed relaxation could be restored by the arginase inhibitor L-HO-Arg. It is possible, therefore, that patients with certain conditions associated with an increase in arginase activity may stand to benefit from treatment with arginase inhibitors. However, an arginase inhibitor such as L-OH-Arg can not be selective since it also serves as a NO synthase substrate. Because of this, the exact role of arginase in pathophysiology and the potential therapeutic actions of arginase inhibitors remains undetermined.

The X-ray crystal structure of rat liver arginase is available. Rat liver arginase is a trimeric metalloenzyme which contains a bi-nuclear manganese cluster in the active site of each subunit. This bi-nuclear cluster is required for maximal catalytic activity. X-ray crystal structures of human arginase I and human arginase II are also available. See, e.g., Di Costanzo et al., Proc. Natl. Acad. Sci. (USA) 102, 13058 (2005) (X-ray crystal structures of human arginase I); and Cama et al., Biochemistry 42, 8445 (2003) (X-ray crystal structures of human arginase II). Similarly, several structural analyses and modeling studies have been performed using three-dimensional crystal structures of arginase-inhibitor complexes, including the inhibitors illustrated in FIG. 18. See, e.g., Cox et al., Nat. Struct. Biol. 6, 1043 (1999) (rat arginase I complexed with 2(S)-amino-6-borono-hexanoic acid ("ABH")); Kim et al., Biochemistry 40, 2678 (2001) (rat arginase I complexed with S-(2-boronoethyl)-1-cysteine ("BEC")); Cox et al., Biochemistry 40, 2689 (2001) (rat arginase I complexed with N$^\omega$-hydroxy-nor-1-arginine ("nor-NOHA")); DiConstanzo et al., Proc. Natl. Acad. Sci. (USA) 102, 13058 (2005) (human arginase I complexed with ABH and BEC); and Cama et al., Biochemistry 42, 8445 (2003) (human arginase II complexed with BEC).

Arginase Inhibitors

Figure 18:
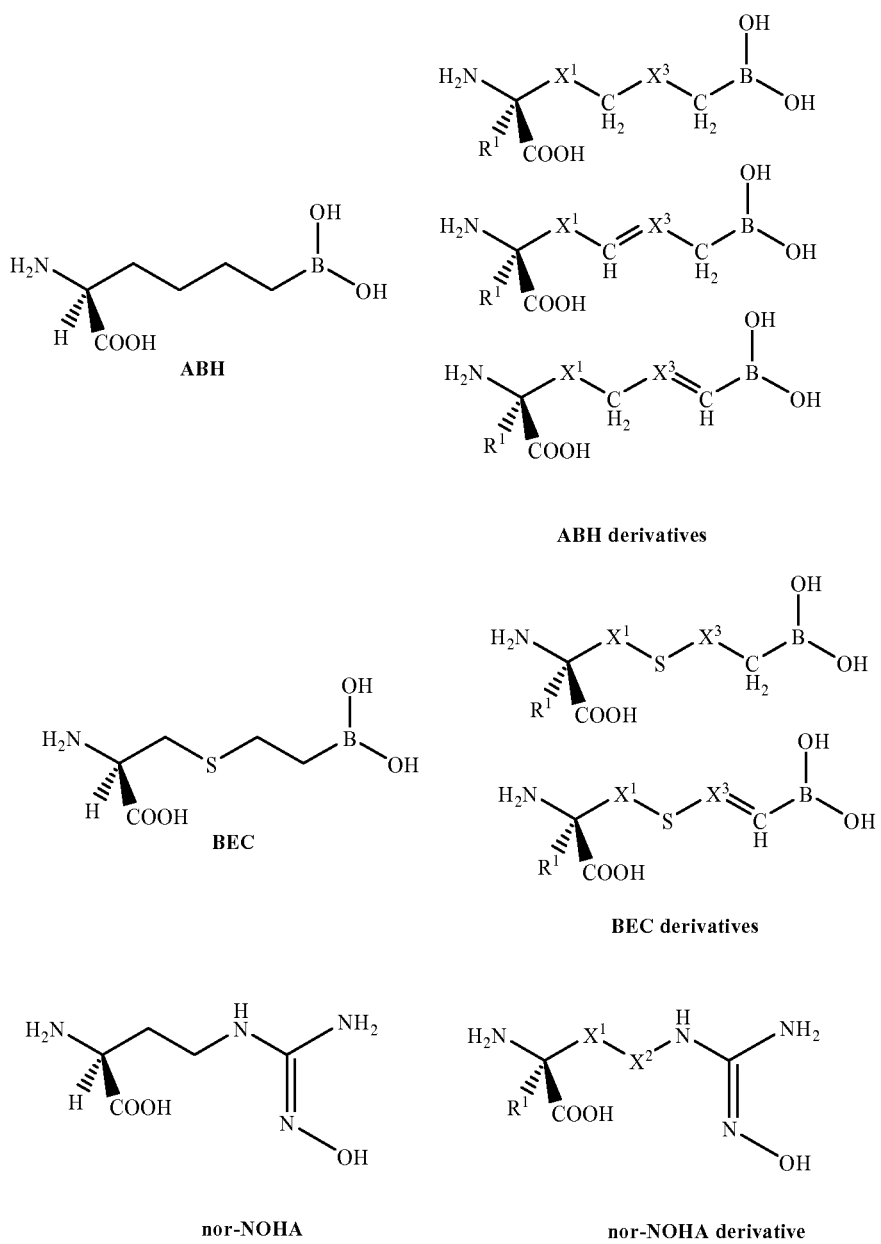
FIG. 18 illustrates some known arginase inhibitors and several improved analogs thereof in accordance with certain embodiments of the invention.
Figure 19:
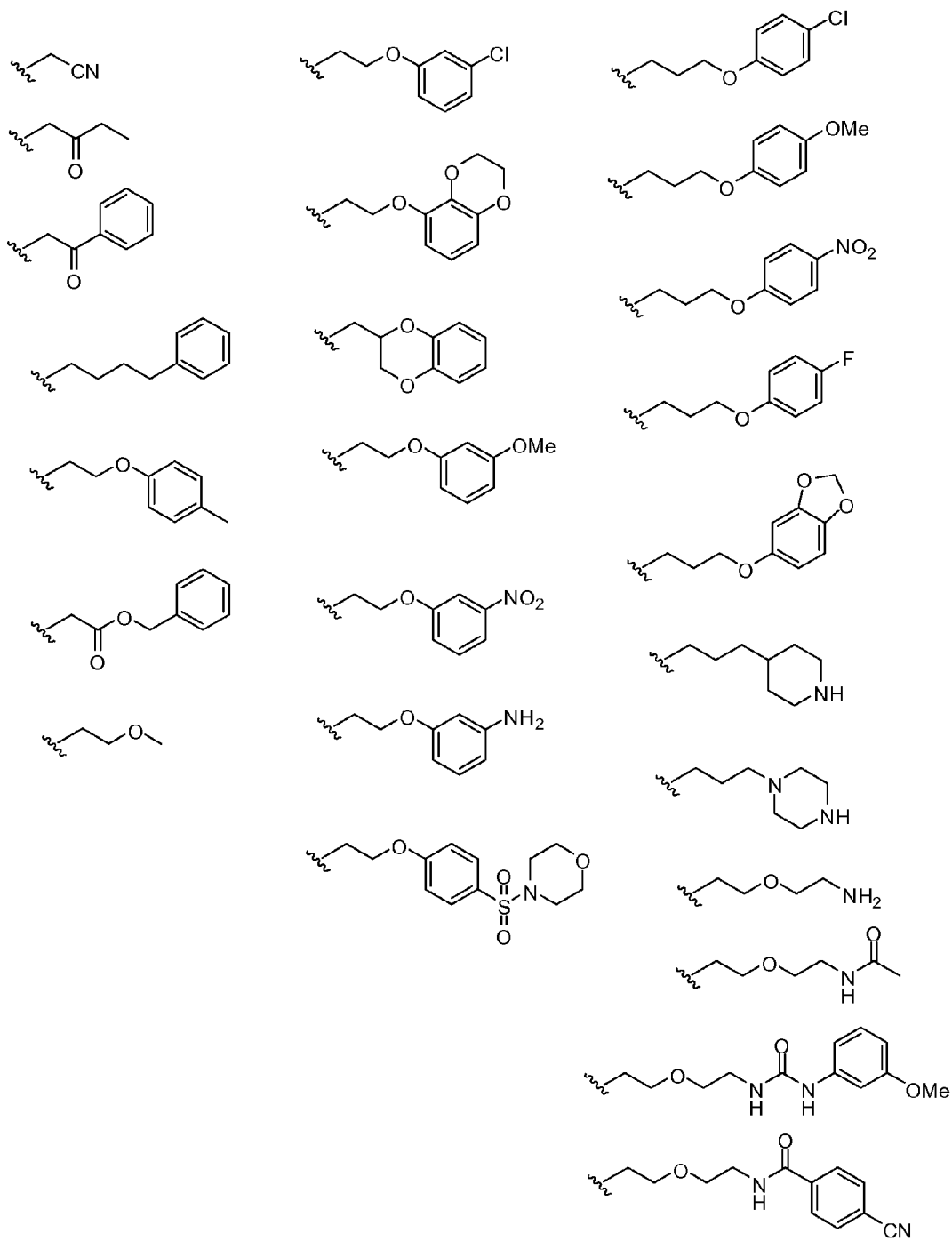
FIGS. 19 through 24 illustrate some exemplary $R^1$ sidechains according to certain embodiments of the present invention.
Figure 20:
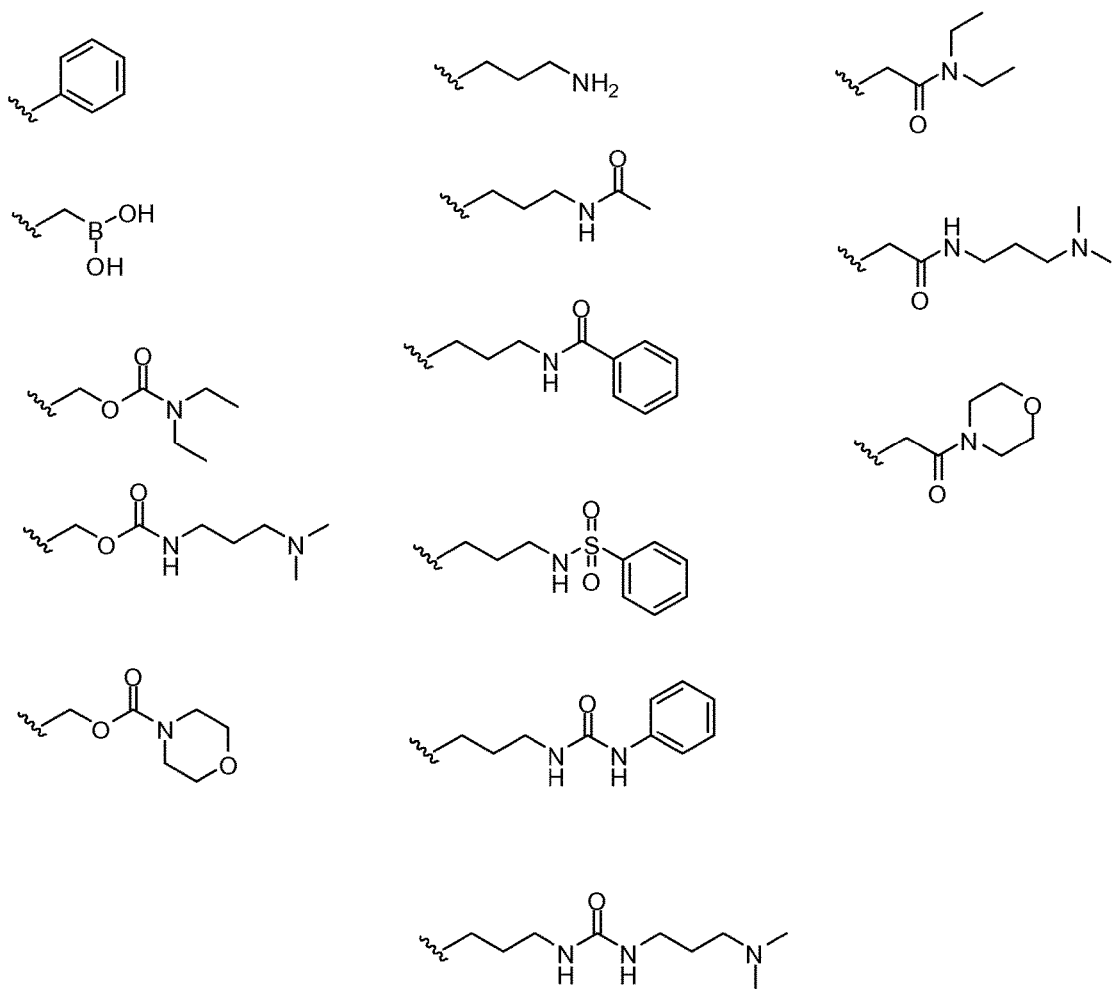
Figure 21:
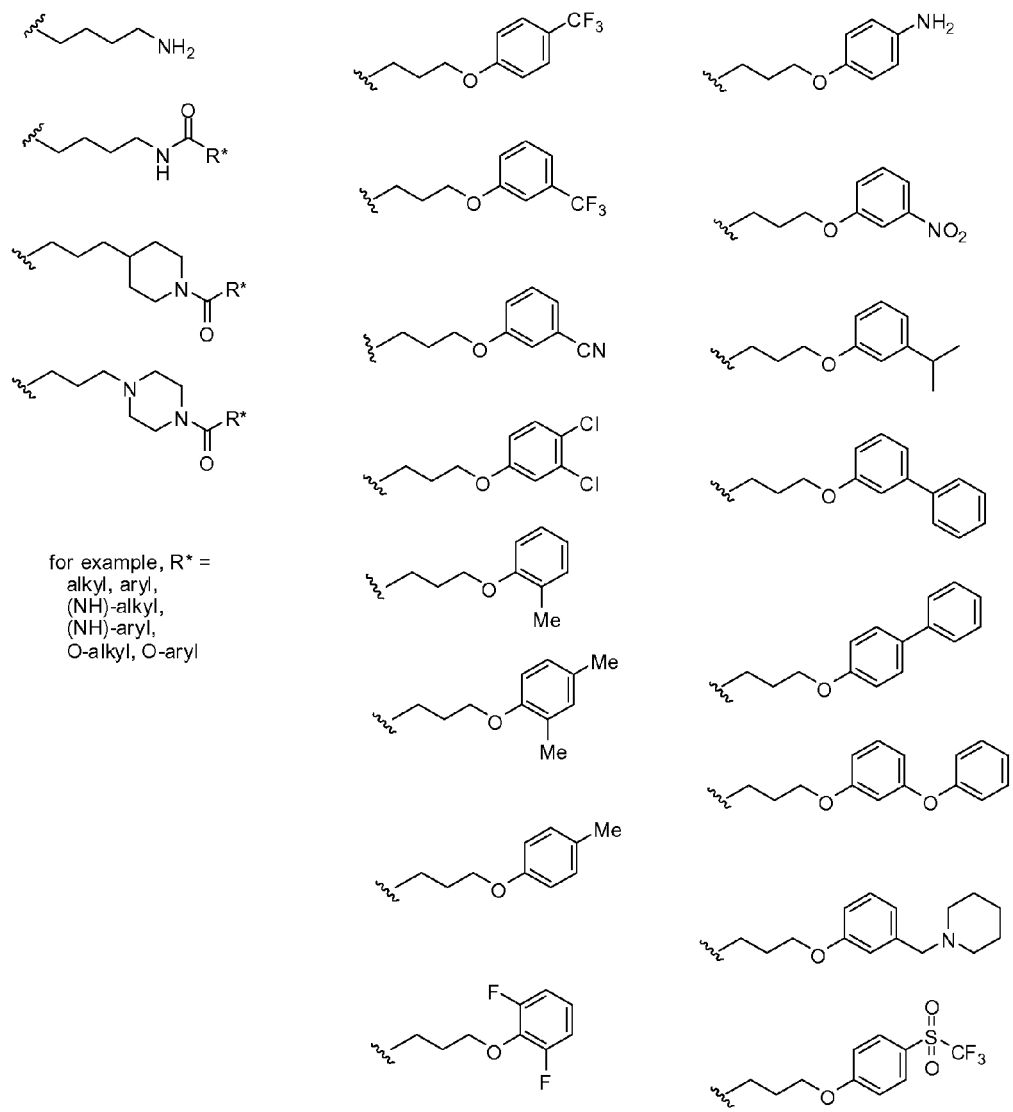
Figure 22:
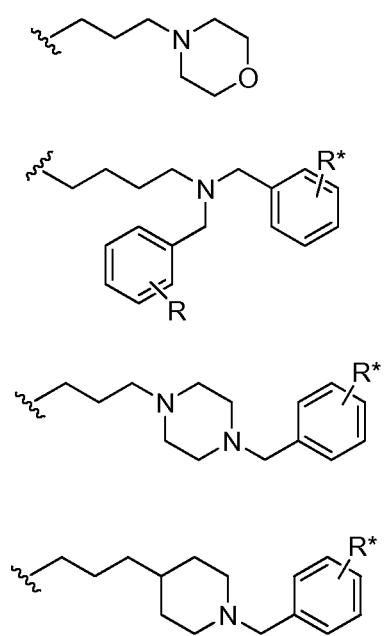
Figure 23:
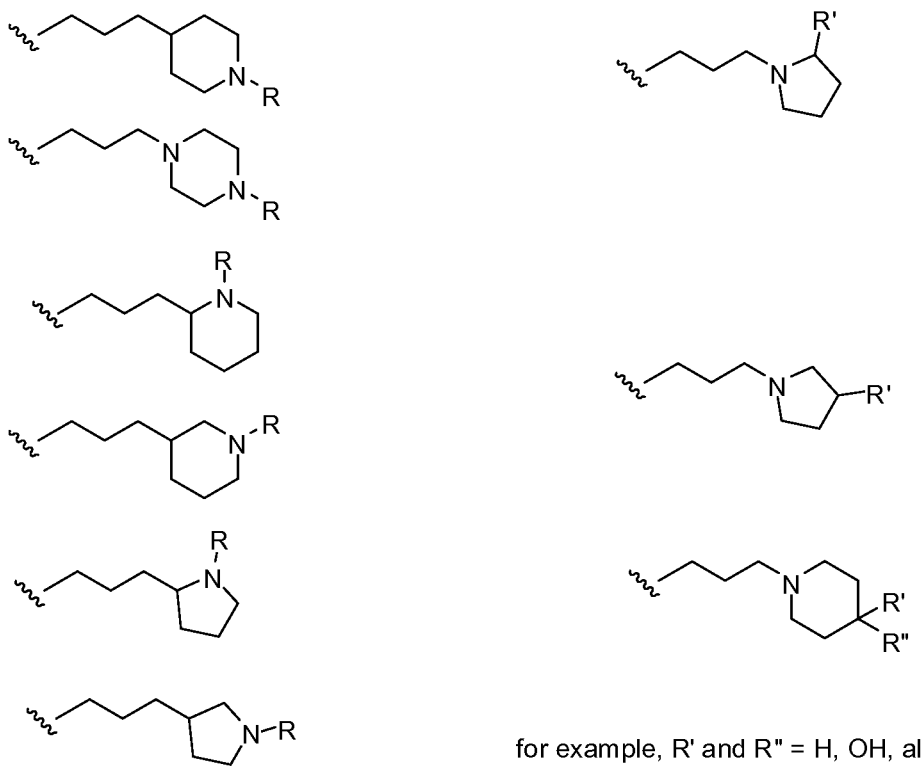
Figure 24:
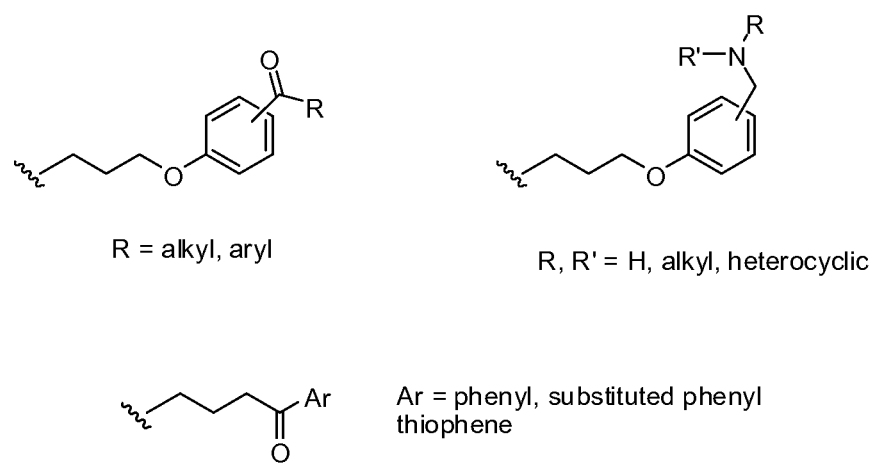

In view of the foregoing modeling studies and based on the discoveries described herein, new α-amino acid arginase inhibitors that are modified at the Cα position, thereby generating heretofore unknown molecular entities that bind to arginase I and arginase II, including human arginases, are provided herein. The Cα-R$^1$ groups of the invention replace the Cα-H groups of the parent compounds, namely ABH, BEC, and nor-NOHA, which are illustrated in FIG. 18. It should be appreciated that the addition of the R$^1$ groups can be selected to target binding interactions in the outer active site cleft and the region flanking the outer active site clefts of parasitic arginase, bacterial arginase, and arginases I and II. Without intending to be bound by theory, the inventors suggest that these R$^1$-substituted compounds have increased interactions with the target protein(s) that result in increased potencies or selectivities (or both) over compounds in the prior art.

Embodiments of the present invention therefore is directed, in part, to compounds of formula IA or formula IB:

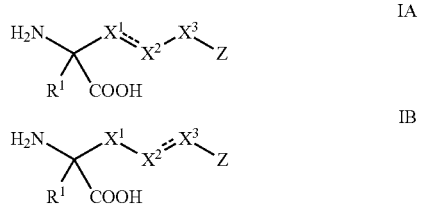

or stereoisomers (especially the L stereoisomers of the amino acid), lactone prodrugs, or pharmaceutically-acceptable salts thereof;
wherein:
said dashed line represents an optional double bond;
Z is

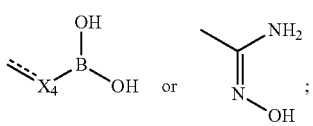

X$^1$ is —(CH$_2$)— or, when said double bond is present between X$^1$ and X$^2$, X$^1$ is —(CH)—;

X$^2$ is —(CH$_2$)— or —(NR$^2$)—, or, when said double bond is present between X$^1$ and X$^2$ or between X$^2$ and X$^3$, X$^2$ is —(CH)— or N;

X$^3$ is —(CH$_2$)—, a heteroatom moiety selected from the group consisting of —S—, —O— and —(NR$^2$)— or, when said double bond is present between X$^2$ and X$^3$ or between X$^3$ and X$^4$, X$^3$ is —(CH)— or N;

X$^4$ is —(CH$_2$)— or, when said double bond is present between X$^3$ and X$^4$, X$^4$ is —(CH)— and is in the trans configuration;
provided that not more than one of X$^2$ and X$^3$ is said —(NR$^2$)— or said heteroatom moiety;
provided that X$^3$ is —(NR$^2$)— when Z is

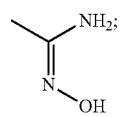

provided that there are no more than two double bonds between X$^1$, X$^2$, X$^3$, and X$^4$ and no two double bonds share a common carbon atom;

R$^1$ is a monovalent moiety other than H; or R$^1$ and said α-carboxylate, when taken together, form a lactone; and R$^2$ is, independently, H, methyl, or ethyl.

Some examples of suitable R$^1$ groups are presented in FIGS. 19-24 in the attached drawings.

In certain preferred embodiments, the compounds of formula IA and IB are referred to herein as the "L-stereoisomer" forms (as illustrated below) of the compounds, defined herein as compounds of formula Ia and Ib, respectively. Compounds corresponding to the so-called "D-stereoisomers" would have the opposite stereochemical condition at the α-carbon in these figures:

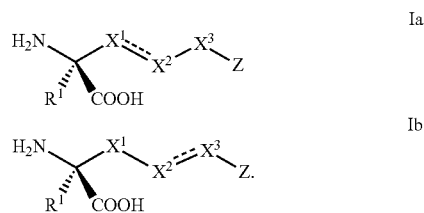

Structural and functional studies conducted by the inventors have established that the "L" stereochemistry of each amino acid (as defined immediately above) is required for tight binding in the enzyme active site; "D" stereoisomers do not bind as tightly or are less efficacious. Alternatively stated, the preferred stereochemistry is analogous to the stereospecific replacement of the (R)-hydrogen in ABH (see FIG. 18) by R$^1$. Of course, depending on the relative priority of the two substituents at the quaternary Cα, the compound could have either R- or S-stereochemistry. In preferred compounds, the S-stereochemistry generally occurs only in a limited case, typically when R$^1$ is a lower priority group, such as methyl, ethyl, propyl, and n-butyl. For groups that are generally larger than n-butyl, the stereochemistry is R. Typically when comparing the inhibitory activities of the R- and S-stereoisomers, one will be more active than the other, and therefore the preferred stereochemistry is the form that more effectively permits the molecule to function as an arginase inhibitor. Indeed, structural and functional studies have established that the αC stereochemistry as defined immediately above is preferred for tight binding in the enzyme active site; whereas stereoisomers with the opposite configuration do not bind as tightly or are less efficacious.

Alternatively, the stereoisomers may be defined where the ProS hydrogen of glycine depicted below is replaced by an $R^1$ side chain that fits into the enzyme active site. In the compounds of formulas IA and IB, $R^1$ replaces the ProR hydrogen of glycine. According to the Cahn-Ingold-Prelog rules, the designation R or S for the stereoisomers depends upon the hierarchy based on the atoms connected to the chiral carbon. For instance, if $R^1$ is methyl and $X^1 \ldots$ is $-(CH_2)_4B(OH)_2$ then the chirality will be S. However, if $R^1$ is methyl and $X^1 \ldots$ is $-(CH_2)S(CH_2)_2B(OH)_2$ then the chirality will be R. Additionally, if $R^1$ is $(CH_2)OH$ and $X^1 \ldots$ is $-(CH_2)_4B(OH)_2$ then the chirality will be R.

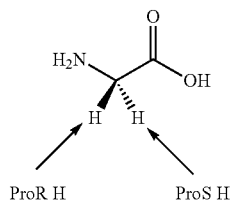

ProR H    ProS H

One skilled in the art will appreciate that the syntheses of such $R^1$ groups at the α-position of an amino acid is a difficult synthetic process as judged by the lack of commercially available α,α-disubstituted amino acids. See, e.g., Vogt et al., Org. Biomol. Chem. 5, 406-30 (2007). As has been demonstrated in the synthetic schemes discussed herein, one or both of the $R^1$ and boronoalkyl side chains needs to be introduced via alkylation reactions onto a suitably protected amino acid scaffold. In fact, the chemistry described herein discloses a novel process of hydroboration of a crotyl group to produce the requisite terminal boronic acids in an amino acid scaffold. See, Yamamoto et al., Tetrahedron 60, 10695-700 (2004).

It should also be appreciated that the addition of the $R^1$ group to the known boronic acid- and N-hydroxy guanidine-type inhibitors can be selected to target binding interactions in the outer active site cleft and the region flanking the outer active site clefts of parasitic arginase, bacterial arginase, and arginases I and II. These $R^1$ substituted compounds would have increased interactions with the target protein which would result in increased potencies or selectivities over the prior art. Furthermore, it should be appreciated that the syntheses of these $R^1$ groups at the α-position of an amino acid is a difficult synthetic process as judged by the lack of commercially available α,α-disubstituted amino acids. See, Vogt et al., Org. Biomol. Chem. 5, 406-30 (2007).

As is demonstrated in the synthetic schemes discussed below, one or both of the $R^1$ and boronoalkyl side chains needs to be introduced via alkylation reactions onto a suitably protected amino acid scaffold. In fact, the chemistry described herein discloses a novel process of hydroboration of a crotyl group to produce the requisite terminal boronic acids in an amino acid scaffold. See, Yamamoto et al., Tetrahedron 60, 10695-700 (2004).

In certain particular embodiments, $R^1$ is $(C_1-C_{20})$alkyl, hydroxy$(C_1-C_{20})$alkyl, hydroxy$(C_2-C_{20})$alkenyl, $(C_2-C_{20})$alkenyl, $(C_2-C_{20})$alkynyl, $(C_5-C_{50})$aryl, $(C_3-C_{50})$heteroaryl having at least one heteroatom selected from N, O, and S; $(C_5-C_{50})$aryl$(C_1-C_{20})$alkyl, $(C_3-C_{50})$heteroaryl$(C_1-C_{20})$alkyl, $(C_2-C_{50})$heterocycloalkyl$(C_1-C_{20})$alkyl, $(C_5-C_{50})$aryloxy$(C_1-C_{20})$alkyl, $(C_5-C_{50})$arylthio$(C_1-C_{20})$alkyl, $(C_3-C_{50})$heteroaryloxy$(C_1-C_{20})$alkyl, $(C_5-C_{50})$arylamino$(C_1-C_{20})$alkyl, $(C_3-C_{50})$heteroarylamino$(C_1-C_{20})$alkyl, amino$(C_1-C_{20})$alkyl, $-R^x-C(=O)-R^y$, $-R^x-O-R^z$, $-R^x-O-R^x-NR^3R^5$, $-R^x-NR^3R^5$, $-R^x-O-C(=O)-R^y$, $(C_1-C_6)$alkyl-B-$(OH)_2$, -L-Y, or labeled derivative thereof; or $R^1$ and said α-carboxylate, when taken together, form a lactone having 4 to 7 ring atoms;

each $R^x$ is independently $(C_1-C_{20})$alkylenyl;

$R^y$ is $(C_1-C_6)$alkyl, $(C_5-C_{50})$aryl$(C_1-C_6)$alkyl, $(C_5-C_{50})$aryloxy$(C_1-C_6)$alkyl, hydroxyl, $(C_1-C_6)$alkoxy, $(C_3-C_5)$cycloalkyl, $N(R^3)_2$, $(C_5-C_{50})$aryl, $(C_3-C_{50})$heteroaryl having at least one heteroatom selected from N, O, and S; heterocyclyl, $(C_5-C_{50})$aryl$(C_1-C_6)$alkyl, or $(C_3-C_{50})$heteroaryl$(C_1-C_6)$alkyl;

$R^z$ is $(C_1-C_6)$alkyl, $(C_3-C_5)$cycloalkyl, $-R^x-O-(C_1-C_6)$alkyl, $(C_5-C_{50})$aryl, $(C_3-C_{50})$heteroaryl having at least one heteroatom selected from N, O, and S; $(C_5-C_{50})$aryl$(C_1-C_6)$alkyl, or $(C_3-C_{50})$heteroaryl$(C_1-C_6)$alkyl;

$R^3$ is, independently, H, $(C_1-C_6)$alkyl, or $(C_1-C_6)$alkyl-N$(R^4)_2$;

$R^4$ is, independently, H or $(C_1-C_6)$alkyl;

$R^5$ is $-C(=O)-(C_1-C_6)$alkyl, $-C(=O)-(C_5-C_{50})$aryl, $-SO_2-(C_5-C_{50})$aryl, $-C(=O)NR^3R^4$, $-C(=O)-NR^4(C_5-C_{50})$aryl, or $-C(=O)$-heterocycle;

or $R^3$ and $R^5$ together form a $(C_2-C_{10})$heterocycloalkyl;

L is an aliphatic or aromatic linkage; and

Y is a residue of an imageable moiety, peptide, peptidomimetic, or carbohydrate.

In certain more particular embodiments, $R^1$ is $(C_1-C_{20})$alkyl, hydroxy$(C_1-C_{20})$alkyl, hydroxy$(C_2-C_{20})$alkenyl, $(C_2-C_{20})$alkenyl, $(C_2-C_{20})$alkynyl, halo, $(C_5-C_{50})$aryl, $(C_3-C_{50})$heteroaryl having at least one heteroatom selected from N, O, and S; $(C_5-C_{50})$aryl$(C_1-C_{20})$alkyl, $(C_3-C_{50})$heteroaryl$(C_1-C_{20})$alkyl, $(C_5-C_{50})$aryloxy$(C_1-C_{20})$alkyl, $(C_3-C_{50})$heteroaryloxy$(C_1-C_{20})$alkyl, $(C_5-C_{50})$arylamino$(C_1-C_{20})$alkyl, heteroarylamino$(C_1-C_{20})$alkyl, amino$(C_1-C_{20})$alkyl, $-R^x-C(=O)-R^y$, $-R^x-C(=O)-O-R^y$, $-R^x-O-R^z$, $-R^x-O-R^x-NR^3R^5$, -L-Y, or labeled derivative thereof; or $R^1$ and said α-carboxylate, when taken together, form a lactone having 4 to 7 ring atoms;

each $R^x$ is independently $(C_1-C_6)$alkylenyl;

$R^y$ is $(C_1-C_6)$alkyl, $(C_3-C_5)$cycloalkyl, $N(R^3)_2$, $(C_5-C_{50})$aryl, $(C_3-C_{50})$heteroaryl having at least one heteroatom selected from N, O, and S; $(C_5-C_{50})$aryl$(C_1-C_6)$alkyl, or $(C_3-C_{50})$heteroaryl$(C_1-C_6)$alkyl;

$R^z$ is $(C_1-C_6)$alkyl, $(C_3-C_5)$cycloalkyl, $(C_5-C_{50})$aryl, $(C_3-C_{50})$heteroaryl having at least one heteroatom selected from N, O, and S; $(C_5-C_{50})$aryl$(C_1-C_6)$alkyl, or $(C_3-C_{50})$heteroaryl$(C_1-C_6)$alkyl;

$R^3$ is, independently, H or $(C_1-C_6)$alkyl;

L is an aliphatic or aromatic linkage;

Y is a residue of an imageable moiety, peptide, peptidomimetic, or carbohydrate.

In certain other embodiments, $R^1$ is $(C_1-C_{20})$alkyl, hydroxy$(C_1-C_{20})$alkyl, $(C_2-C_{20})$alkenyl, $(C_5-C_{50})$aryl, $(C_5-C_{50})$aryl$(C_1-C_{20})$alkyl, $(C_3-C_{50})$heteroaryl$(C_1-C_{20})$alkyl, $(C_5-C_{50})$aryloxy$(C_1-C_{20})$alkyl, amino$(C_1-C_{20})$alkyl, $-R^x-C(=O)-R^y$, $-R^x-C(=O)-O-R^y$, $-R^x-O-R^z$, $-R^x-O-R^x-NR^3R^5$, $-R^x-NR^3R^5$, $-R^x-O-C(=O)-R^y$, $(C_1-C_6)$alkyl-B-$(OH)_2$, -L-Y, or labeled derivative thereof; or $R^1$ and said α-carboxylate, when taken together, form a lactone having 4 to 7 ring atoms.

The foregoing R¹ groups may be unsubstituted or substituted by one or more $R^a$ groups as defined hereinabove (e.g., one or more hydrogen atoms have been replaced with an $R^a$ group).

In yet other certain embodiments,
$R^x$ is $(C_1-C_6)$alkylenyl.

In still yet other certain embodiments,
$R^y$ is hydroxyl, $(C_1-C_6)$alkoxy, $N(R^3)_2$, or heterocyclyl.

In still yet other certain embodiments,
$R^z$ is —$R^x$—O—$(C_1-C_6)$alkyl.

In still yet other certain embodiments,
$R^4$ is, independently, H or $(C_1-C_4)$alkyl.

In still yet other certain embodiments,
$R^5$ is —C(=O)—$(C_1-C_6)$alkyl, —C(=O)—$(C_5-C_{10})$aryl, —$SO_2$—$(C_5-C_{10})$aryl, —C(=O)$NR^3R^4$, —C(=O)—$NR^4(C_5-C_{10})$aryl, or —C(=O)-heterocycle.

In certain preferred embodiments of the compounds of the invention, R preferably comprising an —$(CH_2)_x$— group, where x is an integer from 1 to 3, preferably 1, adjacent to the α-carbon atom, so that there is no substantial steric bulk immediately adjacent to the stereocenter of the amino acid.

In certain preferred embodiments of the compounds of the invention, $R^1$ is a hydroxy$(C_1-C_{20})$alkyl, preferably hydroxy$(C_1-C_6)$alkyl, more preferably hydroxy$(C_1-C_4)$alkyl.

In certain preferred embodiments of the compounds of the invention, $R^1$ is a hydroxy$(C_2-C_{20})$alkenyl, preferably hydroxy$(C_2-C_6)$alkenyl, more preferably hydroxy$(C_2-C_4)$alkenyl.

In certain preferred embodiments, the compounds of the invention are selected from the group consisting of:
2-Amino-2-benzyl-6-boronohexanoic acid;
2-Allyl-2-amino-6-boronohexanoic acid;
2-Amino-2-(4-boronobutyl)succinic acid;
2-Amino-6-(borono-2-(3-phenoxypropyl)hexanoic acid;
2-Amino-6-borono-2-(4-phenylbutyl)hexanoic acid;
2-Amino-6-borono-2-(3-(4-chlorophenoxy)propyl)hexanoic acid;
2-Amino-6-borono-2-(3-(4-methoxyphenoxy)propyl)hexanoic acid;
2-Amino-6-borono-2-(3-(4-fluorophenoxy)propyl)hexanoic acid;
2-Amino-6-borono-2-(3-(4-nitrophenoxy)propyl)hexanoic acid;
2-Amino-2-(3-(benzo[d][1,3]dioxol-5-yloxy)propyl)-6-boronohexanoic acid;
2-Amino-6-borono-2-(3-(4-(trifluoromethyl)phenoxy)propyl)hexanoic acid;
2-Amino-6-borono-2-(3-(3-methoxyphenoxy)propyl)hexanoic acid;
2-Amino-6-borono-2-(3-(3-phenoxyphenoxy)propyl)hexanoic acid;
2-Amino-6-borono-2-(3-(3-isopropylphenoxy)propyl)hexanoic acid;
2-Amino-2-(3-(biphenyl-4-yloxy)propyl)-6-boronohexanoic acid;
2-Amino-2-(3-(biphenyl-3-yloxy)propyl)-6-boronohexanoic acid;
2-Amino-6-borono-2-(3-(3-(trifluoromethyl)phenoxy)propyl)hexanoic acid;
2-Amino-6-borono-2-(3-(4-(trifluoromethylthio)phenoxy)propyl)hexanoic acid;
2-Amino-6-borono-2-(3-(2,6-difluorophenoxy)propyl)hexanoic acid;
2-Amino-6-borono-2-(3-(o-tolyloxy)propyl)hexanoic acid;
2-Amino-6-borono-2-(3-(p-tolyloxy)propyl)hexanoic acid;
4-(4-Amino-8-borono-4 carboxyoctyloxy)benzoic acid;
2-Amino-2-(3-(4-aminophenoxypropyl)-6-boronohexanoic acid;
2-Amino-6-(borono-2-(pyridin-3-ylmethyl)hexanoic acid;
2-Amino-2-(benzyloxyethyl)-6-boronohexanoic acid;
2-Amino-6-borono-2-(2-methoxyethyl)hexanoic acid;
2-Amino-6-borono-2-(2-(p-tolyoxy)ethyl)hexanoic acid;
2-Amino-6-borono-2-(2-(3-chlorophenoxy)ethyl)hexanoic acid;
2-Amino-6-borono-2-(2-(2,3-dihydrobenzo[b][1,4]dioxin-5-yloxy)ethylhexanoic acid;
2-Amino-6-borono-2-((2,3-dihydrobenzo[b][1,4]dioxin-2-yl)methyl)hexanoic acid;
2-Amino-6-borono-2-(2-(3-methoxyphenoxy)ethyl)hexanoic acid;
2-Amino-6-borono-2-(2-(3-nitrophenoxy)ethyl)hexanoic acid;
2-Amino-6-borono-2-(2-(3-(morpholinosulfonyl)phenoxy)ethyl)hexanoic acid;
2-Amino-2-(2-(3-aminophenoxy)ethyl)-6-boronohexanoic acid;
2-Amino-6-borono-2-(3-hydroxypropyl)hexanoic acid;
2-Amino-6-borono-2-(4-boronobutyl)hexanoic acid;
2-Amino-2-(4-boronobutyl)hex-4-enoic acid;
2-Amino-6-borono-2-(2-(2-methoxyethoxy)ethyl)hexanoic acid;
2-Amino-6-borono-2-methylhexanoic acid;
2-Amino-6-borono-2-isobutylhexanoic acid;
2-Amino-6-borono-2-(hydroxymethyl)hexanoic acid;
(R)-2-Amino-6-borono-2-(hydroxymethyl)hexanoic acid;
(S)-2-Amino-6-borono-2-(hydroxymethyl)hexanoic acid;
2-Amino-6-borono-2-(2-(benzyloxy)-2-oxoethyl)-6-boronohexanoic acid;
2-Amino-6-borono-2-(2-methoxy-2-oxoethyl)hexanoic acid;
2-Amino-6-borono-2-(cyanomethyl)hexanoic acid;
2-Amino-6-borono-2-(2-oxobutyl)hexanoic acid;
2-Amino-6-borono-2-(2-oxo-2-phenylethyl)hexanoic acid;
2-Amino-2-(2-(2-aminoethoxy)ethyl)-6-boronohexanoic acid;
2-Amino-6-borono-2-(3-(piperidin-4-yl)propyl)hexanoic acid;
2-Amino-6-borono-2-(3-(piperazine-1-yl)propylhexanoic acid;
2,6-Diamino-2-(4-boronobutyl)hexanoic acid;
2-Amino-6-borono-2-(2-(2-(4-cyanobenzamid)ethoxy)ethyl)hexanoic acid;
2-(2-(2-Acetamidoethoxy)ethyl)-2-amino-6-boronohexanoic acid;
2-Amino-6-borono-2-(2-(2-(3-(3-methoxyphenyl)ureido)ethoxy)ethyl)hexanoic acid;
2-(3-(1-Acetylpiperidin-4-yl)propyl)-2-amino-6-boronohexanoic acid;
2-Amino-6-borono-2-(3-(1-(3-methoxyphenylcarbamoyl)piperidin-4-yl)propyl)hexanoic acid;
2-(3-(4-Acetylpiperazin-1-yl)propyl)-2-amino-6-boronohexanoic acid;
2-Amino-6-borono-2-(3-(4-(4-cyanobenzoyl)piperazine-1-yl)propyl)hexanoic acid;
2-Amino-6-borono-2-(3-(4-(3-methoxyphenylcarbamoyl)piperazin-1-yl)propyl)hexanoic acid;
2-Amino-6-borono-2-(4-(4-methylphenylsulfonamido)butyl)hexanoic acid;
2-Amino-6-borono-2-(4-(3,5-difluorobenzamido)butyl)hexanoic acid;
2-Amino-6-(benzyloxycarbonylamino)-2-(4-boronobutyl)hexanoic acid;
6-Acetamido-2-amino-2-(4-boronobutyl)hexanoic acid;

2-amino-6-borono-2-(4-(3-(3-methoxyphenyl)ureido)butyl)
hexanoic acid;
2-Amino-4-(2-hydroxyguanidino)-2-methylbutanoic acid;
and pharmaceutically acceptable salts thereof. Examples of pharmaceutically acceptable salts include addition salts of hydrochloric and frifluoroacetic acid.

The L-stereoisomers of the foregoing compounds are preferred embodiments of this invention. More particularly, the preferred embodiments of this invention include those compounds analogous (S)-ABH or (S)-norNOHA (see FIG. 18), in which the (R)-proton has been stereospecificly replaced with an $R^1$ group as described herein. These specific derivatives possess the most potency for the inhibition or arginase (lower $K_i$ values, see Example 69, below). Molecular docking of both enantiomers into the crystal structure of arginase indicated that the stereospecific replacement of the (R)—H group resulted in a compound where the boronobutyl side chain can bind near the dimanganese ions in the active site of the enzyme without disruption of important active-site interactions. The products of the stereospecific replacement of the (R)—H group, however, can be described as either having R- or S-stereochemical configuration, depending on the convention for the prioritization of the four substituents on the α-carbon. As an example, the preferred embodiment of compound 1ao (see Example 41, below) is an S-product due to the methyl group having the lowest priority. On the other hand, the preferred embodiment of compound 1d (see Example 4, below) is an R-product due to the higher priority of the phenoxypropyl side chain than the boronobutyl side chain on the α-carbon.

In addition to data from molecular docking studies, laboratory data for the single enantiomers 1ar and 1as (see Examples 44, 45, and 69, below) illustrate the importance of the stereochemistry. A racemic intermediate in the synthesis of compounds 1ar and 1as was resolved by chiral chromatography into single enantiomeric compounds 47a and 47b. The later eluting peak was assigned the R-configuration for the compound based on literature precedent where absolute stereochemistry was proven. See, Lee et al., Org Lett. 7, 1557-60 (2005); Jew et al., Agnew. Chem. Int. Ed. 43, 2382-85 (2004). Each of the single enantiomeric compounds 47a and 47b were converted to final single enantiomeric compounds 1ar and 1as, respectively by unambiguous chemistry. Final compounds 1ar and 1as were tested for arginase inhibition. The enantiomer with the proposed R-configuration, compound 1ar, possessed the most potency as an arginase inhibitor by two orders of magnitude compared to compound 1as. These biological data were consistent with the molecular docking for the preferred embodiments.

In certain preferred embodiments of compounds of the invention, $X^2$ is —S— or —O—.

In certain preferred embodiments of compounds of the invention, $X^2$ is —S—.

In certain preferred embodiments of compounds of the invention, $X^2$ is —O—.

In certain preferred embodiments of compounds of the invention, $X^2$ is —(NR$^2$)—.

In certain preferred embodiments of compounds of the invention, $X^3$ is —S—.

In certain preferred embodiments of compounds of the invention, $X^3$ is —O—.

In certain preferred embodiments of compounds of the invention, $X^3$ is —(NR$^2$)—.

In certain preferred embodiments of compounds of the invention, $R^2$ is H.

In certain preferred embodiments of compounds of the invention, $R^2$ is methyl.

In certain preferred embodiments of compounds of the invention, $R^2$ is ethyl.

In certain preferred embodiments of compounds of the invention, $R^3$ is, independently, H, methyl, or ethyl.

In certain preferred embodiments of compounds of the invention, $R^3$ is H.

In certain preferred embodiments of compounds of the invention, $R^3$ is methyl.

In certain preferred embodiments of compounds of the invention, $R^3$ is ethyl.

Prodrugs of Arginase Inhibitors

In certain preferred embodiments of the compounds of the invention, $R^1$ and the α-carboxylate, when taken together, form a lactone having 4 to 7 ring atoms, preferably a 4- to 7-membered ring lactone. The lactone would undergo hydrolysis in vivo to release the active form of the arginase inhibitor. For example, the HMG-CoA reductase inhibitor lovastatin contains a 6-membered ring lactone that undergoes hydrolysis at gastric pH and temperature (half-life of about 1 hour) to form the pharmacologically active hydroxy acid. See, e.g., Hydrolysis in Drug and Prodrug Metabolism: Chemistry, Biochemistry, and Enzymology, Testa and Mayer, Eds. Wiley Interscience (2003). Thus, a lactone form is essentially a prodrug form of a compound of the invention.

Figure 2:
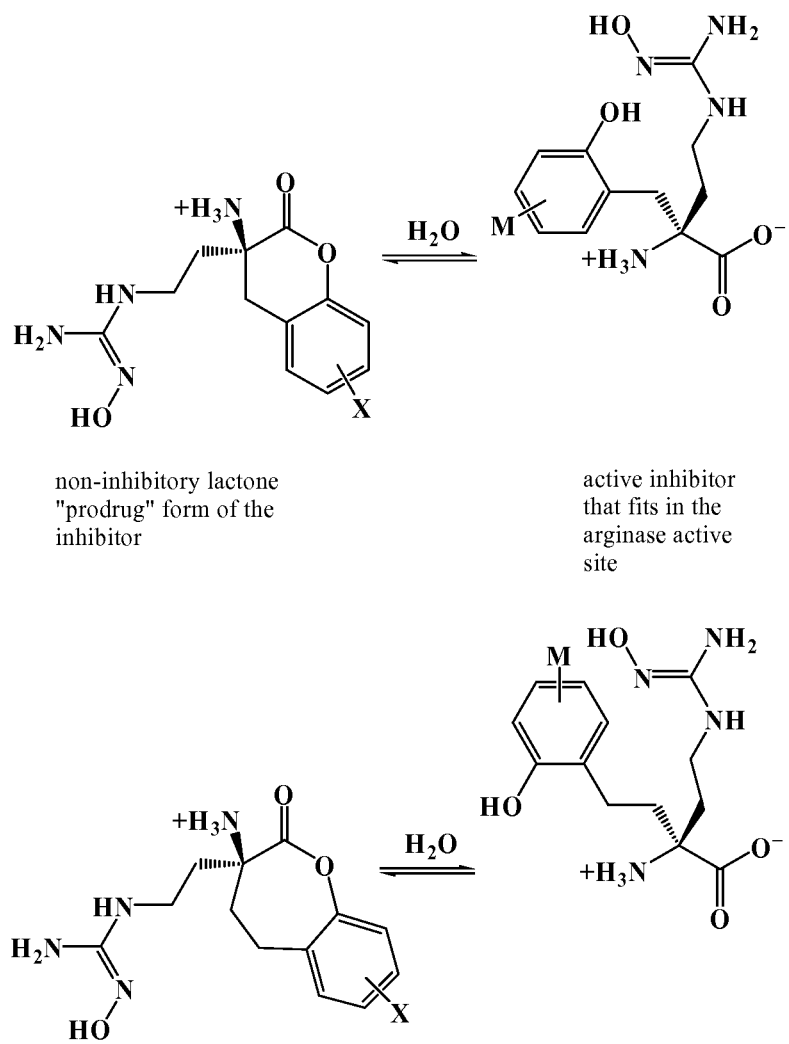

In certain embodiments of the compounds of the invention, $R^1$ may be a hydroxyalkenyl and, together with the α-carboxylate, can form a cyclic lactone, preferably 6- and 7-membered rings, and the double bond can be part of an aromatic ring, as shown below in FIGS. 1-2. The aromatic ring can be otherwise unsubstituted (M=H), or it can be substituted with electron donating groups such as —NH$_2$ or —CH$_3$, or with electron-withdrawing groups such as —NO$_2$ or —Cl, to alter the stability of the ester linkage of the lactone for hydrolysis in vivo. This substitution can be made at any position on the aromatic ring; substitutions at ortho or para positions relative to the phenolic oxygen would allow for direct resonance effects with certain M groups (e.g., —NH$_2$ or —NO$_2$) to modulate the reactivity of the ester linkage. In the case of the 6-membered ring, with M=H, the skeleton of the bicyclic ring system is that of dihydrocoumarin. Unsubstituted dihydrocoumarin has a half-life of about 1 hour at 37° C. in the stomach, so the hydrolysis of the dihydrocoumarin in vivo will release the active form of the arginase inhibitor on a therapeutically-relevant timescale. Preparation of 3-substituted and 3,3-disubstituted dihydrocoumarin derivatives may be prepared by conventional techniques, such as those disclosed in Murakata et al., Chem. Pharm. Bull 47, 1380-83 (1999), which is incorporated herein by reference. The cyclic lactone prodrugs may also be prepared in accordance with the general syntheses described in U.S. Pat. No. 3,161,655 (Dec. 15, 1964), such as Example 11 thereof, which is incorporated herein by reference.

Pharmaceutical Compositions of Arginase Inhibitors

In certain embodiments, the invention is directed to compositions, comprising: at least one compound of the invention or a pharmaceutically acceptable salt thereof; and a pharmaceutically-acceptable carrier.

In other embodiments, the invention is directed to pharmaceutical compositions, comprising:

at least compound of the invention or pharmaceutically acceptable salt thereof; and at least one pharmaceutically acceptable carrier.

Generally, the compound or pharmaceutically acceptable salt thereof will be present in an effective amount. Generally, the compound or a pharmaceutically acceptable salt thereof will be present at a level of from about 0.1%, by weight, to about 90% by weight, based on the total weight of the pharmaceutical composition. Preferably, the compound or a pharmaceutically acceptable salt thereof will be present at a level of at least about 1%, by weight, based on the total weight of the pharmaceutical composition. More preferably, the compound or a pharmaceutically acceptable salt thereof will be present at a level of at least about 5%, by weight, based on the total weight of the pharmaceutical composition. Even more preferably, the compound or a pharmaceutically acceptable salt thereof will be present at a level of at least about 10%, by weight, based on the total weight of the pharmaceutical composition. Yet even more preferably, the compound or a pharmaceutically acceptable salt thereof will be present at a level of at least about 25%, by weight, based on the total weight of the pharmaceutical composition.

Embodiments of the invention also include combination therapies, which include coadministration of an arginase inhibitor hereof with another medicine. More particularly, the term "combination therapy" refers to the administration of two or more therapeutic agents or compounds to treat a therapeutic condition or disorder described in the present disclosure. Such administration includes use of each type of therapeutic agent in a concurrent or simultaneous manner. Such administration includes the use of each type of therapeutic agent in the same unit dosage form or in separate unite dosage forms. In either case, the treatment regimen will provide beneficial effects of the drug combination in treating the conditions or disorders described herein.

Accordingly, in certain embodiments, the invention is directed to compositions, comprising:

a compound of the invention or a pharmaceutically acceptable salt thereof;

a phosphodiesterase-1 (PDE1) inhibitor, a phosphodiesterase-2 (PDE2) inhibitor, a phosphodiesterase-5 (PDE5) inhibitor, or a non-specific PDE inhibitor that inhibits PDE1, PDE2, PDE5, or a combination thereof; and optional pharmaceutically-acceptable excipient.

The arginase inhibitors of the invention are useful in the treatment of patients who do not respond to PDE5 inhibitors because arginase operates at an earlier stage in the pathway leading to NO-dependent relaxation of genital smooth muscle tissue required for sexual arousal.

Suitable phosphodiesterase-1 (PDE1) inhibitors include 5E3623 (available from Eisai), BAY 383045 (available from Bayer), HFV 1017 (7-benzenesulfonylamino-3α-ethyl-1,2,3,3a,10,11b-hexahydro-11H-5a,11a-diaza-benzo[cd]fluoranthene-5-carboxylic acid ethyl ester 2,3-dihydroxy-succinate available from Daiichi Fine Chemical), KF 19514 (5-phenyl-3-(3-pyridil) methyl-3H-imidazo[4,5-c][1,8] naphthyridin-4(5H)-one available from Kyowa Hakko) and SCH 51866 ((cis-5,6a,7,8,9,9α-hexahydro-2-[4-(trifluoromethyl)phenylmethyl]-5-methyl-cyclopent[4,5]imidazo[2,1-b]purin-4(3H)-one) available from Schering-Plough).

Suitable phosphodiesterase-2 (PDE2) inhibitors include BAY 607550 (2-(3,4-Dimethoxy-benzyl)-7-[1-(1-hydroxyethyl)-4-phenyl-butyl]-5-methyl-3H-imidazo[5,1-f][1,2,4]triazin-4-one available from Bayer).

Suitable phosphodiesterase-5 (PDE5) inhibitors include sildenafil (sold under the tradename Viagra™), vardenafil (sold under the tradename Levitra™), tadalafil (sold under the tradename Cialis™), mirodenafil, udenafil, avanafil, dasantafil, NM 702 (4-bromo-6-[3-(4-chloro-phenyl)-propoxy]-5-[(pyridin-3-ylmethyl)-amino]-2H-pyridazin-3-one hydrochloride available from Nissan Chemical Industries), SLx-2101 (available for Surface Logix) and UK 369003 (available from Pfizer).

Suitable non-specific PDE inhibitors that inhibit PDE1, PDE2, PDE5, or a combination thereof include amlexanox, caffeine citrate, doxofylline, levosimendan, mopidamol, pentoxifylline, pemobendan, propentofylline, vesnarinone, and ibudilast.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

In certain embodiments, compounds of the invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal, or subcutaneous injection. Sterile solutions can also be administered intravenously. Oral administration may be either liquid or solid composition form.

Preferably, the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be coadministered to a mammal with one or more other pharmaceutical active agents such as those agents being used to treat any other medical condition present in the mammal. Examples of such pharmaceutical active agents useful for such combination therapies include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), or successively with one or more compounds of the present invention.

The route of administration may be any route, which effectively transports the active compound of the invention to the appropriate or desired site of action, such as oral, nasal, pulmonary, transdermal, such as passive or iontophoretic delivery, or parenteral, e.g., rectal, depot, subcutaneous, intravenous, intraurethral, intramuscular, intranasal, ophthalmic solution or an ointment. Furthermore, the administration of compound of formula Ia or formula Ib with other active ingredients may be concurrent or simultaneous.

It is especially advantageous to formulate the compositions in dosage unit form for ease of administration and uniformity of dosage. Dosage unit form, as used herein, refers to physically discrete units suited as unitary dosages for the patient to be treated; each unit containing a predetermined quantity of the peptide calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of the patients.

The pharmaceutical compositions can be included in a container, pack, or dispenser together with instructions for administration.

Typically, dosages of the compounds of the invention that can be administered to an animal, preferably a human, range in amount from 1 microgram to about 100 milligrams per kilogram of body weight of the animal. The precise dosage administered will vary depending upon any number of factors, including but not limited to, the type of animal and type of disorder being treated, the age of the animal and the route of administration. Preferably, the dosage of the compound will vary from about 10 micrograms to about 10 milligrams per kilogram of body weight of the animal. More preferably, the dosage will vary from about 100 micrograms to about 5 milligrams per kilogram of body weight of the animal.

Typically, the compounds of the invention can be administered as needed or as directed by a health care provider to an animal as frequently as several times daily (e.g., once, twice, or thrice daily), or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disorder being treated, the type and age of the animal, etc.

Diagnostic Uses of Arginase Inhibitors

Diagnostic medical imaging has become a critical element of modern health care. Ultrasound, radionuclide, X-ray, and magnetic resonance imaging techniques facilitate the diagnosis of disease. Diagnostic pharmaceuticals, frequently called contrast agents, may be administered to a patient in place of a therapeutic arginase inhibitors, or they may be simultaneously administered with a therapeutic agent to a patient to augment the usefulness of the imaging technique itself. Such imaging agents act by altering the energy or the way that energy interacts with tissues. Diagnostic medical imaging frequently uses targeted contrast agents that, in binding or localizing at sites selectively within the body, help to resolve an image of diagnostic interest.

Targeted diagnostic imaging contrast agents generally consist of a targeting moiety labeled with a traceable imaging moiety. Such traceable imaging moieties include fluorescent tags; radio-opaque dyes (e.g., iodinated aromatics), radioactive elements such as $^3$H, $^{18}$F, $^{125}$I, $^{129}$I; or diagnostically useful chelated radioactive or paramagnetic metals such as Gd(III), Mn(II), Tc-99m, Re-186, Re-188, In-111, or Ga-67. Examples of useful diagnostic imaging agents of the invention include compounds according to formulas IA, IB, Ia, and Ib, wherein at least one hydrogen atom of the $R^1$ group has been substituted with one of the foregoing imaging moieties.

The targeting moiety carries the label to the site of diagnostic interest where it is detected, e.g., by MRI, US, CT, or radionuclide imaging (including SPECT and PET). In certain preferred embodiments of compounds of formula IA or formula IB, Y is a residue of an imageable moiety selected from the group consisting of a gamma ray emitting radioisotope, a positron emitting radioisotope, a magnetic resonance imaging contrast agent, an X-ray contrast agent, or an ultrasound contrast agent.

By using such an arginase inhibitor suitable conjugated to an imageable moiety, endogenous arginase activity may be visually observed in a patient's body in real time. In order to be effective, the imageable moiety should not significantly interfere with the binding of the derivatized arginase inhibitor to its substrate. For example, arginase-inhibitor imageable-moiety conjugate will generally have a $K_i$ or less than about 1000 nM.

In certain preferred embodiments of compounds of formula IA or formula IB, $R^1$ is a fluorescently-labeled derivative thereof.

In certain embodiments of the invention, a spectroscopic probe, such as a fluorescent moiety or an NMR or MRI sensitive moiety or complex is covalently attached as the $R^1$ group through a flexible linker sufficiently long so that the probe does not make unfavorable interactions with the protein surface. Such spectroscopic probe would be a useful diagnostic tool for noninvasive determination of arginase overexpression, as observed in certain disease states, such as, for example, asthma (overexpression of airway arginase), cancer (overexpression of arginase in certain breast cancers, colon cancers, and the like), or certain internal bacterial infections (e.g., *H. pylori* overexpresses bacterial arginase in order to evade the immune response in human stomach ulcers).

In other embodiments, the invention is directed to methods of diagnosing arginase overexpression in a patient, comprising the step of:

administering to said patient a diagnostically-effective amount of a compound of the invention or a pharmaceutically acceptable salt thereof;
  where $R^1$ is a labeled derivative thereof; and
  imaging said patient.
In certain preferred embodiments, the arginase overexpression is associated with asthma, cancer, bacterial infections, or combinations thereof.

In other aspects, the invention is directed to methods of diagnosing arginase overexpression in a patient, comprising the step of:
administering to said patient a diagnostically-effective amount of a compound of the invention or a pharmaceutically acceptable salt thereof;
  where Y is an imageable moiety; and
  imaging said patient.
In certain preferred embodiments, the arginase overexpression is associated with asthma, cancer, bacterial infections, or combinations thereof.

In certain aspects, the invention is directed to methods for radioimaging a patient, comprising the steps of:
administering to said patient an effective amount of a compound of the invention;
  wherein Y is an imageable moiety; and
  scanning said patient using a radioimaging device.
In certain aspects, the invention is directed to methods of inhibiting arginase, comprising the step of:
contacting said arginase with a compound of the invention or a salt thereof.
In certain embodiments, the arginase is yeast, bacterial, parasitic, or mammalian. In certain other embodiments, mammalian arginase is a human type I arginase or a human type II arginase (e.g., human penile arginase).

In certain aspects, the invention is directed to diagnostic compositions, comprising:
  a diagnostically-effective amount of the compound of the invention or a pharmaceutically acceptable salt thereof; and
  a pharmaceutically acceptable carrier;
  where $R^1$ is a labeled derivative thereof.
In certain aspects, the invention is directed to diagnostic compositions, comprising:
  a diagnostically-effective amount of the compound of the invention or a pharmaceutically acceptable salt thereof; and
  a pharmaceutically acceptable carrier;
  where Y is an imageable moiety.

Therapeutic Uses of Arginase Inhibitors

The invention is based upon the discovery of compounds that inhibit the enzymatic activity of arginase. These compounds, which were not previously known to inhibit this enzyme (and not previously known to have any use), are useful for a variety of applications in medicine and research.

The compounds, compositions, and methods of the invention are useful for inhibiting the activity of arginase including, but not limited to, mammalian (e.g., human), yeast, and bacteria (such as *H. pylori*) arginase. The compounds, compositions, and methods described herein can be used to inhibit arginase activity in vitro or in vivo, for example, in a human. These compositions can also be used to treat a disorder characterized either by abnormally high arginase activity in a tissue of a mammal or by abnormally low nitric oxide synthase activity in a tissue of the mammal, preferably a human. "Inhibition" of arginase by an arginase inhibitor, as used herein, means reduction in the level of arginase activity in the presence of the inhibitor, compared with the level of arginase activity in the absence of the inhibitor.

There are a large number of arginase-linked diseases, some of which are listed below. They are linked with the one, two, or all of the three phenomena related to constitutive or upregulated arginase activity described above. Many of these diseases are characterized by two or even three of the phenomena simultaneously or sequentially, e.g., cellular proliferation and accumulation of fibrotic tissue can stiffen airway or vascular tissue in a constricted state so that it is more difficult to achieve NO-dependent relaxation. Accordingly, the compounds of the invention may be used to treat conditions associated with abnormally high level of arginase activity or abnormally low level of NO synthase activity. An "abnormally high level of arginase activity," as used herein, means a level of arginase activity that exceeds the level found in normal tissue when the normal tissue does not exhibit an arginase related disorder phenotype. An "abnormally low level of NO synthase activity," as used herein, means a level of NO synthase activity which is lower than that found in normal tissue when the normal tissue does not exhibit an NO synthase related disorder phenotype.

For example, the arginase inhibitors disclosed herein may be useful in the treatment, prevention, management, or diagnosis of one or more of the following diseases, conditions, or maladies, each of which is discussed individually below: (1) gastrointestinal diseases, (2) pulmonary inflammatory diseases, (3) sexual arousal disorders, (4) cardiovascular disorders, (5) diseases caused by a pathogenic microorganisms, (6) immunological disorders, (7) cancer, (8) pre-term labor, (9) Reynaud's disease, (10) psoriasis, (11) rheumatoid arthritis, and (12) Peyronie's Disease, among others. Each of these conditions is discussed below.

1. Gastrointestinal Diseases

An increase in arginase activity has been associated with the pathophysiology of a number of conditions including impairment in non-adrenergic and non-cholinergic (NANC) nerve-mediated relaxation of gastrointestinal smooth muscle. An arginase inhibitor can be used to alleviate such impairment by administering the inhibitor to a mammal experiencing such impairment or a mammal which is anticipated to experience such impairment (e.g., a human afflicted with a gastrointestinal motility disorder).

Accordingly, the compounds of the invention may be useful in the treatment or prevention of gastrointestinal motility disorders, which is based on the observation that arginase is present in opossum internal anal sphincter muscle and the known arginase inhibitor, ABH, has been shown to relax this muscle. See, e.g., Baggio et al., J. Pharm. Exp. Ther. 290, 1409-16 (1999).

The compounds of the invention may also be useful in the treatment or prevention of inflammatory bowel disease (e.g., Crohn's disease and ulcerative colitis). In fact, IBD has been shown to be characterized by increased arginase activity and endothelial dysfunction. See, e.g., Horowitz et al., Am. J. Physiol. Gastrointest. Liver Physiol. 292, G1323-36 (2007).

Likewise, the compounds of the invention may be useful in the treatment or prevention of gastric ulcers, because the bacterium that causes stomach ulcers, *Helicobacter pylori*, exhibits increased arginase activity upon colonization in order to evade the human immune response. See, e.g., Gobert et al., Proc. Natl. Acad. Sci. (USA) 98, 13844-49 (2001).

2. Pulmonary Inflammatory Diseases

The compounds of the invention may be useful in the treatment or prevention of asthma based on the observation that arginase is upregulated in the asthmatic airway. See, e.g., Zimmermann and Rothenberg, Eur. J. Pharmacol. 533, 253-62 (2006). Furthermore, nebulizer treatment of guinea pigs with ABH in an allergic asthma model prevents airway hyperresponsiveness. See, e.g., Maarsingh, "Arginase: A Novel Key Enzyme in the Pathophysiology of Allergic Asthma," Ph. D. dissertation, Chapter 9, University of Groningen, Netherlands (2006); Maarsingh et al., Am. J. Respir. Crit. Care Med. 178, 565-73 (2008). The asthma phenotype is characterized by airway constriction, airway smooth muscle hyperplasia, and the chronic accumulation of fibrotic tissue; an arginase inhibitor can relax airway smooth muscle and attenuate cellular hyperplasia and fibrosis.

Additionally, the compounds of the invention may be useful in the treatment or prevention of chemically-induced lung fibrosis because arginase I and II are induced in bleomycin-induced lung fibrosis in order to provide more L-ornithine for collagen biosynthesis. See, e.g., Endo et al., Am. J. Physiol. Lung Cell Mol. Physiol. 285, L313-21 (2003).

The compounds of the invention may also be useful in the treatment or prevention of idiopathic pulmonary fibrosis, based on the observation that virus-induced upregulation of arginase I is observed in an animal model. See, e.g., Mora et al., Am. J. Respir. Cell Mol. Biol. 35, 466-73 (2006).

Furthermore, the compounds of the invention may be useful in the treatment or prevention of cystic fibrosis. Increased sputum arginase activity contributes to NO deficiency in cystic fibrosis lung disease; arginase activity also contributes to fibrosis. See, e.g., Graseman et al., Am. J. Respir. Crit. Care Med. 172, 1523-28 (2005).

3. Sexual Arousal Disorders

Erectile dysfunction afflicts one-half of the male population over the age of forty. This malady often results from defects in the complex cascade of enzyme-catalyzed reactions governing blood flow into and out of the corpus cavernosum, a chamber of muscular, spongy tissue that becomes engorged with blood in the erect penis. Defects that compromise cavernosal blood flow often occur as secondary complications related to other health conditions, such as heart disease, hypertension, diabetes, use of certain medications, and the like.

In an important embodiment, the invention relates to use of an arginase inhibitor described herein for enhancing penile erectile function in a mammal (preferably a male human) or for alleviating erectile dysfunction in a mammal. NO is an important regulator of erectile function and mediates NANC neurotransmission in penile corpus cavernosum smooth muscle, leading to rapid relaxation, which in turn leads to erection. NO synthase, which catalyzes oxidation of L-arginine to form L-citrulline and NO, is for this reason a key enzyme in penile smooth muscle physiology. Arginase catalyzes hydrolysis of L-arginine to form L-ornithine and urea. Arginase regulates NO synthase activity by affecting the amount of L-arginine available for oxidation catalyzed by NO synthase activity. Thus, inhibition of arginase activity can enhance NO synthase activity, thereby enhancing NO-dependent smooth muscle relaxation in the corpus cavernosum and enhancing penile erection.

Arginase is present in rabbit and human penile corpus cavernosum and ABH enhances the NO-dependent relaxation of this tissue. See, e.g., Cox et al., Nature Struct. Biol. 6, 1043-47 (1999). The arginase inhibitor, ABH, enhances the erectile response in live male rabbits. See, e.g., Cama et al., Biochemistry 42, 8445-51 (2003). Arginase II is upregulated in the corpus cavernosum of the diabetic man, resulting in reduced NO biosynthesis which, in turn, leads to erectile dysfunction; administration of ABH in ex vivo experiments restores NO biosynthesis. See, e.g., Bivalacqua et al., Biochem. Biophys. Res. Commun. 283, 923-27 (2001). Arginase I is upregulated in the penis of aged mice and impairs erectile function. See, e.g., Bivalacqua et al., Am. J. Physiol. Heart Circ. Physiol. 292, H1340-51 (2007).

The compounds of the invention may also be useful in the treatment or prevention of female sexual arousal disorder. The arginase inhibitor, ABH, enhances the engorgement response in the genitalia of live female rabbits. See, e.g., Cama et al., Biochemistry 42, 8445-51 (2003).

4. Cardiovascular Disorders

The compounds of the invention may be useful in the treatment or prevention of endothelial vascular dysfunction in atherosclerosis, hypertension, hypercholesterolemia, and diabetes. Arginase modulates NOS activity by regulation of L-arginine availability, and the deleterious effects of arginase can be blocked by an arginase inhibitor. See, e.g., Berkowitz et al., Circulation 108, 2000-06 (2003); Yang and Ming, Clin. Med. Res. 4, 53-65 (2006). Increased arginase activity in diabetes contributes to vascular endothelial dysfunction by decreasing L-arginine availability to NO synthase. See, e.g., Romero et al., Circ. Res. 102, 95-102 (2008). Arginase inhibition attenuates hypertension in spontaneously hypertensive rats. See, e.g., Demougeot et al., J. Hypertens. 23, 971-78 (2005). Other relevant conditions include ischemia-reperfusion injury, peripheral vascular disease (PVD), peripheral arteial disease (PAD), and subarachnoid hemorrhage. Arginase has been identified as a new drug target for the treatment of atherosclerosis. See, e.g., Yang and Ming, Curr. Hypertension Rep. 8, 54-59 (2006).

The compounds of the invention may be useful in the treatment or prevention of pulmonary arterial hypertension. Elevated arginase activity contributes to vascular endothelial dysfunction by compromising L-arginine availability to NO synthase. See, e.g., Morris et al., Adv. Pulmonary Hypertension 5, 31-36 (2007).

5. Diseases Caused by Pathogenic Microorganisms

The compounds of the invention may be useful in the treatment or prevention of African sleeping sickness, Chagas' disease, leishmaniasis, malaria, and other diseases caused by pathogenic microorganisms. Polyamine biosynthetic enzymes are essential for growth and survival of protozoa. See, e.g., Heby et al., Biochem. Soc. Trans. 31, 415-19 (2003). Arginase is essential for viability. See, e.g., Roberts et al., J. Biol. Chem. 279, 23668-78 (2004). Therefore, inhibitors of protozoan arginases can kill the protozoa.

Additionally, certain bacteria hydrolyze D-arginine with an enzyme known as D-arginase, also known as guanidinobutyrase, Arakawa et al., J. Biochem. 133, 33-42 (2003), and the D-stereoisomers of the compounds of formula IA and IB are expected to be effective inhibitors of this hydrolysis. Further, the compounds of formula IA and IB would also be suitable as antibacterial agents because they are expected to exhibit antibacterial properties, e.g., against guanidinobutyrase of *Pseudomonas aeruginosa*. See, Nakada and Itoh, J. Bacteriol. 184, 3377-84 (2002).

Arginase can be inhibited in yeast by contacting the yeast with the composition of the invention. Inhibition of arginase in yeast serves to minimize urea production during fermentation of alcoholic beverages.

6. Immunological Disorders

The compounds of the invention may be useful in the treatment or prevention of multiple sclerosis, and possibly other autoimmune diseases, based upon the observation that arginase I is upregulated in an animal model of multiple sclerosis (experimental autoimmune encephalomyelitis) and administration of the arginase inhibitor ABH improves the disease score of animals. See, e.g., Xu et al., Immunology 110, 141-48 (2003).

7. Cancer

Tumor-induced tolerance impairs the therapeutic efficacy of immunotherapy; one mechanism leading to T-cell tolerance is the generation of myeloid-derived suppressor cells (MDSCs), which produce arginase, thereby depleting the tumor microenvironment of L-arginine, which impairs T-cell signal transduction and function. T-cell anergy results. Notably, arginase activity is a mechanism of immune system evasion that is also shared by certain bacteria, e.g., *Helicobacter pylori*. MDSCs are regarded as "cancer's bulwark against immune attack." See, e.g., Marx, Science 319, 154-56 (2008).

Accordingly, arginase is upregulated in the following types of cancers, which may be treated with an arginase inhibitor described herein: Renal cell carcinoma (see, e.g., Zea et al., Cancer Res. 65, 3044-48 (2005); Ochoa et al., Clin. Cancer Res. 13, 721s-26s (2007)); prostate cancer (see, e.g., Bronte et al., J. Exp. Med. 201, 1257-68 (2005) (arginase inhibition with N-hydroxy-L-arginine facilitates tumor immunotherapy); colorectal cancer (see, e.g., Leu and Wang, Cancer 70, 733-36 (1992); Bronte and Zanovello, Nature Rev. Immunol. 5, 641-54 (2005)); breast cancer (see, e.g., Singh et al., Cancer Res. 60, 3305-12 (2000); Bronte and Zanovello, Nature Rev. Immunol. 5, 641-54 (2005) (the arginase inhibitor, N-hydroxy-L-arginine, inhibits cell proliferation and induces apoptosis)); skin cancer (squamous cell and basal cell cancers) (see, e.g., Gokmen et al., J. Lab. Clin. Med. 137, 340-44 (2001); Bronte and Zanovello, Nature Rev. Immunol. 5, 641-54 (2005)); lung cancer (see, e.g., Rodriguez et al., J. Exp. Med. 202, 931-39 (2005); Bronte and Zanovello, Nature Rev. Immunol. 5, 641-54 (2005)); ovarian cancer (see, e.g., Melichar et al., J. Translational Med. 1, 1-5 (2003) (doi:10.11861479-5876-1-5)); and gastric cancer (see, e.g., Wu et al., Life Sci. 51, 1355-61 (1992)); among others.

8. Management of Pre-Term Labor

Enhancement of uterine smooth muscle relaxation with an arginase inhibitor may be useful in the management of pre-term labor.

9. Reynaud's Disease

Reynaud's disease is a disease of the microvasculature. Because subcutaneous administration of the arginase inhibitor BEC (which is an analogue of ABH) in humans is vasodilatory and enhances circulation, an arginase inhibitor may be useful in treating Reynaud's disease. See, e.g., Holowatz et al., J. Physiol. 574, 573-81 (2006).

10. Psoriasis

Arginase I is highly overexpressed in the hyperproliferative psoriatic epidermis in human skin, and therefore arginase inhibitors may be useful in the treatment of psoriasis. See, e.g., Bruch-Gerharz et al., Am. J. Pathology 162, 203-11 (2003).

11. Rheumatoid Arthritis

Arginase II is upregulated in synovial fluid from human patients, and therefore arginase inhibitors may be useful in the treatment of arthritis. See, e.g., Huang et al., Kaohsiung J. Med. Sci. 17, 358-63 (2001); Corraliza and Moncada, J. Rheumatol. 29, 2261-65 (2002).

12. Peyronie's Disease

The compounds of the invention may be useful in the treatment or prevention of Peyronie's disease. Arginase II is upregulated in the rat penis in an animal model for this disease. See, e.g., Bivalacqua et al., J. Andrology 22, 497-506 (2001). While this disorder can contribute to erectile dysfunction, it is principally an inflammatory condition in which fibrotic tissue builds up in the penis.

13. General

The composition of the invention can be used to treat a disorder in a mammal, wherein the disorder is associated with expression of an abnormally high level of arginase activity in a tissue of the mammal. Because NO synthase activity is regulated in a reciprocal fashion with respect to arginase activity in mammals, more particularly humans, the compounds and compositions of the invention can be used to treat a disorder in a mammal, wherein the disorder is associated with expression of an abnormally low level of NO synthase activity in a tissue of the mammal. Since the reciprocal interaction of arginase and NO synthase has implications for the function of smooth muscle, the use of the compounds described herein for the regulation of smooth muscle activity in an animal is also contemplated in the invention. Of course, a compound of the invention or a composition comprising the compound of the invention which comprises an arginase inhibitor described herein can also be used to inhibit arginase in a mammal having normal levels of arginase and NO synthase activity, particularly where the physiology which is desired to be effected is one which is affected by arginase or NO synthase activity, or where a disorder which is not caused by aberrant arginase or NO synthase activity levels can nonetheless be alleviated or inhibited by inhibiting arginase activity (e.g., certain forms of erectile dysfunction).

The invention also includes a method of enhancing smooth muscle relaxation comprising contacting the smooth muscle with an arginase inhibitor. The smooth muscle is preferably within the body of an animal. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

When the smooth muscle in within the body of the animal, the invention includes a method of alleviating (e.g., reducing the incidence or severity) or inhibiting (e.g., reducing the likelihood of developing, or preventing) an arginase-related disorder in an animal. In a preferred embodiment, the animal is a human.

To alleviate an arginase-related disorder in a mammal, an arginine inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant NO synthase activity, or to one which exhibits normal (i.e. non-diseased) levels of arginase and NO synthase activities, but in which inhibition of arginase activity is desired. The invention also contemplates use of an arginase inhibitor in an in vitro arginase inhibition/smooth muscle relaxation functional assay, for the purpose of identifying compounds which affect smooth muscle function. Compounds so identified are considered to be candidate arginase inhibitor antagonists, in that these compounds are identified by their ability to counteract the inhibition of arginase activity. For example, these compounds by be identified by using an assay for smooth muscle activity using the internal anal sphincter muscle and one on the arginase inhibitors of the invention. In this assay, strips of the internal anal sphincter muscle obtained from a mammal (e.g., an adult opossum) are induced to relax by NANC nerve-mediated relaxation using electrical field stimulation (EFS); relaxation is reversed by contacting the muscle strips with arginase; and reversal of relaxation is accomplished by contacting the muscle with an arginase inhibitor. To identify an arginase inhibitor antagonist, the muscle strips are then subsequently contacted with a test compound. The effect of the test compound on subsequent reversal of muscle relaxation is assessed. Any significant reversal of the relaxation state of the muscle in the presence of the test compound, compared with the relaxation state of the muscle in the absence of the test compound, is an indication that the test compound is an arginase inhibitor antagonist.

Accordingly, in certain embodiments, the invention is directed to methods of inhibiting arginase in a mammal, comprising the step of:

administering to said mammal an effective amount of a compound of formula Ia or formula Ib or a pharmaceutically acceptable salt thereof.

Accordingly, in certain embodiments, the invention is directed to methods of treating an arginase-related disorder in a mammal, comprising the step of:

administering to said mammal an effective amount of a compound of formula Ia or formula Ib or a pharmaceutically acceptable salt thereof. In certain preferred embodiments, the arginase-related disorder is a disorder associated with an abnormally low level of nitric oxide synthase activity in a tissue of the human, a disorder associated with an abnormally high level of arginase activity in a tissue of the human, or combinations thereof, including heart disease, systemic hypertension, pulmonary hypertension, erectile dysfunction, autoimmune encephalomyelitis, chronic renal failure, gastrointestinal motility disorders, gastric cancers, reduced hepatic blood flow, insufficient hepatic blood flow, cerebral vasospasm, or a combination thereof.

In still other certain embodiments, the invention is directed to methods of relaxing smooth muscle in a mammal, comprising the step of:

administering to said mammal an effective amount of a compound of formula Ia or formula Ib or a pharmaceutically acceptable salt thereof. In certain preferred embodiments, the smooth muscle which is relaxed according to this method is at least one selected from the group consisting of a gastrointestinal smooth muscle, anal sphincter smooth muscle, esophageal sphincter muscle, corpus cavemosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle.

In certain embodiments, the invention is directed to methods of treating a disease or condition associated with upregulation of arginase in a mammal, comprising the step of:

administering to said mammal an effective amount of a compound of formula Ia or formula Ib or a pharmaceutically acceptable salt thereof;

wherein said disease or condition is a gastrointestinal disease, a pulmonary inflammatory disease, a sexual arousal disorder, a cardiovascular disorder, a hemolytic disorder, an autoimmune disease, wound healing, a disease caused by parasitic protozoa, a disease caused by bacteria, a cancer, pre-term labor, psoriasis, or a combination thereof.

Inhibiting arginase impacts cancer in two ways. The first way is relief from immune-suppression that leads to tolerance of the tumor and the second way is by restricting the production of ornithine and subsequent polyamines, which have a role in proliferation.

In certain preferred embodiments, the gastrointestinal disease is a gastrointestinal motility disorder, inflammatory bowel disease, Crohn's disease, ulcerative colitis, gastric ulcer, adenotonsilar disease or a combination thereof.

In certain preferred embodiments, the pulmonary inflammatory disease is asthma, chemically-induced lung fibrosis, idiopathic pulmonary fibrosis, cystic fibrosis, chronic obstructive pulmonary disease (COPD) or a combination thereof.

In certain preferred embodiments, the sexual arousal disorder is male erectile dysfunction, Peyronie's Disease, or a female sexual arousal disorder.

In certain preferred embodiments, the cardiovascular disorder is endothelial vascular dysfunction in atherosclerosis, hypertension, ischemia reperfusion injury, peripheral vascular disease, peripheral arterial disease, subarachnoid hemorrhage, hypercholesterolemia, diabetes, or a combination thereof, diabetic cardiovascular disease, pulmonary arterial hypertension, Reynaud's disease, or a combination thereof.

In certain preferred embodiments, the hemolytic disorder is paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, malaria, cardiopulmonary bypass, mechanical heart valve-induced anemia, chemical induced anemia, or a combination thereof.

In certain preferred embodiments, the autoimmune disease is encephalomyelitis, multiple sclerosis, anti-phospholipid syndrome 1, autoimmune hemolytic anaemia, chronic inflammatory demyelinating polyradiculoneuropathy, dermatitis herpetiformis ("Celiac Disease"), dermatomyositis, myasthenia gravis, pemphigus, rheumatoid arthritis, stiff-person syndrome, type 1 diabetes, ankylosing spondylitis, or a combination thereof.

In certain preferred embodiments, the condition is wound healing.

In certain preferred embodiments, the disease caused by parasitic protozoa is African sleeping sickness, Chagas' disease, leishmaniasis, malaria, or a combination thereof.

In certain preferred embodiments, the cancer is renal cell carcinoma, prostate cancer, colorectal cancer, breast cancer, skin cancer, lung cancer, ovarian cancer, gastric cancer, or a combination thereof. In certain embodiments, the skin cancer is a squamous cell cancer, basal cell cancer, or a combination thereof.

In certain preferred embodiments, the condition is pre-term labor.

In certain preferred embodiments, the condition is Reynaud's disease.

In certain embodiments, the invention is directed to methods of providing relief from immune suppression in a mammal, comprising the step of:

administering to said mammal an effective amount of a compound of formula Ia or formula Ib or a pharmaceutically acceptable salt thereof;

wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

In certain embodiments, the invention is directed to methods of inhibiting the production of ornithine in a mammal suffering from at least one tumor, comprising the step of:

administering to said mammal an effective amount of a compound of formula Ia or formula Ib or a pharmaceutically acceptable salt thereof.

In addition, the compounds and compositions of the invention are useful as anti-fungicides in agriculturally or otherwise economically important plant life. The compounds and compositions of the invention can be therapeutically administered to a plant by spraying or other means well known in the art of plant biology.

Synthesis of Arginase Inhibitors

The compounds of the present invention may be prepared in a number of ways well known to those skilled in the art. The compounds can be synthesized, for example, by the methods described below, or variations thereon as appreciated by the skilled artisan. Variables used are as defined for formula Ia or formula Ib, unless otherwise noted. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

In accordance with this invention, the boronic acid derivatives (where Z is

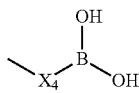

in the compounds of formula Ia or formula Ib) may be prepared as generally described in FIGS. 3-17, discussed below.

The compounds of formula IA or formula IB containing a double bond between $X^3$ and $X^4$ may be prepared in accordance with the synthetic scheme set forth in Collet, et al. (2000) *J. Chem. Soc., Perkin Trans.* 1, 177-182, which is incorporated herein by reference in its entirety, with the appropriately substituted $R^1$ group.

In accordance with this invention, the N-hydroxy guanidine derivatives (where Z is

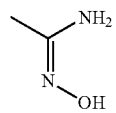

and $X^3$ is —($NR^2$)— ) in the compounds of formula IA or formula IB and where the Cα is substituted by $R^1$) may be prepared as generally described herein.

Figure 3:
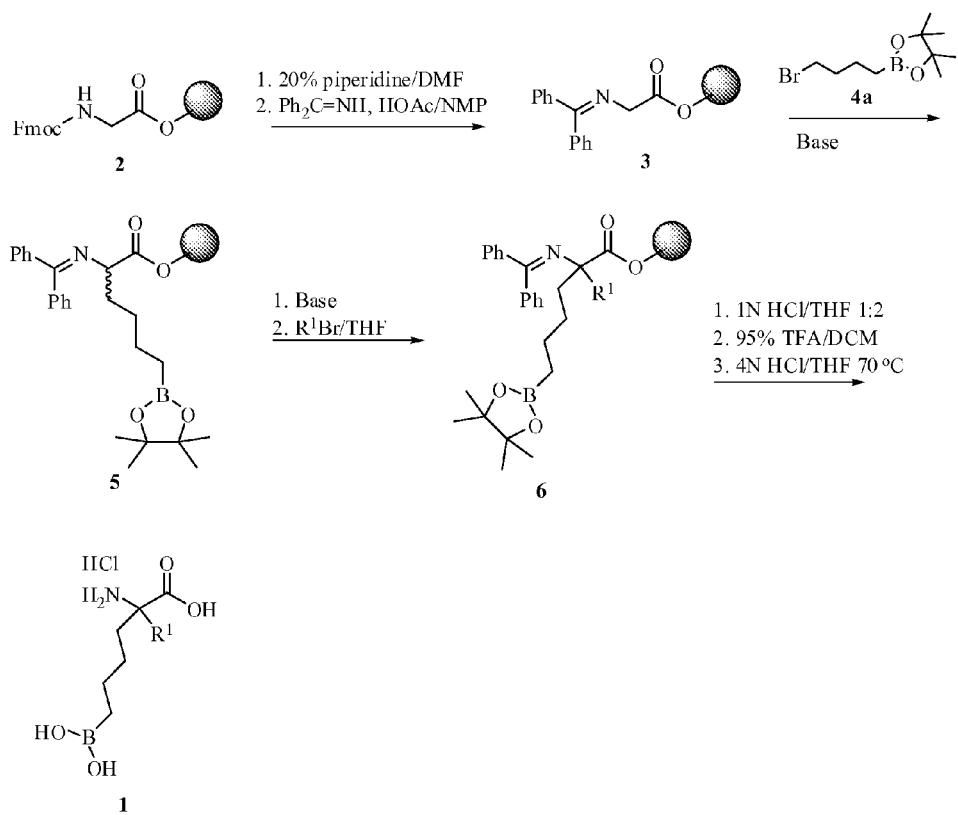
FIGS. 3 through 17 schematically illustrate the synthesis of several exemplary compounds of the invention.

In the attached drawings, FIG. 3 schematically illustrates the solid-phase synthesis of compounds 1 of the present invention, where $R^1$ is generated from reagents that are "activated" alkyl halides, such as benzyl bromide. The Fmoc group of Fmoc-Gly-Wang resin is removed by methods well known in the art. Atherton and Sheppard, "The Fluorenylmethoxycarbonyl Amino Protecting Group," in The Peptides, Udenfriend and Meienhofer, Eds., Academic Press, New York (1987), vol. 9, p. 1). The amine is protected as the N-diphenylmethylene amine by treating the resin-bound free amine with excess benzophenone imine and glacial acetic acid in NMP. See, O'Donnell et al., Tetrahedron Lett., 38, 7163 (1997) resulting in compound 3. This protected glycine is reacted with excess 2-(4-bromobutyl)-4,4,5,5-tetramethyl-1,3,2-dioxaborolane (4a) in the presence of an organic non-nucleophilic base such as BEMP or BTPP in NMP resulting in compound 5. The reaction can be accelerated by the addition of tetrabutylammonium iodide or even more preferred the alkylating reagent can be the iodo derivative instead of the bromo compound. The second side chain can be introduced by treating 5 with a strong base such as n-BuLi, LDA, or the preferred base KHMDS under anhydrous conditions and then adding another alkyl halide, such as benzyl bromide resulting in compound 6. See, Griffith et al., Tetrahedron Lett. 38, 8821 (1997). The desired amino acid (1, wherein $R^1$ may be of a number of sidechains as described herein) can be released from the resin by treating with strong aqueous acid at high temperature (not shown) or, alternatively, the controlled deprotection and release of compound 1 can be completed in a stepwise manner as illustrated in FIG. 3.

Figure 4:
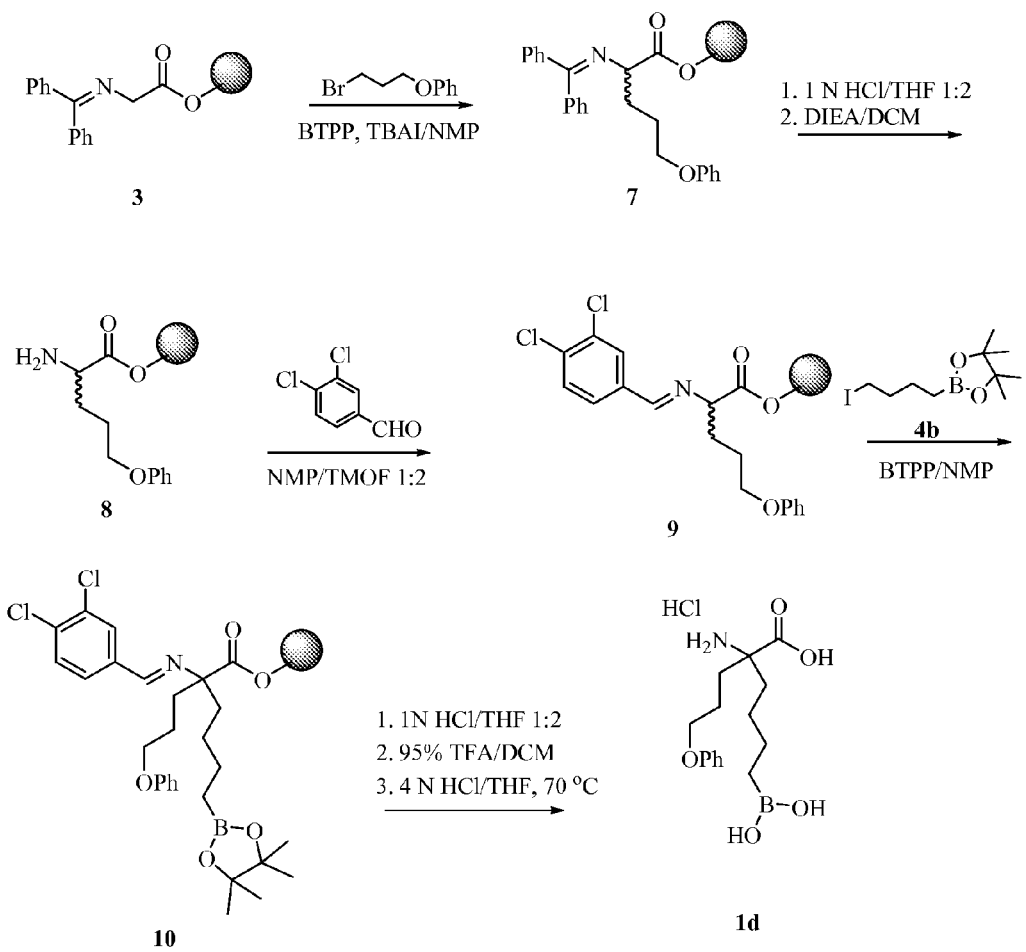

FIG. 4 outlines an exemplary solid-phase synthesis of compound 1d of the present invention, where $R^1$ is generated from reagents that are "unactivated" alkyl halides such as bromoethane. Compound 3 is reacted with excess alkyl halide in the presence of an organic non-nucleophilic base such as BEMP or BTPP in NMP resulting in compound 7. The reaction can be accelerated by the addition of tetrabutylammonium iodide or even more preferred the alkylating reagent can be the iodo-derivative instead of the bromo-compound. The second side chain can be introduced after the amine protecting group is switched from the ketimine to an aldimine as shown in FIG. 4 by first treating compound 7 under mild aqueous acid, neutralizing the hydrochloride salt, and then reacting compound 8 with a benzaldehyde under dehydrating conditions to give compound 9. This intermediate was reacted with 2-(4-iodobutyl)-4,4,5,5-tetramethyl-1,3,2-dioxaborolane (4b) and BTPP in NMP to give compound 10. See, Scott, Tetrahedron Lett. 38, 3695 (1997). Amino acid 1d can be released from the resin by treating with strong aqueous acid at high temperature (not shown) or, alternatively, by controlled deprotection and release of compound 1d by the stepwise process illustrated in FIG. 4.

Figure 5:
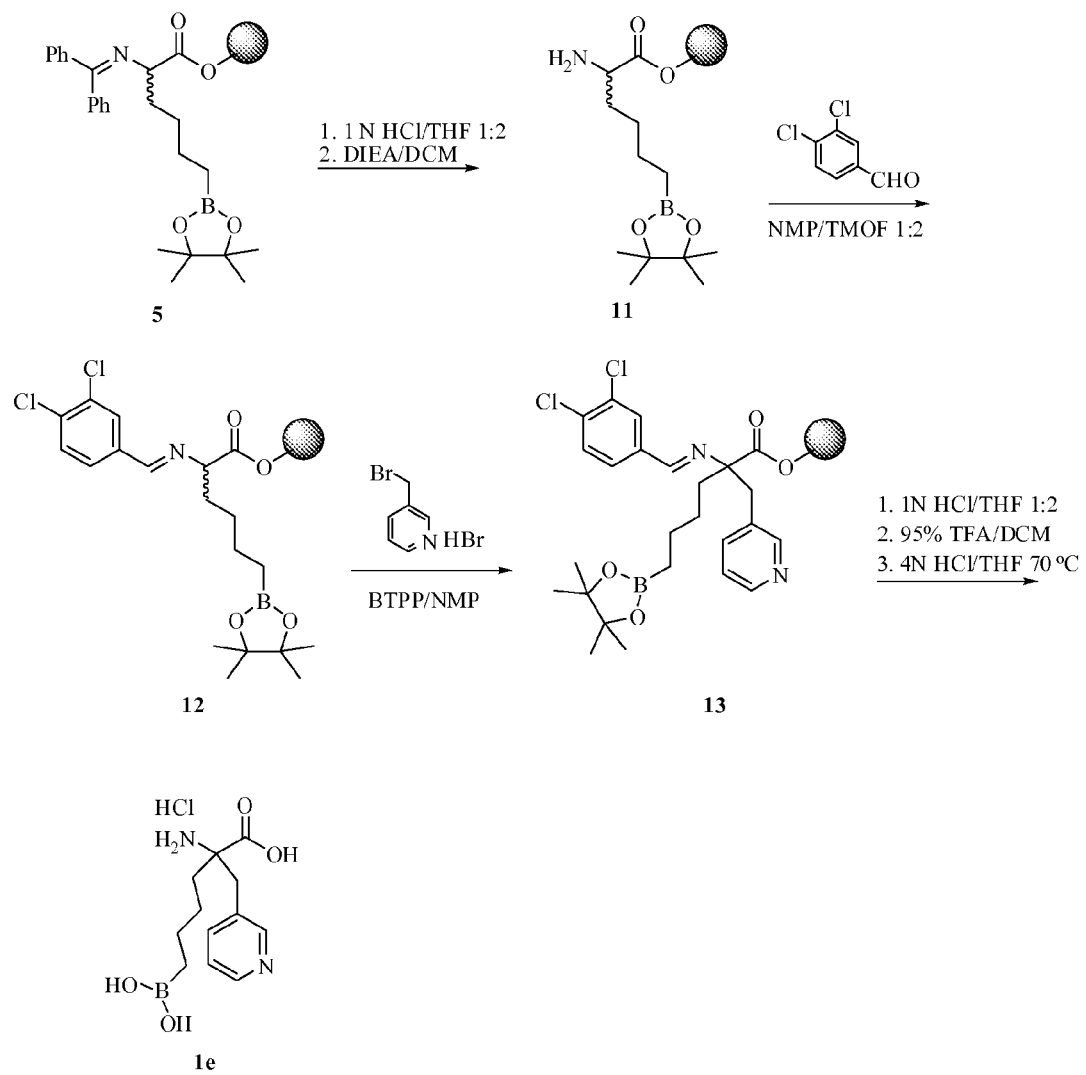

FIG. 5 outlines the solid-phase synthesis of some compounds of the present invention where $R^1$ is generated from reagents such as bromomethylpyridine that may be unstable to KHMDS or other very strong bases. According to this method, compound 5 is treated with mild aqueous acid followed by neutralization of the hydrochloride salt to produce 11. This intermediate is protected as the aldimine 12, which is then treated with excess alkylating agent and BTPP in NMP to give intermediate 13 (Scott, W. L., Tetrahedron Lett. 1997, 38:3695). The desired amino acid (1e) is released from the resin by treating with strong aqueous acid at high temperature (not shown) or, alternatively, the controlled deprotection and release of 1e can be done stepwise as shown in FIG. 5.

Figure 6:
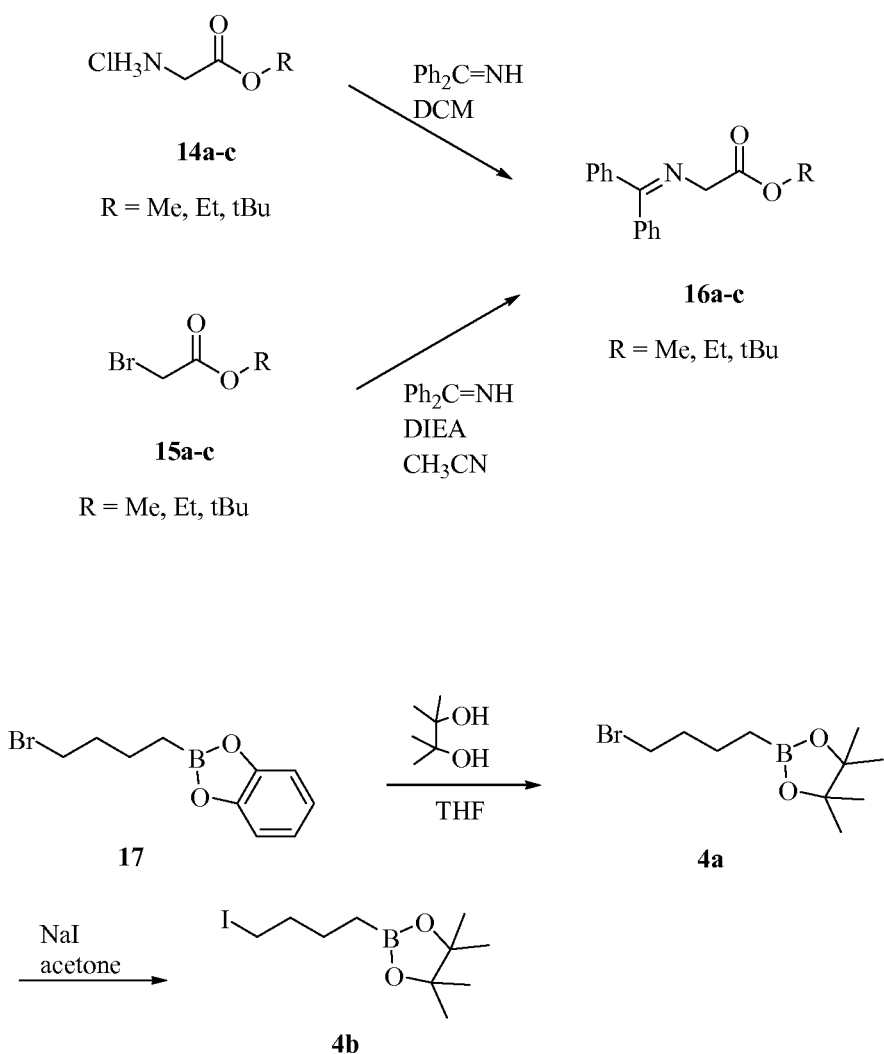

FIG. 6 schematically illustrates the solution-phase syntheses of useful starting materials 16a (wherein R=methyl), 16b (wherein R=ethyl), and 16c (wherein R=tert-butyl) and alkylating reagents 4a and 4b. In the first reaction at the top of FIG. 6, the hydrochloride salt of a glycine alkyl ester 14a-c is reacted with benzophenone imine, O'Donnell, et al., J. Org. Chem. 47, 2663 (1982), at room temperature to give the corresponding ketimine protected glycine ester 16a-c. This transimination is particularly useful for tert-butyl ester 16c. Alternatively, alkyl esters of α-bromoacetic acid 15a-c can be reacted with benzophenone in refluxing acetonitrile as shown in the second reaction resulting in 16a-c. O'Donnell, Acc. Chem. Res. 37, 506 (2004).

Figure 7:
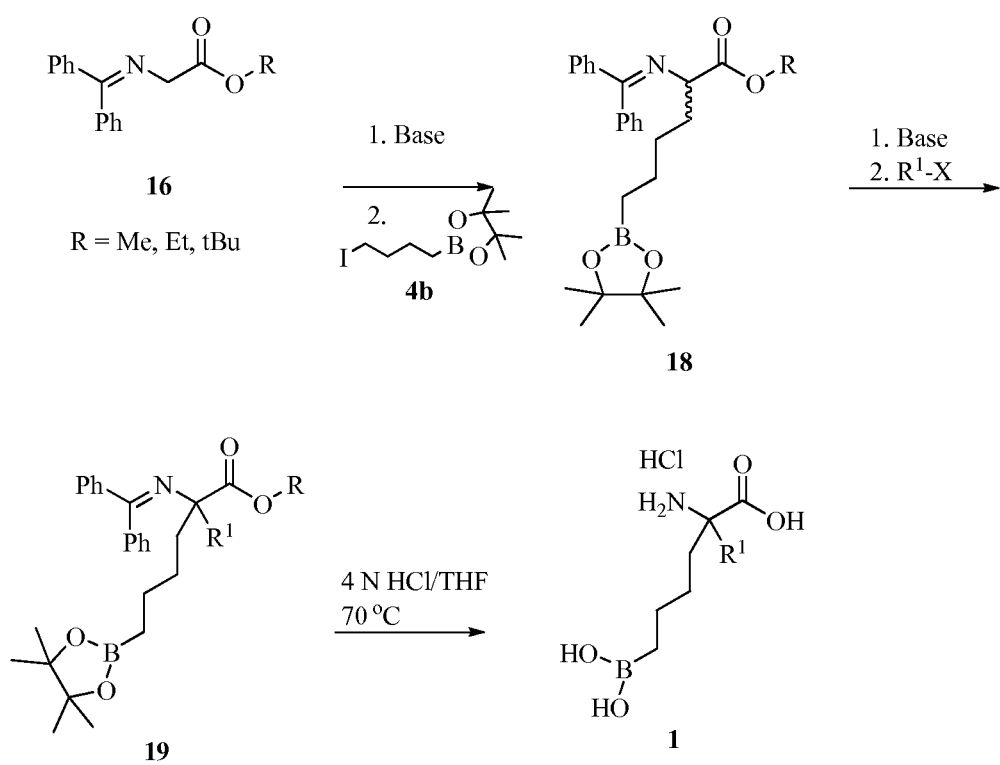

FIG. 7 illustrates a solution-phase synthesis of compound 1 of the present invention where $R^1$ is generated from reagents that are "activated" alkyl halides, such as benzyl bromide. Compound 16 is reacted with LiHMDS at low temperature as described in Reddy et al., Org. Biomol. Chem. 5, 889 (2007), and then 1 equivalent of reagent 4b is added and allowed to react at room temperature for several hours to give intermediate compound 18. The second side chain is introduced by treating compound 18 with a strong base such as n-BuLi, LDA, or the preferred base KHMDS under anhydrous conditions at low temperature and then adding another alkyl halide, such as benzyl bromide, resulting in compound 19. Compound 19 is globally deprotected by treating with strong aqueous acid to give compound 1 (wherein $R^1$ may be of a number of sidechains as described herein).

Figure 8:
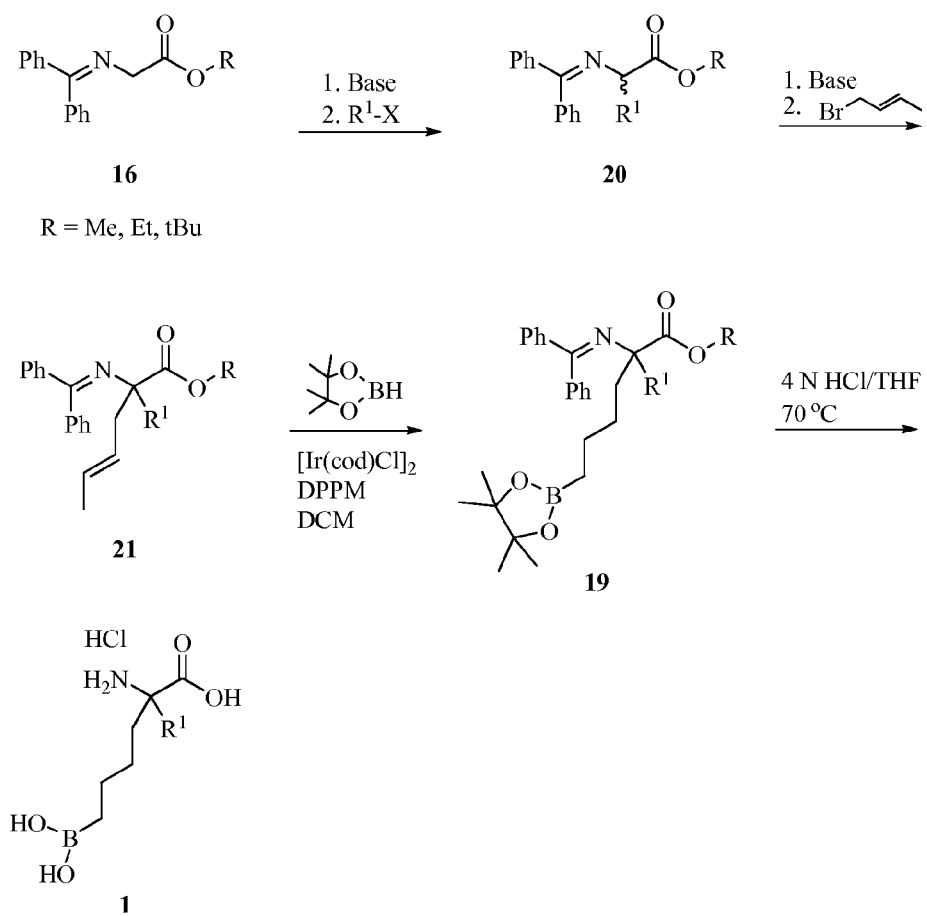

FIG. 8 outlines an exemplary solution-phase synthesis of compound 1 of the present invention, where $R^1$ is generated from a variety of alkyl halides including poorly reactive reagents. Compound 16 is reacted with LiHMDS at low temperature as described in Reddy et al., Org. Biomol. Chem. 5, 889 (2007), and then 1 equivalent of $R^1$—X (wherein $R^1$ may be of a number of sidechains as described herein) is added and allowed to react at room temperature for several hours to give compound 20. The second side chain ($R^1$) can be introduced by treating intermediate compound 20 with a strong base such as n-BuLi, LDA, or the preferred base KHMDS under anhydrous conditions at low temperature and then adding 1 equivalent of crotyl bromide to give compound 21. Hydroboration of the crotyl side chain to give the boronate ester side chain is accomplished by treatment with pinacol borane in the presence of iridium catalyst similar to that reported by Yamamoto et al., Tetrahedron 60, 10695 (2004), to give compound 19, which is globally deprotected by treating with strong aqueous acid to give compound 1.

Figure 9:
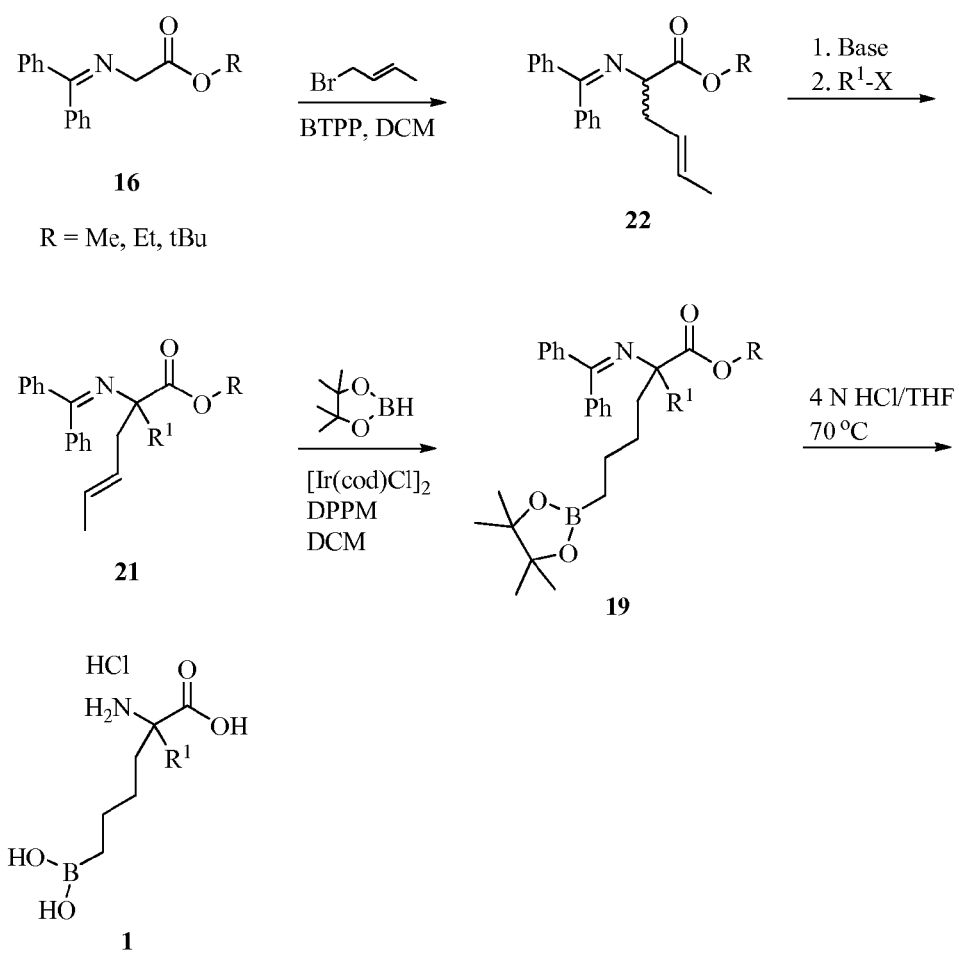

FIG. 9 illustrates an exemplary solution-phase synthesis of compound 1 of the present invention, where $R^1$ is generated from a set of alkyl halides such as α-haloacetate esters. Functionalities of this type provide intermediates with multiple sites of alkylation for the next reaction. Therefore, introduction of the crotyl side chain first is preferred for this compound class. Compound 16 is treated with 1.5 eq of BTPP (or BEMP) and crotyl bromide at room temperature for several hours, O'Donnell, J. Acc. Chem. Res. 37, 506 (2004) to give compound 22. The $R^1$ side chain can be introduced by treating compound 22 with a strong base such as n-BuLi, LDA, or the preferred base KHMDS under anhydrous conditions at low temperature and then adding 1 equivalent of $R^1$—X to give compound 21. Hydroboration of the crotyl side chain to give the boronate ester side chain is accomplished by treatment with pinacol borane in the presence of iridium catalyst similar to that reported by Yamamoto et al., Tetrahedron 60, 10695 (2004), to give compound 19, which is globally deprotected by treating with strong aqueous acid to give compound 1 (wherein $R^1$ may be of a number of sidechains as described herein).

Figure 10:
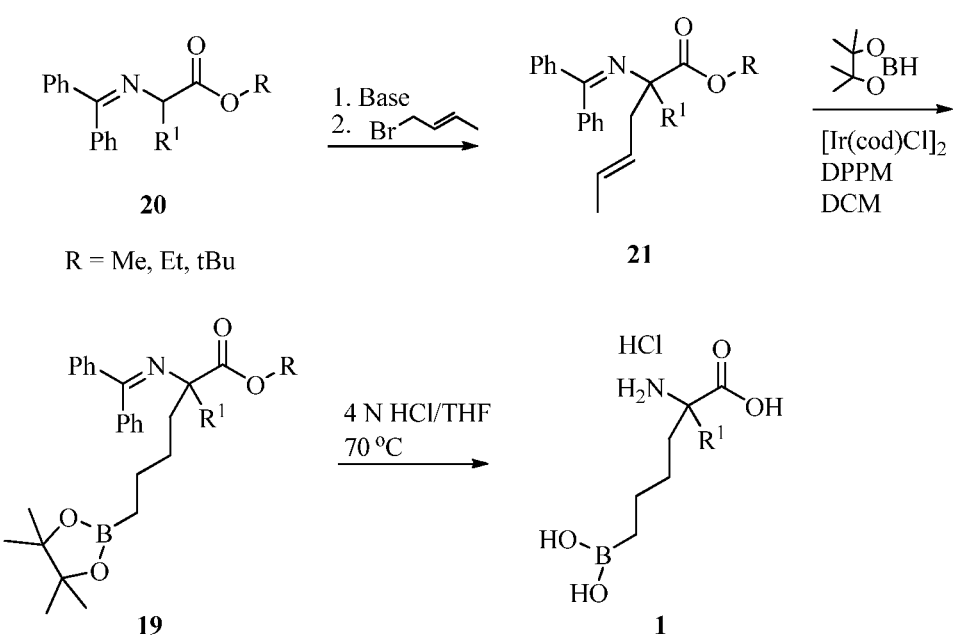

FIG. 10 outlines an exemplary solution-phase synthesis of compound 1 of the present invention where $R^1$ is generated from commercially available amino acids or esters such as L-leucine-tert-butyl ester HCl. Compound 20 is prepared from these commercially available amino esters as described in FIG. 6. The second side chain ($R^1$) can be introduced by treating compound 20 with a strong base such as n-BuLi, LDA, or the preferred base KHMDS under anhydrous conditions at low temperature and then adding 1 equivalent of crotyl bromide to give intermediate compound 21. Hydroboration of the crotyl side chain to give the boronate ester side chain is accomplished by treatment with pinacol borane in the presence of iridium catalyst similar to that reported by Yamamoto et al., Tetrahedron 60, 10695 (2004), to give compound 19, which is globally deprotected by treating with strong aqueous acid to give compound 1 (wherein $R^1$ may be of a number of sidechains as described herein).

Figure 11:
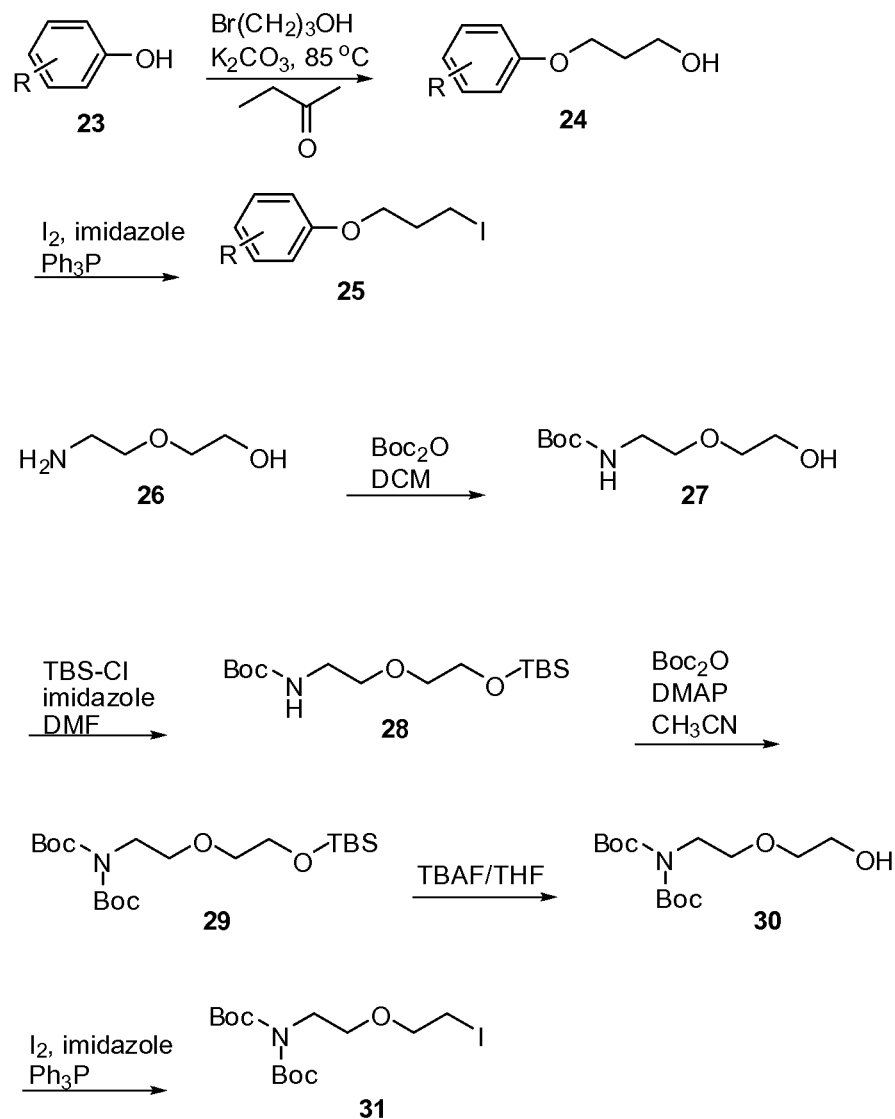

It should be noted that many $R^1$—X reagents used in the synthetic chemistry of FIGS. 3-10 are not commercially available. In such cases, they were made, for example, by the exemplary reactions outlined in FIG. 11, among other methods. For example, although FIG. 11 illustrates the use of a phenol starting material, the synthesis could be readily adapted to other similar starting materials, such as piperidine, piperazine, and morpholine compounds. Likewise, compound 27 could also be any of a variety of homologous compounds.

Referring to the top of FIG. 11, compound 25 is prepared by reacting substituted or unsubstituted phenols with 3-bromo-1-propanol in the presence of a base, such as potassium carbonate, at elevated temperature for several hours. Upon isolation of product 25, it is converted to the alkyl iodide by reaction with iodine in the presence of imidazole and triphenylphosphine. Alternatively, resin-bound triphenylphosphine can also be used to give compound 25 that can be used in various alkylation steps as $R^1$—X in accordance with the methods hereof.

As illustrated at the bottom of FIG. 11, amine-containing $R^1$ side chains can be introduced into compound 1 by preparing $R^1$—X alkylating reagents such as compound 31 by first reacting starting material 26 with di-tert-butyl dicarbonate to give compound 27, which is subsequently O-protected by treating it with TBS-Cl and imidazole to give di-protected intermediate 28. The base labile carbamate is further protected by another treatment with di-tert-butyl dicarbonate in the presence of dimethylaminopyridine to give tri-protected intermediate 29. The TBS ether is removed by treating with fluoride ion in organic solvent to give alcohol 30. Finally, alkyl iodide 31 is prepared in analogous manner as described above for the synthesis of compound 25.

Figure 12:
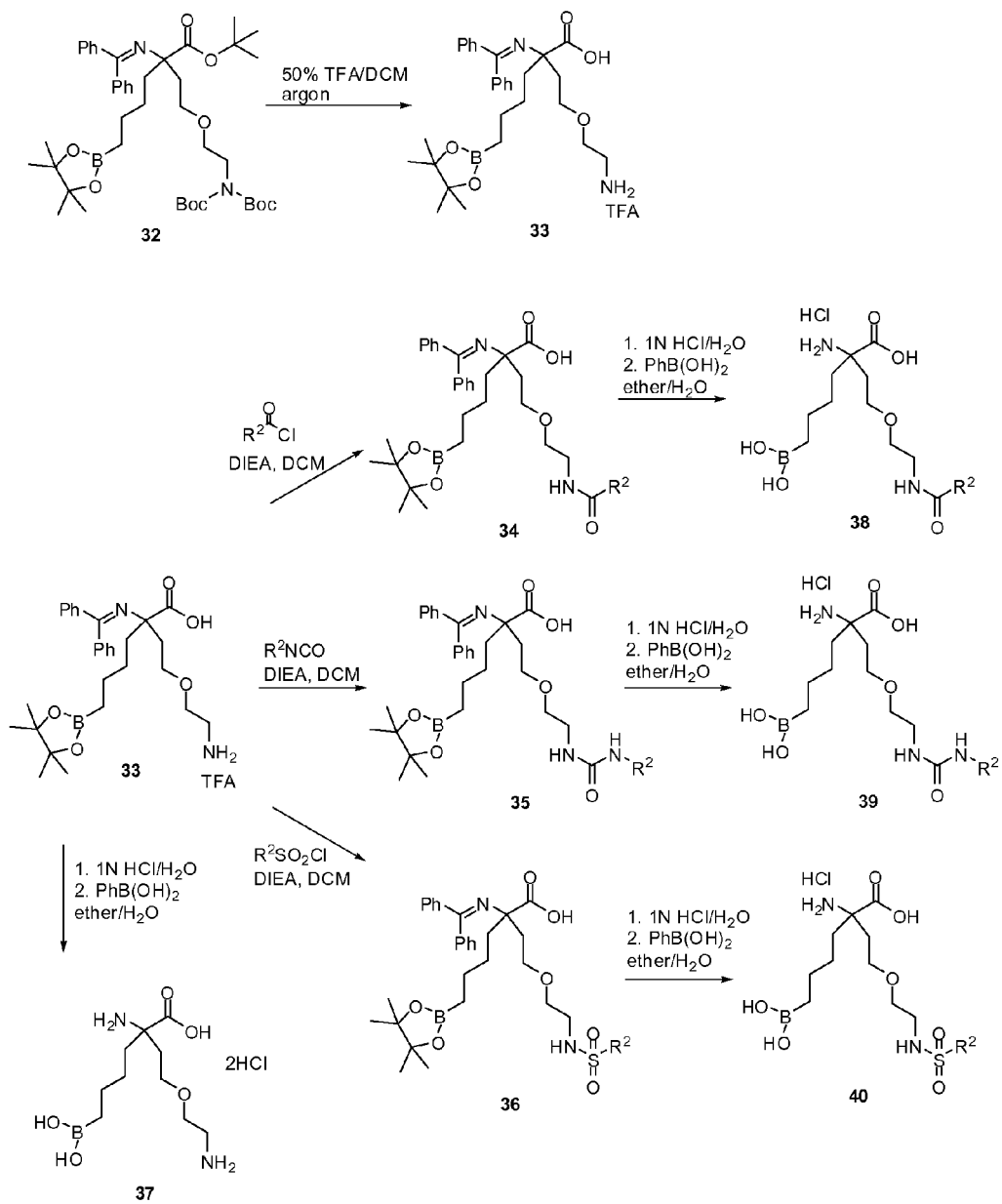

FIG. 12 outlines the synthesis of exemplary compounds 38, 39, and 40 of the present invention where the $R^1$ sidechain is made by selective chemistry performed upon a primary amine and subsequent manipulation of this amine in $R^1$. Referring to the top of FIG. 12, compound 33 is generated by the methods outlined in FIGS. 8 and 11. Anhydrous cleavage of the Boc protecting groups results in the primary amine 33. This primary amine can be capped with acyl groups by reacting with acid chlorides to give compound 34. Alternatively, compound 33 can be reacted with isocyanates in the presence of a tertiary amine to give urea 35. Additionally, compound 33 can be reacted with sulfonyl chlorides in the presence of a tertiary amine to give sulfonamide 36. Each of intermediates 33-36 can be further deprotected by a two-step process involving hydrolysis of the ketimine and then transesterification of the pinacol boronic ester by treating with an excess of phenyl boronic acid in a biphasic mixture to give final products 37-41.

Figure 13:
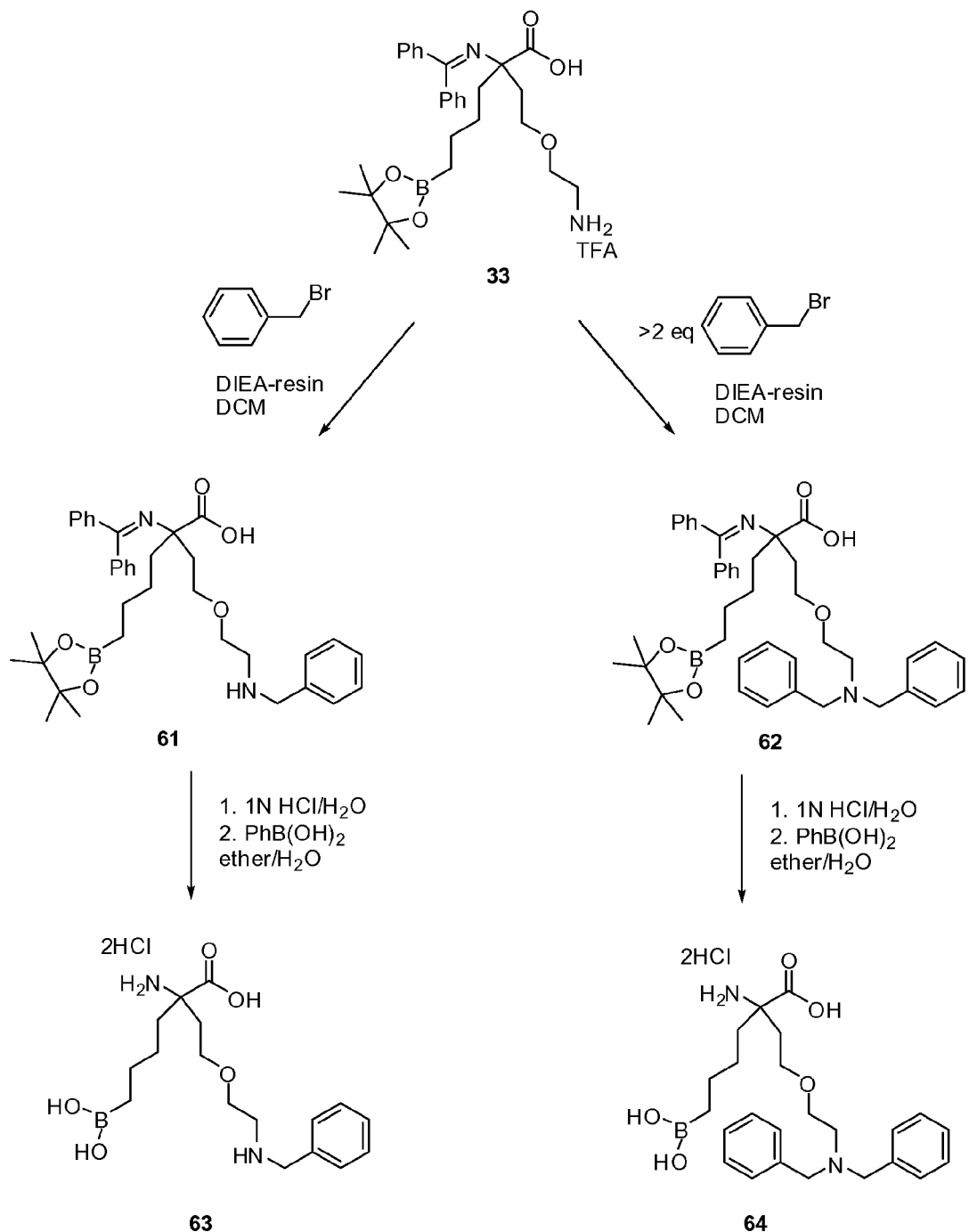

FIG. 13 outlines the synthesis of N-alkylated compounds 63 and 64 in the present invention where $R^1$ includes a primary amine being converted to a secondary or tertiary amine. This methodology can also be used to prepare compounds with side chains containing a cyclic amine such as a piperidine or piperazine and the terminal amine is alkylated similarly. Compound 33 from FIG. 12 can be treated with either one equivalent of an alkyl halide such as benzyl bromide to give compound 61 or alternatively it can be treated with two equivalents of an alkyl halide to give compound 62. Both of these compounds can be deprotected by any of the globally deprotecting procedures to give compounds 63 and 64, respectively, which are derivatives of compound 1. This reaction scheme will also work for alkylating piperidine- and piperazine-containing compounds.

Figure 14:
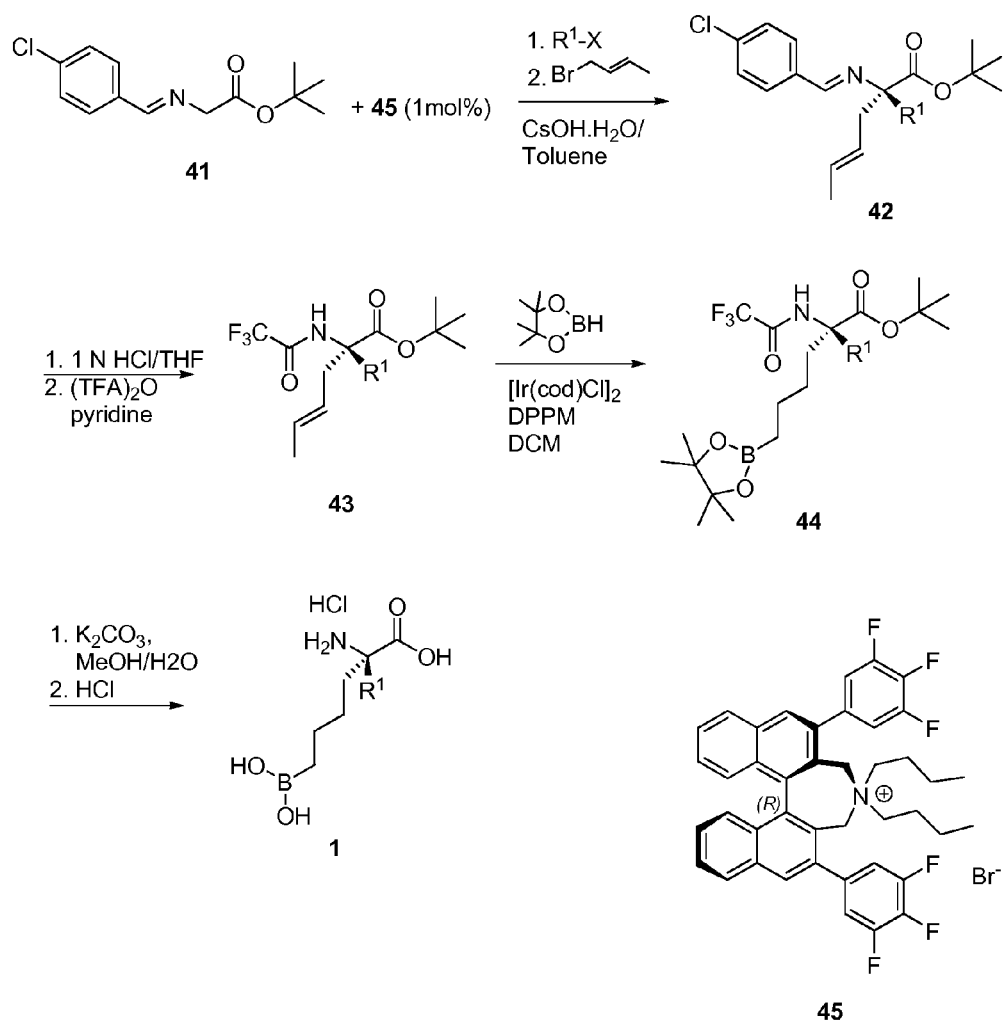

FIG. 14 outlines an exemplary asymmetric synthesis of ABH compound 1 in the present invention where $R^1$ is from a variety of alkyl halides. Compound 41 is asymmetrically alkylated in the presence of 45 under phase transfer conditions resulting in 42 with the desired chirality in high % ee (enantiomeric excess) of >95%. See, Ooi et al., J. Am. Chem. Soc. 122, 5228 (2000); and Jiang et al., Org. Proc. Res. Dev. 12, 1164 (2008). Conversion of imine 42 to acetate 43 results in an intermediate that can be hydroborated under conditions illustrated in FIG. 8. Compound 1 with the desired chirality is then produced by deprotection of all of the masking functionalities. Alternatively, chiral compound 1 can be prepared by separating any disubstituted intermediate by chiral chromatography.

Figure 15:
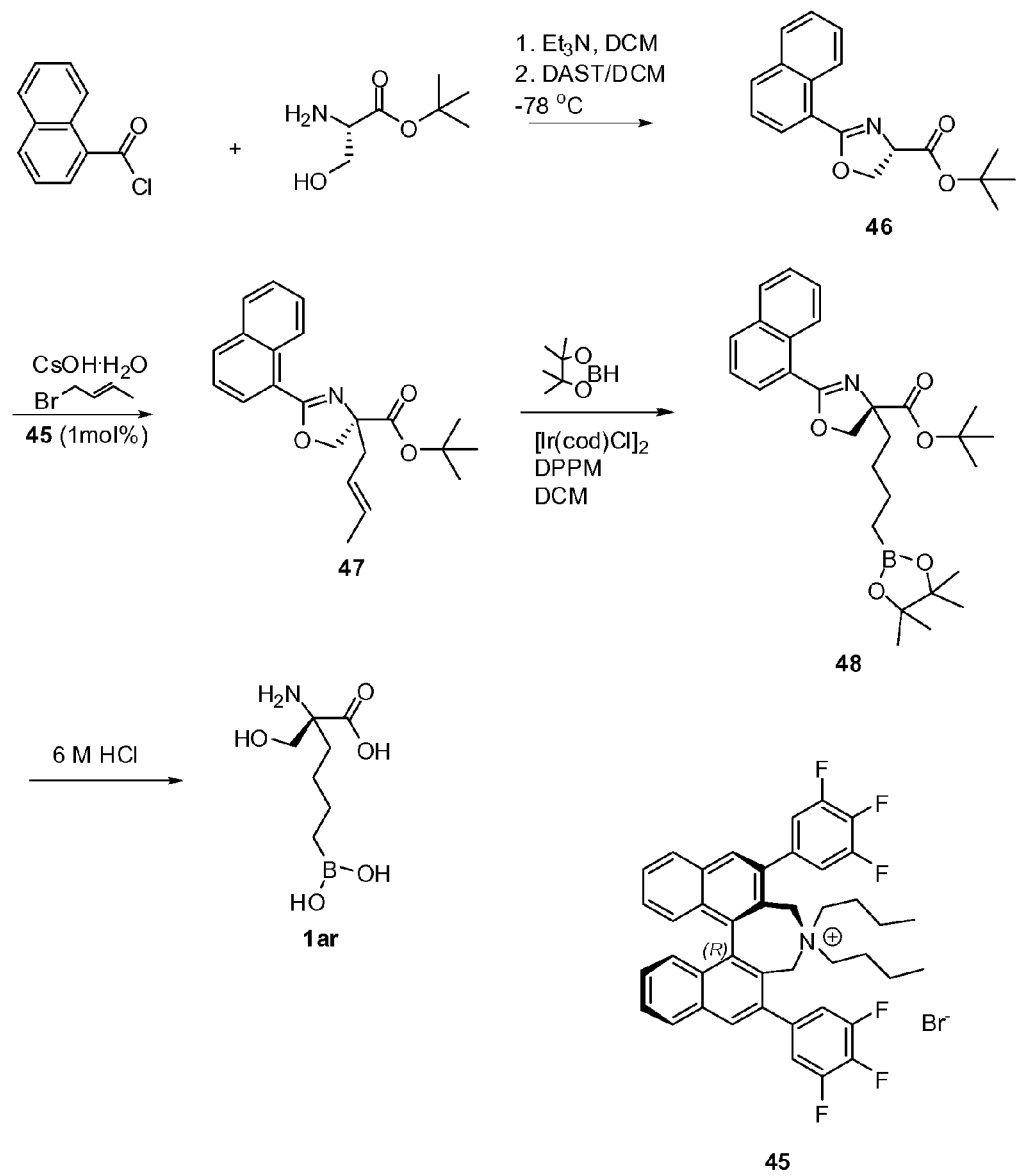

FIG. 15 illustrates an exemplary asymmetric synthesis of compound 1ar where R side chain is specifically a $CH_2OH$ group. Oxazoline 46 is prepared by acylating a serine derivative with an aryl acid chloride such as 2-naphthoic acid chloride, and then dehydrating the intermediate with DAST ((diethylamino)sulfur trifluoride). Compound 46 is alkylated by treating with crotyl bromide in the presence of a base, such as CsOH, to give chiral intermediate 47. This intermediate can be analyzed by chiral chromatography to ascertain the amount of enantiomeric enrichment. Boronic ester 48 is introduced by the hydroboration process described above and the final product is isolated by strong acid cleavage of the protecting groups. Alternatively, the racemic analog of compound 47 can be obtained by reaction of a strong base such as BTPP in the absence of chiral catalyst 45. The desired enantiomer thereafter is be obtained by chiral chromatography.

Figure 16:
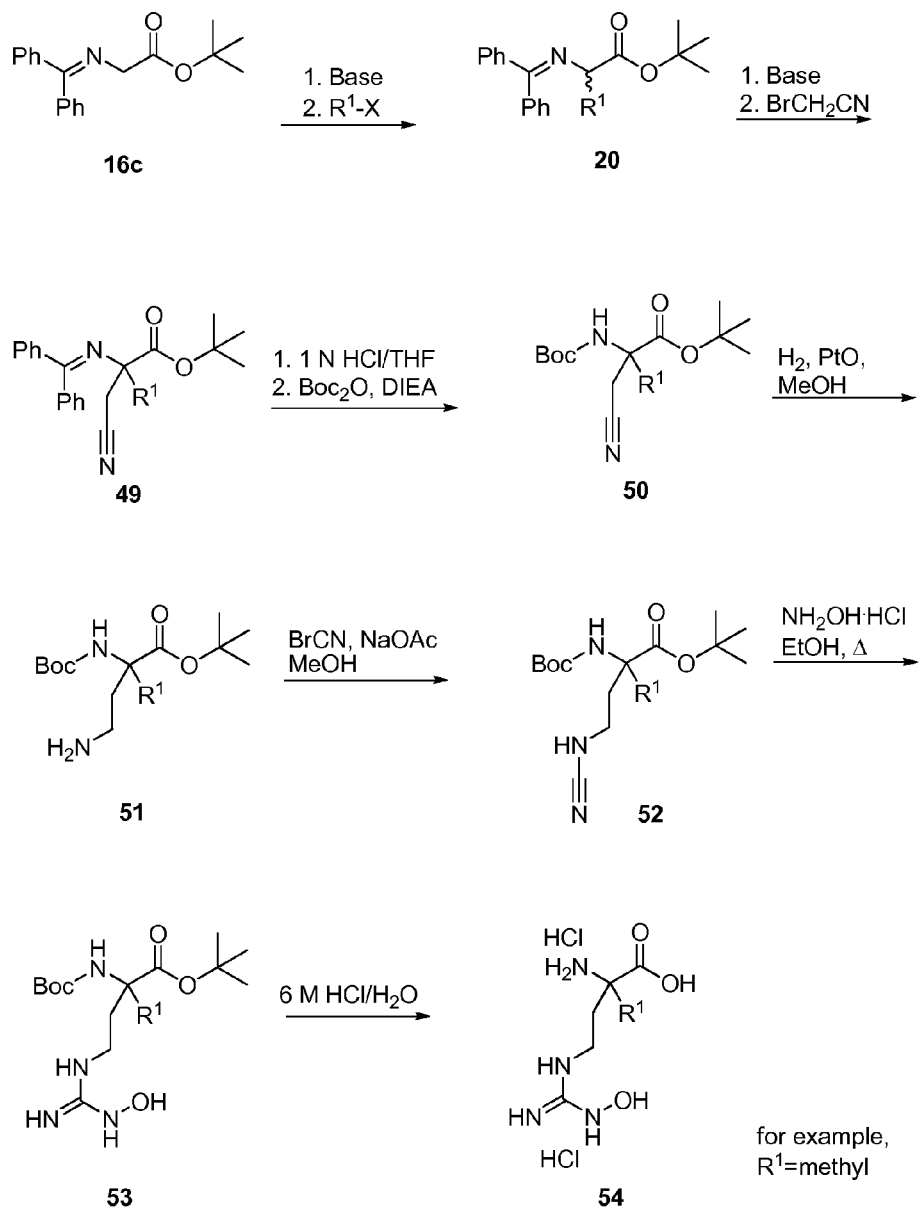

FIG. 16 outlines the synthesis of norNOHA compounds 47 in the present invention where $R^1$ is from a variety of alkyl halides. Starting material 16c is preferred to avoid lactam formation during the synthesis of these compounds. Compound 16c is treated with a base, e.g., LiHMDS, at low temperature under an argon atmosphere and the 1 equivalent of $R^1$—X is added to give compound 20. This is subsequently treated with a strong base such as n-BuLi, LDA, or the preferred base KHMDS under anhydrous conditions at low temperature and then adding 1 equivalent of α-bromoacetonitrile to give 49. The amine is deprotected and reprotected with a Boc group to give intermediate 50. The nitrile is reduced by catalytic hydrogenation using $PtO_2$, Xue et al., J. Org. Chem. 60, 946 (1995), to give the primary amine 51. This primary amine is transformed into the N-hydroxy guanidine group by the series of synthetic steps of cyanamide formation and reaction with hydroxylamine as reported by Custot et. al., J. Am. Chem. Soc. 119, 4086 (1997). Deprotection to final product 54 proceeds by treatment with $HCl/H_2O$.

Figure 17:
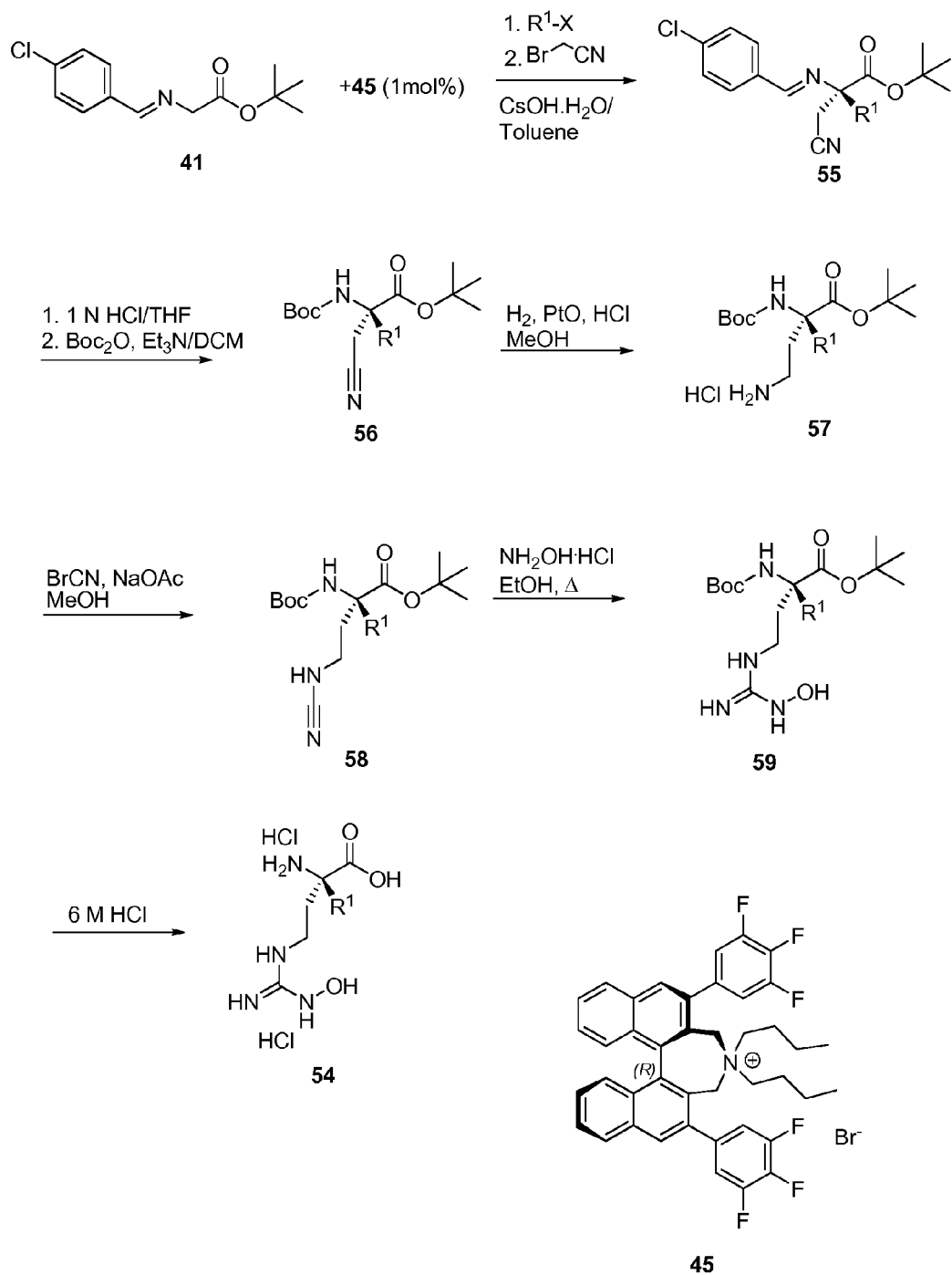

FIG. 17 outlines the asymmetric synthesis of nor-NOHA compound 54 in the present invention where $R^1$ is from a variety of alkyl halides. Compound 41 is asymmetrically alkylated in the presence of catalyst 45 under phase transfer conditions resulting in compound 55 with the desired chirality in high % ee (>95%). See, Ooi et al., J. Am. Chem. Soc. 122, 5228 (2000); and Jiang et al., Org. Proc. Res. Dev. 12, 1164 (2008). Amine 55 is deprotected and reprotected with a Boc group to give compound 56. Nitrile 56 is reduced by catalytic hydrogenation using $PtO_2$, (Xue et al., J. Org. Chem. 60, 946 (1995) to give primary amine 57. The primary amine is transformed into the N-hydroxy guanidine group by the series of synthetic steps of cyanamide formation and reaction with hydroxylamine as reported by Custot et. al., J. Am. Chem. Soc. 119, 4086 (1997). Deprotection to the final product 54 with the desired chirality proceeds by treatment with strong acid to cleave the Boc group.

Some examples of suitable $R^1$ groups are presented in FIGS. 19-24 in the attached drawings. Using the synthetic chemistry methodology discussed herein above, the arginase inhibitors of the present invention having these and other $R^1$ sidechains made be readily prepared in accordance with these principles.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

The compounds of this invention contain chiral centers, providing for various stereoisomeric forms such as diastereomeric mixtures, enantiomeric mixtures as well as optical isomers. The individual optical isomers can be prepared directly through asymmetric or stereospecific synthesis or by conventional chiral separation of optical isomers from the enantiomeric mixture.

Some of the compounds of the present invention may contain chiral centers (beyond the Cα) and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, N Y, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula Ia or formula Ib. "Prodrug," as used herein, means a compound which is convertible in vivo by metabolic means (e.g., by hydrolysis) to a compound of formula Ia or formula Ib. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975).

Further, the compounds of formula IA or formula IB may exist in unsolvated as well as in solvated forms with pharmaceutically acceptable solvents such as water, ethanol, and the like. In general, the solvated forms are considered equivalent to the unsolvated forms for the purpose of the present invention.

EXAMPLES

Compounds of the invention can be prepared by one or more of the following general methods. All parts and percentages are by weight, unless otherwise stated. When ranges are used herein for physical properties, such as molecular weight, or chemical properties, such as chemical formulae, all combinations and subcombinations of such ranges therein are intended to be included as specific embodiments hereof. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions. So that these synthetic methods may be more fully understood, some examples of solid-phase and solution-phase protocols for making specific compounds are also presented. All of the starting materials are commercially available or may prepared by procedures described in these schemes or by procedures that would be well known to one of ordinary skill in organic chemistry.

General Procedure A. Preparation of Amino Ester Ketimine from Amino Ester Hydrochloride Referring to FIG. 6 in the attached drawings, glycine ethyl ester hydrochloride 14b (2.015 g, 14.4 mmol) was suspended in 25 mL dry DCM (dichloromethane) and benzophenone imine (2.42 mL, 14.4 mmol) was added and stirred at room temperature for 8-16 hr. The reaction mixture was filtered, washed with 5 mL DCM and the organic solution was washed 1× with $H_2O$ and 1× with brine (a saturated aqueous solution of sodium chloride). The DCM was dried by filtering over a bed of Hydromatrix brand diatomaceous earth and concentrating to dryness in vacuo. The product 16b, an oil (2.83 g, 74%), was used without further purification. MS (LC/MS, ESI): 268 (M+H). $^1$H NMR (300 MHz, $CDCl_3$, δ): 7.5-8.0 (m, 10H), 4.5 (s, 2H), 4.0 (q, 2H), 1.2 (t, 3H). See, O'Donnell et al., J. Org. Chem. 47, 2663 (1982).

Although this synthesis is described with reference to the ethyl ester, the corresponding methyl and tert-butyl esters, as illustrated in FIG. 6, may also be made by adapting this procedure.

General Procedure B. Alkylation of Glycine Ketimine with Unactivated Alkyl Halides Referring to FIG. 7, compound 16 (1 mmol) was dissolved in 5 mL dry THF (tetrahydrofuran) under argon and cooled to −78° C. A 1 M solution of base, LiHMDS (lithium hexamethyldisilazane), in THF (1.05 mL) was added to the reaction mixture and stirred at −78° C. for 45 minutes, and then an alkyl halide such as compound 4b (1.05 mmol) in 3 mL dry THF was added. The reaction mixture was stirred at −78° C. for 30 minutes and then allowed to warm to room temperature and stirred for 8-18 hr. The desired product (compound 18) was isolated by diluting the reaction mixture with 20 mL EtOAc (ethyl acetate) and washing this organic solution with water and then brine. The organic solution was dried by filtering over a bed of Hydromatrix brand diatomaceous earth and concentrating to dryness. This residue was dissolved in a small amount of DCM, applied to a dry silica gel column, and eluting with mixtures of EtOAc/hexane (1-5%).

General Procedure C. Alkylation of Amino Ester Ketimine with Alkyl Halides

Still referring to FIG. 7, compound 18 (1 mmol) was dissolved in 5 mL dry THF under argon and cooled to −78° C. A 0.5 M solution of KHMDS (potassium hexamethyldisilazane) in toluene (1.05 mL) was added to the reaction mixture and stirred at −78° C. for 45 minutes, and then the alkyl halide $R^1$—X (1.05 mmol), such as benzyl bromide, in 3 mL dry THF was added. The reaction mixture was stirred at −78° C. for 30 minutes and then allowed to warm to room temperature and stirred for 8-18 hr. The desired product (compound 19) was isolated by diluting the reaction mixture with 20 mL EtOAc and washing this organic solution with water and then brine. The organic solution was dried by filtering over a bed of Hydromatrix brand diatomaceous earth and concentrating to dryness. This residue was dissolved in a small amount of DCM, applied to a dry silica gel column, and eluting with mixtures of EtOAc/hexane (1-5%).

General Procedure D. Alkylation of Glycine Ketimine with Activated Alkyl Halides Referring to FIG. 9, compound 16 (1 mmol) was dissolved in 5 mL dry DCM under argon. Crotyl bromide (1.5 mmol) and BTPP (tert-butylimino-tri(pyrrolidino)-phosphorane, 1.5 mmol) were added to the reaction mixture and stirred at room temperature for 4-18 hr. The desired product (compound 22) was purified by concentrating the reaction mixture to a puddle, redissolving in a small amount of DCM, applying it to a dry silica gel column, and eluting with mixtures of EtOAc/hexane (0.5-2%).

General Procedure E. Hydroboration of Crotyl Sidechain

Still referring to FIG. 9, under an argon atmosphere [Ir(cod)Cl]$_2$ (34 mg, 0.05 mmol, 5 mol %) and DPPM (bis(diphenylphosphino)methane, 38 mg, 0.10 mmol, 10 mol %) were dissolved in 5 mL dry DCM. Pinacol borane (175 μL, 1.20 mmol) and compound 21 (1 mmol) were dissolved in 5 mL dry DCM and added. The reaction mixture was stirred at room temp for 24 hr. The reaction was quenched by adding 1 mL of MeOH/H$_2$O (1:1), concentrating the reaction mixture in vacuo, diluting the reaction mixture with 20 mL EtOAc, and washing this organic solution with water and then brine. The organic solution was dried by filtering over a bed of Hydromatrix brand diatomaceous earth and concentrating it to dryness. This residue was dissolved in a small amount of DCM, applied to a dry silica gel column, and eluted with mixtures of EtOAc/hexane (5-10%) to give pure compound 19.

General Procedure F. Global Deprotection Procedure for Removal of Nitrogen Protecting Groups Still referring to FIG. 9 (also illustrated in FIG. 7), compound 19 was dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product was eluted with 2 N NH$_4$OH. The basic solution was concentrated in vacuo to dryness, and the residue was dissolved in 10 mL 1 N HCl and lyophilized to produce purified compound 1.

General Procedure G. Alternative Deprotection Procedure

An alternative method for removing the imine protecting group is exemplified in FIG. 12. According to this procedure, compound 33 was dissolved in 1 N HCl and stirred at room temperature for 2 hr. To this reaction mixture was added 10 equivalents of phenyl boronic acid and diethyl ether. The reaction mixture was rapidly stirred at room temperature for 12-18 hr. The layers were separated and the aqueous solution was washed 2× with diethyl ether. The aqueous solution was concentrated in vacuo to dryness and the residue dissolved in 1 N HCl and lyophilized to produce purified amine 37.

General Procedure H. Synthesis of Aryl Ether Alkyl Iodides 25

Referring to FIG. 11, phenol 23 (3.0 mmol) and 3-bromo-1-propanol (3.75 mmol) were dissolved in 15 mL of 2-butanone. Solid K$_2$CO$_3$ (6.0 mmol) was added and the reaction stirred at reflux for 18-24 hr. The mixture was allowed to cool to room temperature and diluted with EtOAc, washed 3× with water and 1× with brine. The organic solution was dried over magnesium sulfate and concentrated in vacuo to give oil 24. Product compound 24 was assayed by LC/MS and $^1$H NMR, and it used without further purification.

Still referring to FIG. 11, imidazole (6.0 mmol) and triphenylphosphine (3.3 mmol) were dissolved in 15 mL DCM and cooled to 0° C. under argon. Iodine (3.3 mmol) was added to this mixture and stirred for 10-15 minutes. Alkyl alcohol 24 was added in 10 mL DCM and the reaction mixture was allowed to warm to room temperature and then stirred for 12-18 hr. A few mL of saturated sodium thiosulfate solution was added along with 10-15 mL water and the mixture was stirred for 10-15 minutes. The mixture was separated and the organic layer washed 3× with water and 1× with brine. The organic solution was dried over magnesium sulfate and concentrated in vacuo to give a solid residue. This residue was dissolved in a small amount of DCM, applied to a dry silica gel column, and eluted with mixtures of EtOAc/hexane (5-10%) to give purified compound 25. This compound is useful as an alkylating reagent in accordance with the synthesis methods described herein.

The foregoing reaction also was performed using resin-bound triphenylphosphine in slight molar excess in a similar procedure. In this case, these products 25 were normally used without purification over silica gel.

General Procedure I. Synthesis of Boc-Protected Amino Alkyl Iodides 31

Referring to FIG. 11, amino alcohol 26 was Boc-protected by treating it with 1.1 equivalents of di-tert-butyl dicarbonate in DCM at room temperature for 2-4 hr. The mixture was washed 2× with 1 N HCl and 1× with brine. The organic solution was dried over magnesium sulfate and concentrated in vacuo to give compound 27, which was used without further purification.

Still referring to FIG. 11, compound 27 was treated with 2.5 equivalents imidazole and 1.1 equivalents of tert-butyl (chloro)dimethylsilane in DMF (N,N-dimethyl-formamide) at room temperature for 12-18 hr. The reaction mixture was diluted with EtOAc and this organic mixture was washed 3× with water and 1× with brine. The organic solution was dried over magnesium sulfate and concentrated in vacuo to give di-protected compound 28, which was used without further purification.

Next, compound 28 was treated with 2 equivalents of di-tert-butyl dicarbonate and 0.2 equivalents of dimethylaminopyridine in acetonitrile while stirring at room temperature for 36-48 hr. The reaction mixture was concentrated to dryness and the residue dissolved in EtOAc. This solution was washed 3× with 0.1 N HCl and 1× with brine, dried over magnesium sulfate, filtered, and concentrated in vacuo to give compound 29 which was used without further purification.

Subsequently, compound 29 was treated with 1.5 equivalents TBAF (tetrabutylammonium fluoride) in THF under argon at room temperature for 3-5 hr. This mixture was diluted with EtOAc and washed 3× with water and 1× with brine. The organic solution was dried over magnesium sulfate and concentrated in vacuo to give di-Boc compound 30, which was used without further purification.

Finally, imidazole (6.0 mmol) and triphenylphosphine (3.3 mmol) were dissolved in 15 mL DCM and cooled to 0° C. under argon. Iodine (3.3 mmol) was added to this mixture and stirred for 10-15 minutes. Alkyl alcohol 30 was added in 10 mL DCM and the reaction mixture was allowed to warm to room temperature and then stirred for 12-18 hr. A few mL of saturated sodium thiosulfate solution was added along with 10-15 mL water and the mixture was stirred for 10-15 minutes. The mixture was separated and the organic layer washed 3× with water and 1× with brine. The organic solution was dried over magnesium sulfate and concentrated in vacuo to give compound 31. This residue was dissolved in a small amount of DCM, applied to a dry silica gel column, and eluted with mixtures of EtOAc/hexane (5-10%) to give purified compound 31. This compound is useful as an alkylating reagent in accordance with the synthesis methods described herein.

General Procedure J. Selective Boc Removal and Acylation of Resulting Primary Amine Referring to FIG. 12, compound 32 is converted to compound 33 by treatment with 25-50% TFA (trifluoroacetic acid)/DCM under argon for 12-16 hr. The reaction mixture is concentrated to dryness in vacuo, a few mL of DCM added and this solution is reconcentrated to dryness and then the residue dried in vacuo for several hr and then placed under an argon atmosphere.

Still referring to FIG. 12, this residue was added to 2-3 equivalents of a resin-bound amine base such as PS-DIEA (diisopropylethylamine) in DCM. To this was added 1 eq. of an acylating agent, such as acetic anhydride or benzoyl chloride, and the reaction mixture stirred or shaken for 12-16 hr. The reaction mixture was filtered and the resin washed with a few mL of DCM then a few mL of 1 N HCl/THF (1:2). The filtrates were combined and additional 1 N HCl added. This mixture was stirred vigorously at room temperature for 12-16 hr and the organic layer separated from the aqueous layer. The aqueous solution was washed 2× with ethyl acetate. The pinacol ester was removed by General Procedure G as described above and the resulting crude products (compounds 38, 39, and 40) were purified by elution over a $C_{18}$ column with acetonitrile/water gradients with 0.075% TFA.

General Procedure K. Preparation of Amino Ester Ketimine from α-Bromo Acetate

Referring to FIG. 6, benzophenone imine (6.68 mL, 40.0 mmol) and tert-butyl bromoacetate 15c (5.9 mL, 40.0 mmol) were dissolved in 40 mL acetonitrile. DIEA (6.95 mL, 40.0 mmol) was added and the reaction mixture heated to reflux for 14 hr. The reaction mixture was cooled to room temperature, neutralized by the addition of 50% aqueous acetic acid, and cooled to 0° C. The resulting solids were collected by filtration and then washed with cold ethanol. Product 16c was dried in vacuo to give 9.05 g (77%) which was used without further purification. MS (LC/MS, ESI): 296 (M+H), 240 (M−tBu+H). $^1$H NMR (300 MHz, CDCl$_3$, δ): 7.5-8.0 (m, 10H), 4.5 (s, 2H), 1.4 (s, 9H). See, O'Donnell, Acc. Chem. Res. 37, 506 (2004).

General Procedure L. Preparation of Compound 4a

Referring to FIG. 6, 2-(4-bromobutyl)benzo[d][1,3,2]dioxaborole 17 (5.09 g, 20.0 mmol) was dissolved in 20 mL dry THF, pinacol (2.39 g, 20.1 mmol) was added, and the reaction mixture was stirred at room temperature for 2 hr under argon. The reaction mixture was concentrated in vacuo, 50 mL of hexane was added to the residue, and it was cooled at 0° C. for 2 hr. The solids were filtered and the washed with 25 mL hexane, the filtrate further diluted with 300 mL hexane, and cooled at 0° C. overnight. Again, the solids were filtered and washed with 25 mL hexane, another 300 mL hexane added to the filtrate and cooled at 0° C. for 2 hr. No further solids were formed and this solution was concentrated in vacuo, dried in vacuo, and the resulting clear oil 4a (5.24 g, 99%) was stored under argon at 0° C. $^1$H NMR (300 MHz, CDCl$_3$, δ): 3.5 (t, 2H), 1.8 (m, 2H), 1.4 (m, 2H), 1.2 (s, 12H), 0.7 (t, 2H).

General Procedure M. Preparation of Compound 4b

Still referring to FIG. 6, compound 4a (5.0 g, 19.0 mmol) was dissolved in 40 mL dry acetone, sodium iodide (4.65 g, 31.0 mmol) was added and the reaction mixture was stirred overnight at room temperature under argon. The resulting solids were filtered and washed with diethyl ether. The filtrate was concentrated to a viscous oil which was diluted with 150 mL diethyl ether, washed 2× with H$_2$O and 1× with brine, dried over sodium sulfate and concentrated in vacuo to a clear colorless oil 4b (5.86 g, 99%). $^1$H NMR (300 MHz, CDCl$_3$, δ): 3.1 (t, 2H), 1.8 (m, 2H), 1.4 (m, 2H), 1.2 (s, 12H), 0.7 (t, 2H).

Example 1. 2-Amino-2-benzyl-6-boronohexanoic acid hydrochloride (1a)

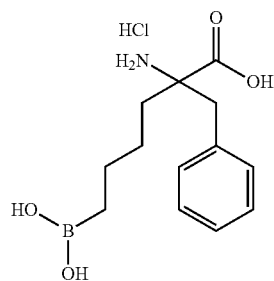

Compound 1a, illustrated above, was synthesized via the reaction scheme illustrated in FIG. 3 (wherein R$^1$ is benzyl). Residual free hydroxyl groups on Fmoc-Gly-Wang resin 2 were acetylated by treating 5.0 g (0.85 mmol/g, 4.25 mmol) of resin 2 with acetic anhydride (1.0 mL, 10.6 mmol) and DMAP (4-dimethylaminopyridine, 100 mg, 0.82 mmol) in 50 mL of NMP (N-methyl-2-pyrrolidone) for 1 hr. The resin was filtered, washed 3× with DCM, 3× with alternating MeOH (methanol) and DCM, 3× with MeOH, then 4× with DCM. This resin was then treated with 75 mL 20% piperidine/DMF for 30 minutes followed by filtration and washing the resin as described above. The resin-bound amine was converted to the ketimine 3 by treating with benzophenone imine (8.6 mL, 51.2 mmol) and glacial acetic acid (2.2 mL, 38.4 mmol) in 60 mL NMP overnight followed by filtration and washing the resin as described above.

Still referring to FIG. 3, resin 3 was treated with a mixture of compound 4a (11.2 g, 42.6 mmol, 10 eq), TBAI (tetrabutylammonium iodide, 15.7 g, 42.5 mmol, 10 eq) and BTPP (13.0 mL, 42.5 mmol, 10 eq) in 45 mL of NMP overnight followed by filtration and washing the resin as described above to give resin 5, which was dried in vacuo to give 5.39 g. Subsequently, 305 mg of resin 5 (0.60 mmol/g, 0.18 mmol) was washed with 4×5 mL of dry THF under an argon atmosphere. 3.5 mL of dry THF was added to this resin followed by KHMDS in toluene (0.5 M, 1.8 mL, 0.90 mmol) and gently mixed at room temperature for 45 min. The reaction mixture was quickly filtered under an argon atmosphere and benzyl bromide (214 µL, 1.8 mmol) in 5 mL dry THF was added and gently mixed for 24 hr. This reaction mixture was filtered, washed 3×THF/H$_2$O 2:1, 3×THF, 3×DCM, 3× alternating MeOH and DCM, and 4×DCM to give compound 6, wherein R$^1$ is benzyl.

Still referring to FIG. 3, resin 6 was washed 3×THF/H$_2$O 2:1, and then it was treated with 1 N HCl/THF 1:2 for 4 hr at room temperature followed by washing 3×THF/H$_2$O 2:1, 3×THF, and 4×DCM. This resin was immediately treated with 95% TFA/H$_2$O for 2 hr and the filtrate was collected, and the resin washed with TFA and DCM. The washes were combined with the reaction filtrate and concentrated in vacuo. This residue was immediately dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product was eluted with 2 N NH$_4$OH. The basic solution was concentrated in vacuo to dryness and the residue was dissolved in 10 mL 1 N HCl and lyophilized to give 44 mg of compound 1a, the chemical structure of which is illustrated above. MS (LC/MS, ESI): 248 (M–H$_2$O+H). $^1$H NMR (300 MHz, D$_2$O, δ): 7.25-7.5 (m, 5H), 2.9-3.1 (m, 2H), 1.9 (t, 2H), 1.4-1.6 (m, 4H), 0.7 (t, 2H).

Example 2. 2-Allyl-2-amino-6-boronohexanoic acid hydrochloride (1b)

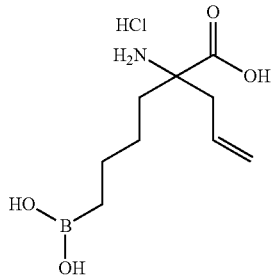

1b

Referring again to FIG. 3 (wherein R$^1$ is allyl), 300 mg of resin 5 (0.60 mmol/g, 0.18 mmol) was washed with 4×5 mL of dry THF under an argon atmosphere. 3.5 mL of dry THF was added to this resin followed by KHMDS in toluene (0.5 M, 1.8 mL, 0.90 mmol) and gently mixed at room temperature for 45 min. The reaction mixture was quickly filtered under an argon atmosphere and the alkylating agent, allyl bromide (155 µL, 1.8 mmol) in 5 mL dry THF, was added and gently mixed for 24 hr. This reaction mixture was filtered, washed 3×THF/H$_2$O 2:1, 3×THF, 3×DCM, 3× alternating MeOH and DCM, and 4×DCM to give resin 6, wherein R$^1$ is allyl.

Still referring to FIG. 3, resin 6 was washed 3×THF/H$_2$O 2:1, and then treated with 1 N HCl/THF 1:2 for 4 hr at room temperature followed by washing 3×THF/H$_2$O 2:1, 3× THF, and 4×DCM. This resin was immediately treated with 95% TFA/H$_2$O for 2 hr and the filtrate was collected, the resin washed with TFA and DCM. The washes were combined with the reaction filtrate and concentrated in vacuo. This residue was immediately dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product was eluted with 2 N NH$_4$OH. The basic solution was concentrated in vacuo to dryness and the residue was dissolved in 10 mL 1 N HCl and lyophilized to give 11 mg of compound Ib, the chemical structure of which is illustrated above. MS (LC/MS, ESI): 198 (M–H$_2$O+H). $^1$H NMR (300 MHz, D$_2$O, δ): 5.7-5.8 (m, 1H), 5.0-5.1 (m, 2H), 2.3-2.5 (m, 2H), 1.9 (t, 2H), 1.4-1.6 (m, 4H), 0.7 (t, 2H).

Example 3. 2-Amino-2-(4-boronobutyl)succinic acid hydrochloride (1c)

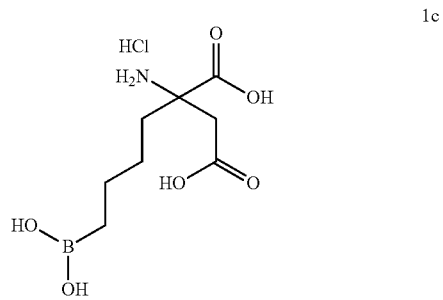 [SMILES: NC(CCCCB(O)O)(CC(=O)O)C(=O)O ; Cl]

1c

Referring again to FIG. 3 (wherein R$^1$=carboxymethyl), 300 mg of resin 5 (0.60 mmol/g, 0.18 mmol) was washed with 4×5 mL of dry THF under an argon atmosphere. 3.5 mL of dry THF was added to this resin followed by KHMDS in toluene (0.5 M, 1.8 mL, 0.90 mmol) and gently mixed at room temperature for 45 min. The reaction mixture was quickly filtered under an argon atmosphere and allyl bromide (265 µL, 1.8 mmol) in 5 mL dry THF was added and gently mixed for 24 hr. This reaction mixture was filtered, washed 3×THF/H$_2$O 2:1, 3×THF, 3×DCM, 3× alternating MeOH and DCM, and 4×DCM to give resin 6.

Still referring to FIG. 3, resin 6 was washed 3×THF/H$_2$O 2:1, and then treated with 1 N HCl/THF 1:2 for 4 hr at room temperature followed by washing 3×THF/H$_2$O 2:1, 3×THF, and 4×DCM. This resin was immediately treated with 95% TFA/H$_2$O for 2 hr and the filtrate was collected, the resin washed with TFA and DCM. The washes were combined with the reaction filtrate and concentrated in vacuo. This residue was immediately dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product was eluted with 2 N NH$_4$OH. The basic solution was concentrated in vacuo to dryness and the residue was dissolved in 10 mL 1 N HCl and lyophilized to give 24 mg of compound 1c, the chemical structure of which is illustrated above. MS (LC/MS, ESI): 216 (M–H$_2$O+H). $^1$H NMR (300 MHz, D$_2$O, δ): 2.5-2.7 (m, 2H), 1.9 (t, 2H), 1.4-1.6 (m, 4H), 0.7 (t, 2H).

Example 4a. Solid-Phase Synthesis of 2-Amino-6-(borono-2-(3-phenoxypropyl)hexanoic acid hydrochloride (1d)

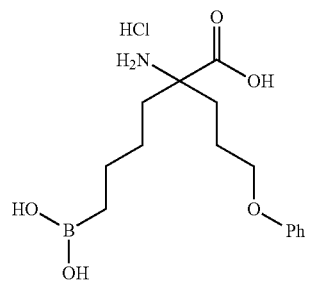

1d

Compound 1d, depicted above, was synthesized from resin 3 as illustrated in FIG. 4. Resin 3 (502 mg, 0.33 mmol) was treated with 3-phenoxypropyl bromide (0.525 µL, 3.3 mmol), TBAI (1.23 g, 3.3 mmol), and BTPP (1.01 mL, 3.3 mmol) in 5 mL NMP at room temperature for 24 hr. The resin was filtered, washed 3× with DCM, 3× with alternating MeOH and DCM, 3× with MeOH, then 4× with DCM to give resin 7. This was further washed 3× THF/H$_2$O 2:1, and then treated with 1 N HCl/THF 1:2 for 4 hr at room temperature followed by washing 3×THF/H$_2$O (2:1), 3×THF, and 4×DCM. The resulting hydrochloride salt was neutralized by treating the resin with 10% DIEA/DCM for 5 minutes and resin 8 was washed 3× with DCM, 3× with alternating MeOH and DCM, 3× with MeOH, then 4× with DCM.

Still referring to FIG. 4, 3,4-dichlorobenzaldehyde (0.87 g, 5.0 mmol) was dissolved in 6 mL of trimethylorthoformate/NMP (2:1), added to resin 8, and mixed overnight. The resin was filtered and washed 3×DCM, 3× alternating MeOH and DCM, 3× with DCM to give resin 9. This was further treated with compound 4a (1.02 g, 3.3 mmol) and BTPP (1.01 mL, 3.3 mmol) in 5 mL NMP for 24 hr. This resin was filtered, washed 3× with DCM, 3× with alternating MeOH and DCM, 3× with MeOH, then 4× with DCM to give resin 10.

Next, resin 10 was washed 3×THF/H$_2$O 2:1, and then treated with 1 N HCl/THF 1:2 for 4 hr at room temperature followed by washing 3×THF/H$_2$O 2:1, 3×THF, and 4×DCM. This resin was immediately treated with 95% TFA/H$_2$O for 2 hr and the filtrate was collected, the resin washed with TFA and DCM. The washes were combined with the reaction filtrate and concentrated in vacuo. This residue was immediately dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product, compound 1d, was eluted with 2 N NH$_4$OH. The basic solution was concentrated in vacuo to dryness and the residue was dissolved in 10 mL 1 N HCl and lyophilized to give 23 mg of compound 1d, the chemical structure of which is illustrated above. MS (LC/MS, ESI): 292 (M−H$_2$O+H). $^1$H NMR (300 MHz, D$_2$O, δ): 7.0-7.4 (m, 5H), 3.8 (m, 2H), 1.9 (m, 4H), 1.4-1.6 (m, 6H), 0.7 (t, 2H).

Example 4b. Solution-Phase Synthesis of 2-Amino-6-(borono-2-(3-phenoxypropyl)hexanoic acid hydrochloride (1d)

As an alternative to the solid-phase synthesis of compound 1d described above, it was also be made by the reaction scheme outlined in FIG. 8 (wherein R$^1$=phenoxypropyl).

tert-Butyl 2-(diphenylmethyleneamino)-5-phenoxypentanoate (20d)

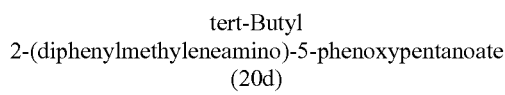

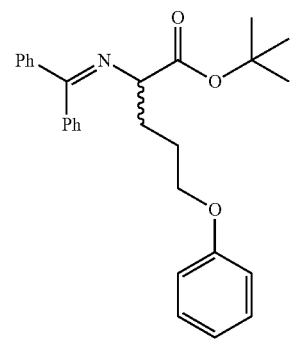

20d

Referring to FIG. 8, compound 20d, 0.60 g (69%), was obtained using General Procedure B, described above. MS (LC/MS, ESI): 430 (M+H), 374 (M−tBu+H). $^1$H NMR (300 MHz, CDCl$_3$, δ): 7.4-8.0 (m, 15H), 4.0 (t, 1H), 3.9 (t, 2H), 2.2 (m, 2H), 1, 8 (m, 2H), 1.4 (s, 9H).

tert-Butyl 2-(diphenylmethyleneamino)-2-(3-phenoxypropyl)hex-4-enoate (21d)

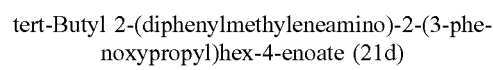

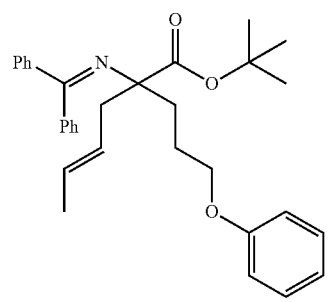

21d

Next, compound 21d, 0.56 g (83%), was obtained using General Procedure C, described above. MS (LC/MS, ESI): 484 (M+H), 428 (M−tBu+H). $^1$H NMR (300 MHz, CDCl$_3$, δ): 7.4-8.2 (m, 15H), 5.4 (m, 2H), 4.3.9 (m, 2H), 2.5-2.7 (m, 2H), 2.1 (m, 2H), 2.0 (d, 3H), 1.4 (s, 9H).

tert-Butyl 2-(diphenylmethyleneamino)-2-(3-phenoxypropyl-6-(4,4,5,5-tetramethyl-1,3,2-dioxaborolane-2-yl)hexanoate (19d)

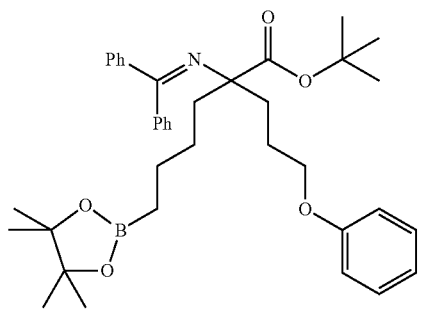

19d

Thereafter, 0.08 g (40%) of 19d was obtained using General Procedure E, described above. MS (LC/MS, ESI): 612 (M+H), 556 (M−tBu+H). $^1$H NMR (300 MHz, CDCl$_3$, δ): 7.4-8.2 (m, 15H), 3.8-4.0 (m, 2H), 3.5 (m, 2H), 2.2 (m, 2H), 1.4-1.8 (m, 4H), 1.5 (s, 9H), 1.2 (s, 12H), 0.8 (t, 2H).

Finally, boronate ester 19d was hydrolyzed to produce 2-amino-6-borono-2-(3-phenoxypropyl)hexanoic acid trifluoroacetate in a method similar to that illustrated in FIG. 8. This compound, 10 mg as a clear glass, was obtained using General Procedure F, with the following modification: The final compound was purified by reverse-phase HPLC on a C$_{18}$ column by eluting with a gradient of acetonitrile/water with 0.075% added TFA. Accordingly, the trifluoroacetic acid salt was isolated (not the hydrochloride). MS (LC/MS, ESI): 292 (M−H$_2$O+H). $^1$H NMR (300 MHz, D$_2$O, δ): 7.3-7.5 (m, 5H), 4.0 (t, 2H), 3.4 (m, 2H), 1.8-1.9 (m, 6H), 1.4-1.6 (m, 4H), 0.7 (t, 2H). The TFA addition salt may be readily converted to the hydrochloride salt, i.e., compound 1d, using conventional acid/base extraction methods.

Examples 5-23

The following compounds listed in Table 1, below, were synthesized in analogous manner as described above for compound 1d. In Table 1, each compound has the following chemical structure (each example in the Table has a different R$^1$ group):

TABLE 1

| Example No. | Compound No. | R$^1$ | Amount Isolated | MS Data | Physical Appearance |
|---|---|---|---|---|---|
| 5 | 1e | ~~~~phenylbutyl~~~~ | 47 mg | 290 | Clear glass |
| 6 | 1f | ~~~~O-C$_6$H$_4$-Cl (para) | 20 mg | 344 | White flocculent powder |
| 7 | 1g | ~~~~O-C$_6$H$_4$-OMe (para) | 20 mg | 340 | White flocculent powder |
| 8 | 1h | ~~~~O-C$_6$H$_4$-F (para) | 50 mg | 328 | White flocculent powder |
| 9 | 1i | ~~~~O-C$_6$H$_4$-NO$_2$ (para) | 16 mg | 355 | Slight tan powder |

TABLE 1-continued
| Example No. | Compound No. | R¹ | Amount Isolated | MS Data | Physical Appearance |
|---|---|---|---|---|---|
| 10 | 1j | 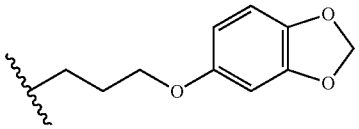 [SMILES: *CCCOc1ccc2c(c1)OCO2] | 12 mg | 354 | Clear glass |
| 11 | 1k | 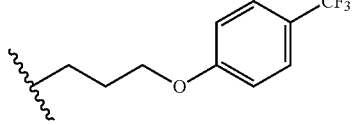 | 8 mg | 378 | White powder |
| 12 | 1l | 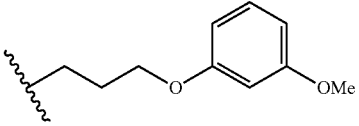 [SMILES: *CCCOc1cccc(OC)c1] | 8 mg | 340 | White powder |
| 13 | 1m | 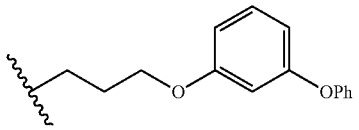 [SMILES: *CCCOc1cccc(Oc2ccccc2)c1] | 19 mg | 402, 384 | Light tan powder |
| 14 | 1n | 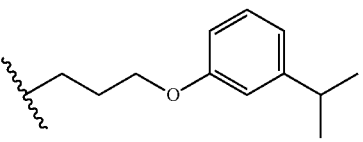 [SMILES: *CCCOc1cccc(C(C)C)c1] | 5 mg | 352, 334 | Clear glass |
| 15 | 1o | 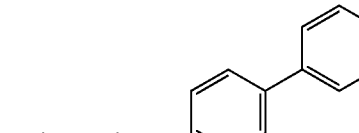 | 8 mg | 386, 368 | Clear glass |
| 16 | 1p | 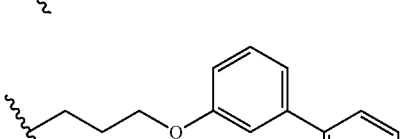 | 18 mg | 386, 368 | Clear glass |
| 17 | 1q | 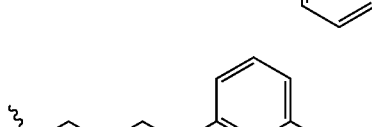 | 23 mg | 379, 360 | Light tan powder |
| 19 | 1s | 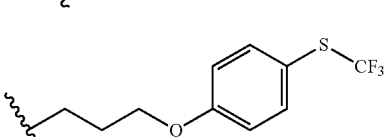 | 2.5 mg | 410, 392 | White powder |
| 21 | 1u | 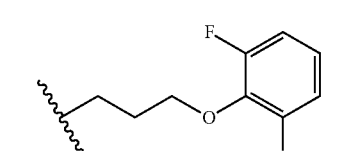 | 12 mg | 346, 238 | White powder |

TABLE 1-continued

| Example No. | Compound No. | R¹ | Amount Isolated | MS Data | Physical Appearance |
|---|---|---|---|---|---|
| 22 | 1v | | 15 mg | 324, 306 | White powder |
| 23 | 1w | | 20 mg | 324, 306 | White powder |

Example 24. 4-(4-Amino-8-borono-4-carboxyoctyloxy)benzoic acid hydrochloride (1x)

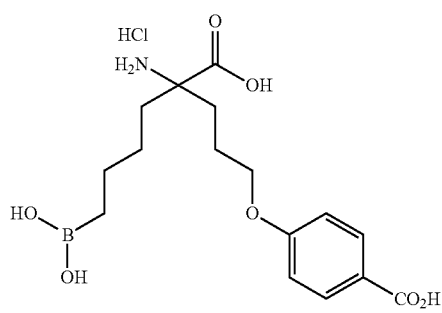

1x

Compound 1x, 100 mg as a clear glass, was synthesized using General Procedure F, described above. MS (LC/MS, ESI): 336 (M–H$_2$O+H), 354 (M+H).

Example 25. 2-Amino-2-(3-(4-aminophenoxypropyl)-6-boronohexanoic acid trifluoroacetate (1y)

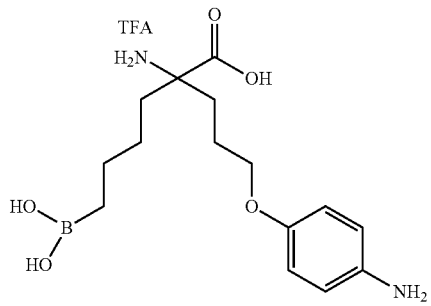

1y

Compound 1y was obtained by treating 150 mg of compound 19i, illustrated below, with HOAc/H2O/THF (1:1:1) for 1 hr. Next, 90 mg of the intermediate was subjected to catalytic transfer hydrogenation (to reduce the nitro group to an amino group) in methanol with 25 mg 10% Pd/C and 0.6 g ammonium formate at room temperature for 15 minutes.

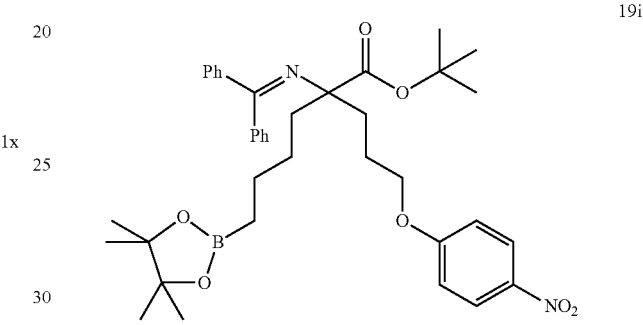

19i

The catalyst was filtered and the solution concentrated to dryness in vacuo to give a residue that was subjected to 6 N HCl at 70° C. for 5 hr. This reaction mixture was concentrated to dryness and compound 1y was eluted on a C$_{18}$ column with an acetonitrile/water gradient with 0.075% TFA present. After lyophilization of the fractions, 27 mg of compound 1y was obtained as a light tan powder. MS (LC/MS, ESI): 307 (M–H$_2$O+H), 325 (M+H).

Example 26. 2-Amino-6-(borono-2-(pyridin-3-ylmethyl)hexanoic acid hydrochloride (1z)

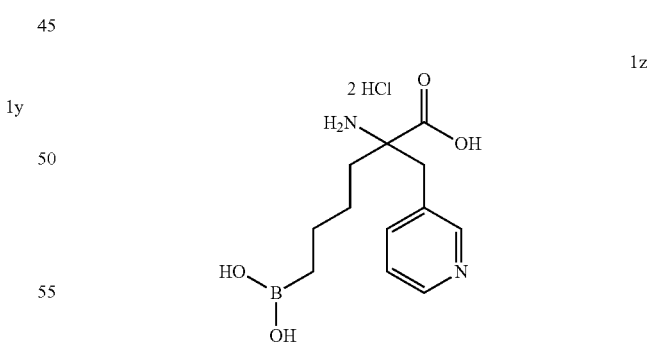

1z

Compound 1z was synthesized from resin 5 as illustrated in FIG. 5 (wherein R¹=pyridylmethyl). Resin 5 (0.504 g, 0.30 mmol) was washed 3×THF/H$_2$O 2:1, and then treated with 1 N HCl/THF 1:2 for 4 hr at room temperature followed by washing 3×THF/H$_2$O (2:1), 3×THF, and 4×DCM. The resulting hydrochloride salt was neutralized by treating the resin with 10% DIEA/DCM for 5 min and resin 11 was washed 3× with DCM, 3× with alternating MeOH and DCM, 3× with MeOH, and then 4× with DCM.

Next, 3,4-dichlorobenzaldehyde (0.71 g, 4.1 mmol) was dissolved in 6 mL of trimethylorthoformate/NMP (2:1), and it was added to resin 11 and mixed overnight. The resin was filtered and washed 3×DCM, 3× alternating MeOH and DCM, 3× with DCM to give resin 12, as illustrated in FIG. 5. This was further treated with 3-(bromomethyl)pyridine hydrobromide (0.152 g, 0.60 mmol) and BTPP (0.36 mL, 1.20 mmol) in 5 mL NMP for 24 hr. This resin was filtered, washed 3× with DCM, 3× with alternating MeOH and DCM, 3× with MeOH, then 4× with DCM to give resin 13.

Still referring to FIG. 5, resin 13 was washed 3×THF/H$_2$O 2:1, and then treated with 1 N HCl/THF 1:2 for 4 hr at room temperature followed by washing 3×THF/H$_2$O 2:1, 3×THF, and 4×DCM. This resin was immediately treated with 95% TFA/H$_2$O for 2 hr and the filtrate was collected, the resin washed with TFA and DCM. The washes were combined with the reaction filtrate and concentrated in vacuo. This residue was immediately dissolved in 6 N HCl/THF 2:1 and stirred overnight at 70° C. This reaction mixture was cooled and extracted 3× with EtOAc. The aqueous layer was concentrated to a puddle and redissolved in 5 mL 1 N HCl and filtered over a plug of Dowex 50WX8 ion exchange resin in the acidic form. This plug was washed with H$_2$O and then the desired product was eluted with 2 N NH$_4$OH. The basic solution was concentrated in vacuo to dryness and the residue was dissolved in 10 mL 1 N HCl and lyophilized to give 50 mg of compound 1z. MS (LC/MS, ESI): 249 (M−H$_2$O+H); 231 (M−2H$_2$O+H). $^1$H NMR (300 MHz, D$_2$O, δ): 8.65 (d, 2H), 8.6 (s, 1H), 8.4 (d, 1H), 8.0 (m, 1H), 3.2-3.5 (m, 2H), 1.9 (m, 4H), 1.4-1.6 (m, 6H), 0.7 (t, 2H).

Example 27.
2-Amino-2-(benzyloxyethyl)-6-boronohexanoic acid hydrochloride (1aa)

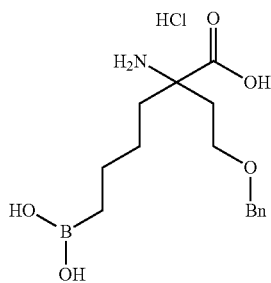

1aa

Compound 1aa, illustrated above, was synthesized by the following procedure.

tert-Butyl 3-(benzyloxy)-2-(diphenylmethyleneamino)butanoate (20aa)

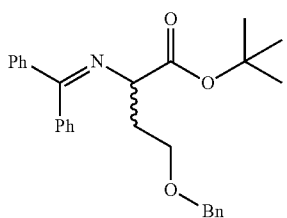

20aa

Compound 20aa, 0.37 g (86%), was obtained using General Procedure B, described above. MS (LC/MS, ESI): 430 (M+H), 374 (M−tBu+H). $^1$H NMR (300 MHz, CDCl$_3$, δ): 7.4-8.0 (m, 15H), 4.6 (m, 2H), 3.9 (t, 1H), 3.4 (t, 2H), 2.2 (m, 2H), 1.4 (s, 9H).

tert-Butyl 2-(benzyloxyethyl)-2-(diphenylmethyleneamino)hex-4-enoate (21aa)

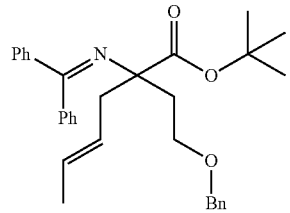

21aa

Compound 21aa, 0.37 g (80%), was obtained using General Procedure C, described above. MS (LC/MS, ESI): 484 (M+H), 428 (M−tBu+H). $^1$H NMR (300 MHz, CDCl$_3$, δ): 7.4-8.2 (m, 15H), 5.4 (m, 2H), 4.7 (m, 2H), 3.4 (t, 2H), 2.5-2.8 (m, 2H), 2.1 (m, 2H), 2.0 (d, 3H), 1.4 (s, 9H).

tert-Butyl 2-(benzyloxyethyl)-2-(diphenylmethyleneamino)-6-(4,4,5,5-tetramethyl-1,3,2-dioxaborolane-2-yl)hexanoate (19aa)

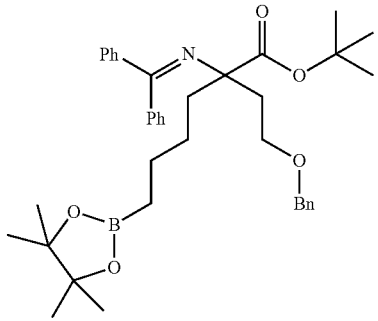

19aa

Compound 19aa, 0.23 g (47%), was obtained using General Procedure E, described above. MS (LC/MS, ESI): 612 (M+H), 556 (M−tBu+H). $^1$H NMR (300 MHz, CDCl$_3$, δ): 7.4-8.2 (m, 15H), 4.7 (m, 2H), 3.8-4.0 (m, 2H), 3.4 (t, 2H), 2.2 (m, 2H), 1.4-1.8 (m, 4H), 1.5 (s, 9H), 1.2 (s, 12H), 0.8 (t, 2H).

Finally, compound 1aa, the structure of which is illustrated above, 68 mg (53%), was obtained using General Procedure F, described above. MS (LC/MS, ESI): 292 (M−H$_2$O+H). $^1$H NMR (300 MHz, D$_2$O, δ): 7.3-7.5 (m, 5H), 4.5 (s, 2H), 3.4 (m, 2H), 1.8-1.9 (m, 4H), 1.4-1.6 (m, 4H), 0.7 (t, 2H).

Examples 28-35

The following compounds listed in Table 2, below, were synthesized in analogous manner as described above for compound 1aa. In Table 2, each compound has the following chemical structure (each example in the Table has a different R$^1$ group):

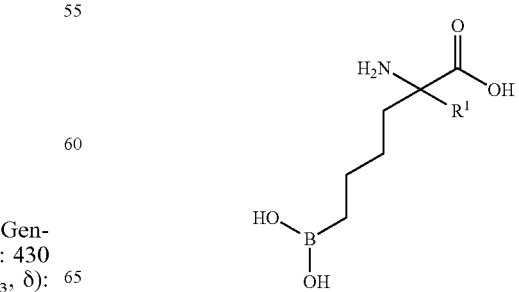

TABLE 2

| Example No. | Compound No. | R¹ | Amount Isolated | MS Data | Physical Appearance |
|---|---|---|---|---|---|
| 28 | 1ab | ![structure] | 100 mg | 234, 216 | Clear glass |
| 29 | 1ac | ![structure] | 19 mg | 310, 292 | Clear glass |
| 30 | 1ad | ![structure] | 70 mg | 330, 312 | Light tan powder |
| 31 | 1ae | ![structure] | 30 mg | 354, 336 | Light tan powder |
| 32 | 1af | ![structure] | 8 mg | 324, 306 | Clear glass |
| 33 | 1ag | ![structure] | 31 mg | 326, 308 | Clear glass |
| 34 | 1ah | ![structure] | 9 mg | 341, 323 | Light yellow powder |
| 35 | 1ai | ![structure] | 12 mg | 445, 427 | Clear glass |

Example 36. 2-Amino-2-(2-(3-aminophenoxy)ethyl)-6-boronohexanoic acid hydrochloride (1aj)

Compound 19aj (88 mg), illustrated below, was dissolved in 3 mL THF and 20 mg of 10% Pd/C was added followed introducing a $H_2$ atmosphere over the reaction mixture.

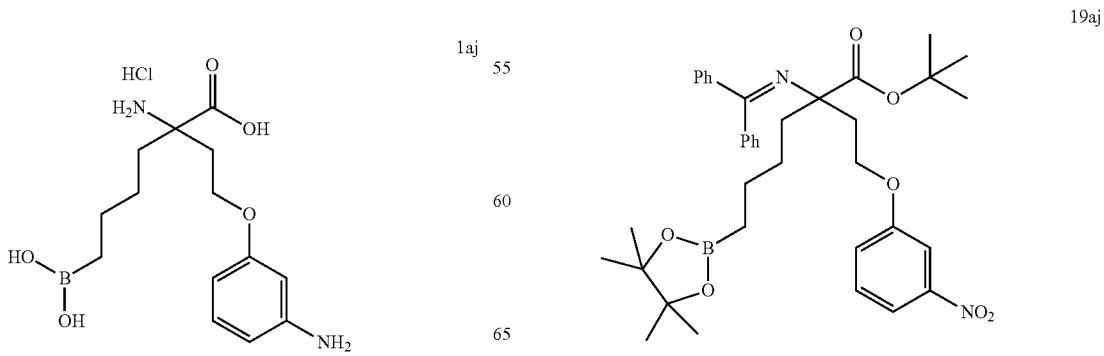

This was stirred at room temperature for 4 hr. The hydrogenation reaction reduced the imine to a secondary amine and the nitro group to an amino group. The reaction mixture was filtered over Celite brand diatomaceous earth and the solvent removed in vacuo. The residue was redissolved in THF with 0.5 mL of 1 N HCl added and placed in a Parr hydrogenation apparatus with 50 mg of 10% Pd/C. 50 psi of $H_2$ gas was introduced and the reaction mixture was vigorously shaken for 18 hr. The reaction mixture was again filtered over Celite brand diatomaceous earth and the solvent concentrated in vacuo and the residue was dissolved in 6 M HCl with heating for 4 hr to give 20 mg of compound 1aj as a light tan solid. MS (LC/MS, ESI): 293 (M–$H_2$O+H) 311 (M+H).

Example 37.
2-Amino-6-borono-2-(3-hydroxypropyl)hexanoic acid hydrochloride (1ak)

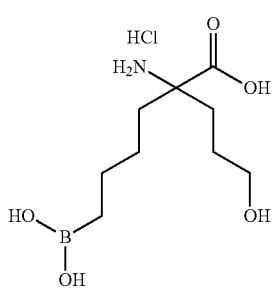

1ak

Compound 1ak, illustrated above, was synthesized by the following procedure.

tert-Butyl 3-(benzyloxy)-2-(diphenylmethyleneamino)-5-(tetrahydro-2H-pyran-2-yloxy)pentanoate (20ak)

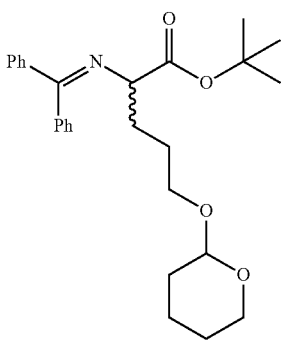

20ak

Compound 20ak, 0.44 g (50%), was obtained using General Procedure B, described above. MS (LC/MS, ESI): 438 (M+H), 382 (M–tBu+H). $^1$H NMR (300 MHz, CDCl$_3$, δ): 7.4-8.0 (m, 10H), 4.9 (m, 1H), 4.0 (m, 1H), 3.8 (m, 2H), 3.4 (m, 2H), 2.1 (m, 2H), 1.3-2.0 (m, 8H), 1.4 (s, 9H).

tert-Butyl 2-(diphenylmethyleneamino)-2-(3-(tetrahydro-2H-pyran-2-yloxy)propylhex-4-enoate (21ak)

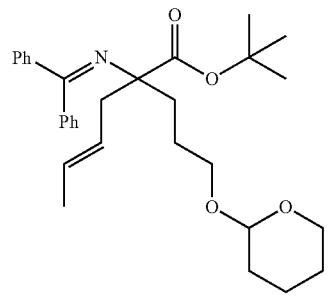

21ak

Compound 21ak, 0.44 g (90%), was obtained using General Procedure C, described above. MS (LC/MS, ESI): 492 (M+H), 436 (M–tBu+H). $^1$H NMR (300 MHz, CDCl$_3$, δ): 7.4-8.2 (m, 10H), 5.4 (m, 2H), 4.9 (m, 1H), 3.4-3.8 (m, 4H), 2.2-2.5 (m, 2H), 2.0 (d, 3H), 1.4 (s, 9H), 1.3-2.0 (m, 8H).

tert-Butyl 2-(diphenylmethyleneamino)-2-(3-tetrahydro-2H-pyran-2-yloxy(propyl)-6-(4,4,5,5-tetramethyl-1,3,2-dioxaborolane-2-yl)hexanoate (19ak)

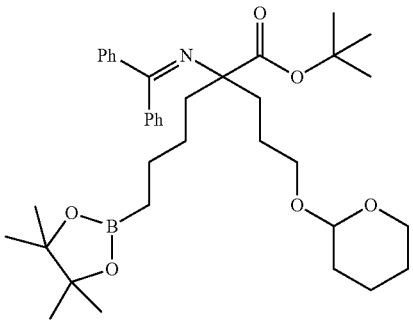

19ak

Compound 19ak, 0.32 g (58%), was obtained using General Procedure E, described above. MS (LC/MS, ESI): 620 (M+H), 564 (M–tBu+H). $^1$H NMR (300 MHz, CDCl$_3$, δ): 7.4-8.2 (m, 10H), 4.9 (m, 1H) 4.4 (m, 2H), 3.5-4.0 (m, 4H), 2.2 (m, 2H), 1.4-1.8 (m, 4H), 1.5 (s, 9H), 1.3-2.0 (m, 8H). 1.2 (s, 12H), 0.8 (t, 2H).

Finally, 75 mg (54%) of compound 1ak, the structure of which is illustrated above, was obtained using General Procedure F, described above. MS (LC/MS, ESI): 216 (M–$H_2$O+H). $^1$H NMR (300 MHz, D$_2$O, δ): 3.6 (m, 2H), 2.0 (m, 2H) 1.4-1.8 (m, 8H), 0.8 (t, 2H).

Example 38.
2-Amino-6-borono-2-(4-boronobutyl)hexanoic acid (1al)

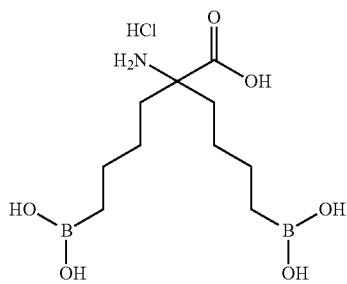

Compound 1al, illustrated above, was synthesized by the following procedure.

tert-Butyl 2-(diphenylmethyleneamino)-6-(4,4,5,5-tetramethyl-1,3,2-dioxaborolan-2-yl)hexanoate (20al)

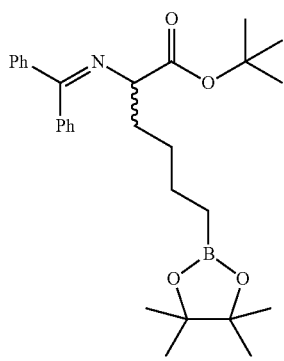

Compound 18al, 0.66 g (69%), was obtained using General Procedure B, described above. MS (LC/MS, ESI): 478 (M+H), 422 (M−tBu+H). $^1$H NMR (300 MHz, CDCl$_3$, δ): 7.4-8.0 (m, 10H), 4.0 (m, 1H), 2.0 (m, 2H), 1.4 (s, 9H), 1.3-1.7 (m, 4H), 1.2 (s, 12H), 0.9 (t, 2H).

tert-Butyl 2-(diphenylmethyleneamino)-2-(4,4,5,5-tetramethyl-1,3,2-dioxaborolan-2-yl)butyl)hex-4-enoate (21al)

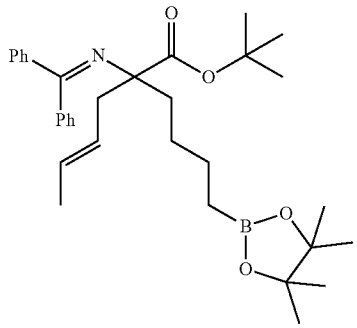

Compound 21al, 0.36 g (49%), was obtained using General Procedure C, described above. MS (LC/MS, ESI): 532 (M+H), 476 (M−tBu+H). $^1$H NMR (300 MHz, CDCl$_3$, δ): 7.4-8.2 (m, 10H), 5.4 (m, 2H), 2.5-2.8 (m, 2H), 2.0-2.1 (m, 2H), 2.0 (d, 3H), 1.3-1.7 (m, 4H), 1.4 (s, 9H), 1.2 (s, 12H), 0.9 (t, 2H).

tert-Butyl-2-(diphenylmethyleneamino)-6-(4,4,5,5-tetramethyl-1,3,2-dioxaborolan-2-yl)-2-(4,4,5,5-tetramethyl-1,3,2-dioxaborolan-2-yl)butyl)hexanoate (19al)

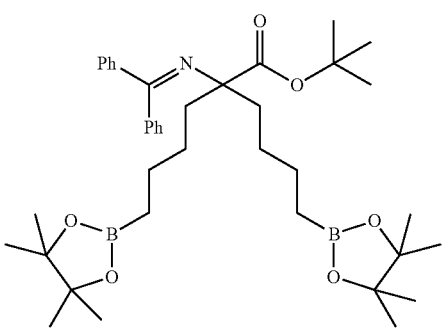

Compound 19al, 75 mg (34%), was obtained using General Procedure E, described above. MS (LC/MS, ESI): 660 (M+H), 604 (M−tBu+H). $^1$H NMR (300 MHz, CDCl$_3$, δ): 7.4-8.2 (m, 10H), 2.0-2.1 (m, 4H), 1.3-1.7 (m, 8H), 1.4 (s, 9H), 1.2 (s, 24H), 0.9 (t, 2H), 0.85 (t, 2H).

Finally, 12 mg (35%) of compound 1al was obtained using General Procedure F, described above. MS (LC/MS, ESI): 240 (M−2H$_2$O+H). $^1$H NMR (300 MHz, D$_2$O, δ): 2.0 (m, 4H) 1.4-1.8 (m, 8H), 0.8 (t, 4H).

Example 39.
2-Amino-2-(4-boronobutyl)hex-4-enoic acid hydrochloride (1am)

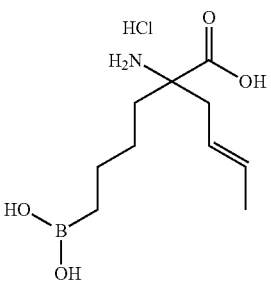

Compound 1am, 15 mg (20%), was obtained from 21al, discussed above, using General Procedure F, described above. MS (LC/MS, ESI): 212 (M−H$_2$O+H). $^1$H NMR (300 MHz, D$_2$O, δ): 5.4 (m, 2H), 1.9-2.1 (m, 2H), 2.0 (d, 3H), 1.4-1.8 (m, 6H), 0.9 (t, 2H).

Example 40. 2-Amino-6-borono-2-(2-(2-methoxyethoxy)ethyl)hexanoic acid hydrochloride (1an)

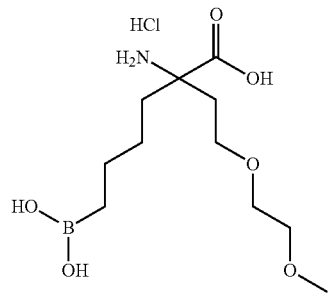

1an

Compound 1an, illustrated above, was synthesized by the following procedure.

tert-Butyl 2-(diphenylmethyleneamino)-4-(2-methoxyethoxy)butanoate (20an)

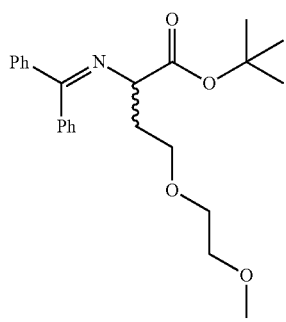

20an

Compound 20an, 0.58 g (36%), was obtained using General Procedure B, described above. MS (LC/MS, ESI): 398 (M+H), 342 (M−tBu+H). $^1$H NMR (300 MHz, CDCl$_3$, δ): 7.4-8.0 (m, 10H), 4.1 (t, 1H), 3.5 (s, 3H), 3.2-3.4 (br s, 6H), 2.2 (m, 2H), 1.4 (s, 9H).

tert-Butyl 2-(diphenylmethyleneamino)-2-(2-(2-methoxyethoxy)ethyl)hex-4-enoate (21an)

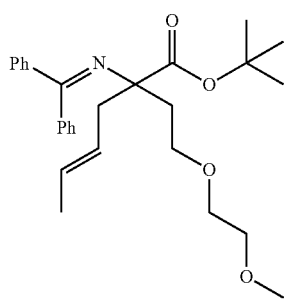

21an

Compound 21an, 0.40 g (61%), was obtained using General Procedure C, described above. MS (LC/MS, ESI): 452 (M+H), 396 (M−tBu+H). $^1$H NMR (300 MHz, CDCl$_3$, δ): 7.4-8.0 (m, 10H), 5.4 (m, 2H), 3.5 (s, 3H), 3.2-3.4 (br s, 6H), 2.5 (m, 2H), 2.2 (m, 2H), 2.0 (d, 3H), 1.4 (s, 9H).

tert-Butyl 2-(diphenylmethyleneamino)-2-(2-(2-methoxyethoxy)ethyl)-6-(4,4,5,5-tetramethyl-1,3,2-dioxaborolan-2-yl)hexanoate (19an)

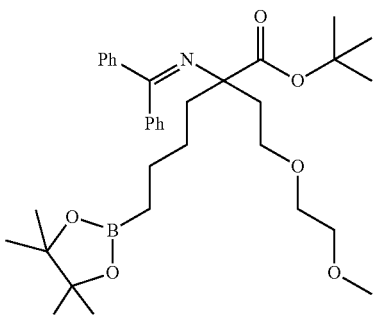

19an

Compound 19an, 0.31 g (60%), was obtained using General Procedure D, described above. MS (LC/MS, ESI): 580 (M+H), 524 (M−tBu+H). $^1$H NMR (300 MHz, CDCl$_3$, δ): 7.4-8.0 (m, 10H), 3.5 (s, 3H), 3.2-3.4 (br s, 6H), 2.5 (m, 2H), 2.2 (m, 2H), 1.4 (s, 9H), 1.3-1.7 (m, 4H), 1.2 (s, 12H), 0.9 (t, 2H).

Finally, 35 mg (21%) of compound 1an was obtained using General Procedure F, described above. MS (LC/MS, ESI): 260 (M−H$_2$O+H). $^1$H NMR (300 MHz, D$_2$O, δ): 3.5 (s, 3H), 3.2-3.4 (br 2, 6H), 2.5 (m, 2H), 1.9-2.1 (m, 2H), 1.4-1.8 (m, 4H), 0.8 (t, 2H).

Example 41. 2-Amino-6-borono-2-methylhexanoic acid hydrochloride (1ao)

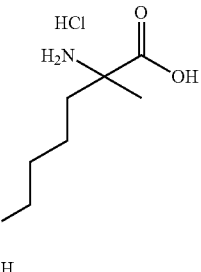

1ao

Compound 1ao, illustrated above, was synthesized by the following procedure.

(S)-tert-Butyl 2-(diphenylmethyleneamino)propanoate (20ao)

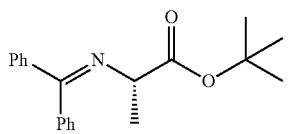

20ao

Compound 20ao, 1.76 g (91%), was obtained using General Procedure A, described above. MS (LC/MS, ESI): 310 (M+H), 254 (M−tBu+H). ¹H NMR (300 MHz, CDCl₃, δ): 7.4-8.0 (m, 10H), 4.1 (m, 1H), 1.5 (d, 3H), 1.4 (s, 9H).

tert-Butyl 2-(diphenylmethyleneamino)-2-methylhex-4-enoate (21ao)

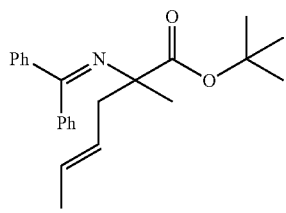

21ao

Compound 21ao, 0.61 g (82%), was obtained using General Procedure C, described above. MS (LC/MS, ESI): 364 (M+H), 308 (M−tBu+H). ¹H NMR (300 MHz, CDCl₃, δ): 7.4-8.0 (m, 10H), 5.4 (m, 2H), 2.5-2.8 (m, 2H), 2.1 (d, 3H), 1.6 (s, 3H), 1.4 (s, 9H).

tert-Butyl 2-(diphenylmethyleneamino)-2-methyl-6-(4,4,5,5-tetramethyl-1,3,2-dioxaborolan-2-yl) hexanoate (19ao)

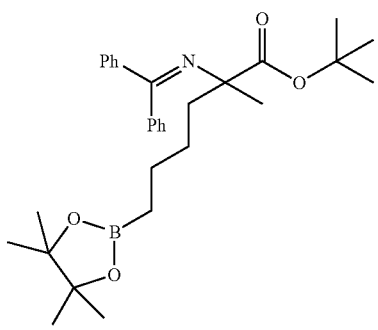

19ao

Compound 19ao, 0.49 g (59%), was obtained using General Procedure E, described above. MS (LC/MS, ESI): 492 (M+H), 436 (M−tBu+H). ¹H NMR (300 MHz, CDCl₃, δ): 7.4-8.0 (m, 10H), 2.0 (m, 2H), 1.6 (s, 3H), 1.4 (s, 9H), 1.3-1.5 (m, 4H), 1.2 (s, 12H), 0.9 (t, 2H).

Finally, compound 1ao, 82 mg (38%), was obtained using General Procedure F, described above. MS (LC/MS, ESI): 172 (M−H₂O+H). ¹H NMR (300 MHz, D₂O, δ): 1.9-2.1 (m, 2H), 1.4 (s, 3H), 1.4 (m, 2H), 1.1 (m, 2H), 0.8 (t, 2H).

Example 42. 2-Amino-6-borono-2-isobutylhexanoic acid hydrochloride (1ap)

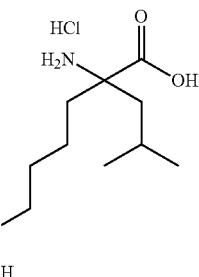

1ap

Compound 1ap, illustrated above, was synthesized by the following procedure.

(S)-tert-Butyl 2-(diphenylmethyleneamino)-4-methylpentanoate (20ap)

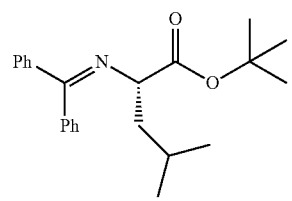

20ap

Compound 20ap, 0.79 g (100%), was obtained using General Procedure A, described above. MS (LC/MS, ESI): 352 (M+H), 296 (M−tBu+H). ¹H NMR (300 MHz, CDCl₃, δ): 7.4-8.0 (m, 10H), 4.0 (m, 1H), 1.9 (m, 2H), 1.7 (m, 1H), 1.5 (d, 3H), 1.4 (s, 9H), 0.8 (dd, 6H).

tert-Butyl 2-(diphenylmethyleneamino)-2-isobutyhex-4-enoate (21ap)

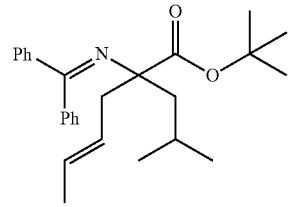

21ap

Compound 21ap, 0.70 g (81%), was obtained using General Procedure C, described above. MS (LC/MS, ESI): 406 (M+H), 350 (M−tBu+H). ¹H NMR (300 MHz, CDCl₃, δ): 7.4-8.0 (m, 10H), 5.4 (m, 2H), 2.5-2.8 (m, 2H), 2.1 (d, 3H), 1.9 (m, 2H), 1.7 (m, 1H), 1.4 (s, 9H), 0.9 (dd, 6H).

tert-Butyl 2-(diphenylmethyleneamino)-2-isobutyl-6-(4,4,5,5-tetramethyl-1,3,2-dioxaborolan-2-yl)hexanoate (19ap)

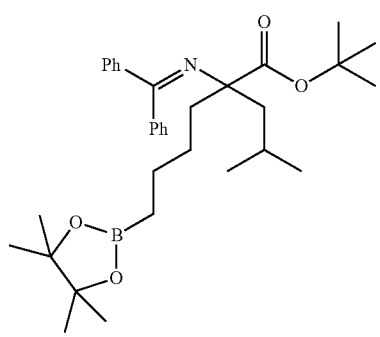

19ap

Compound 19ap, 0.51 g (58%), was obtained using General Procedure E, described above. MS (LC/MS, ESI): 534 (M+H), 478 (M−tBu+H). $^1$H NMR (300 MHz, CDCl$_3$, δ): 7.4-8.0 (m, 10H), 1.9-2.1 (m, 4H), 1.7 (m, 1H), 1.4 (s, 9H), 1.3-1.5 (m, 4H), 1.2 (s, 12H), 0.9 (dd, 6H), 0.8 (t, 2H).

Finally, compound 1ap, 0.16 g (63%), was obtained using General Procedure F, described above. MS (LC/MS, ESI): 214 (M−H$_2$O+H). $^1$H NMR (300 MHz, D$_2$O, δ): 1.9-2.1 (m, 4H), 1.4-1.8 (m, 5H), 0.9 (dd, 6H), 0.7 (t, 2H).

Example 43.
2-Amino-6-borono-2-(hydroxymethyl)hexanoic acid hydrochloride (1aq)

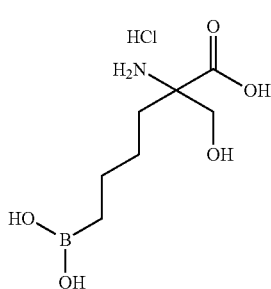

1aq

Compound 1aq, illustrated above, was synthesized by the following procedure.

(S)-Methyl 3-tert-butoxy-2-(diphenylmethyleneamino)propanoate (20aq)

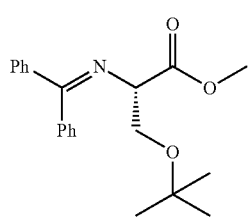

20aq

Compound 20aq, 0.71 g (88%), was obtained using General Procedure A, described above. MS (LC/MS, ESI): 340 (M+H), 284 (M−tBu+H). $^1$H NMR (300 MHz, CDCl$_3$, δ): 7.4-8.0 (m, 10H), 4.2 (m, 1H), 3.9 (m, 2H), 3.75 (s, 3H), 1.25 (s, 9H).

Methyl 2-(tert-butyoxymethyl)-2-(diphenylmethyleneamino)hex-4-enoate (21aq)

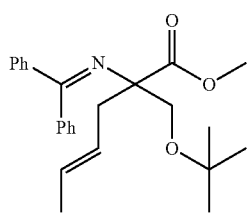

21aq

Compound 21aq, 0.67 g (82%), was obtained using General Procedure C, described above. MS (LC/MS, ESI): 393 (M+H), 338 (M−tBu+H). $^1$H NMR (300 MHz, CDCl$_3$, δ): 7.4-8.0 (m, 10H), 5.4 (m, 2H), 3.9-4.1 (m, 2H), 3.75 (s, 3H), 2.5-2.8 (m, 2H), 2.1 (d, 3H), 1.25 (s, 9H).

Methyl 2-(tert-butyoxymethyl)-2-(diphenylmethyleneamino)-6-(4,4,5,5-tetramethyl-1,3,2-dioxaborolan-2-yl)hexanoate (19aq)

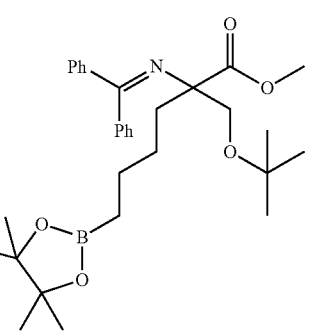

19aq

Compound 19aq, 0.55 g (63%), was obtained using General Procedure E, described above. MS (LC/MS, ESI): 522 (M+H), 466 (M−tBu+H). $^1$H NMR (300 MHz, CDCl$_3$, δ): 7.4-8.0 (m, 10H), 3.9-4.1 (m, 2H), 3.75 (s, 3H), 2.0 (m, 2H), 1.3-1.5 (m, 4H), 1.25 (s, 9H), 1.2 (s, 12H), 0.9 (t, 2H).

Finally, compound 1aq, 29 mg (56%), was obtained using General Procedure F, described above. MS (LC/MS, ESI): 170 (M−2H$_2$O+H). $^1$H NMR (300 MHz, D$_2$O, δ): 3.9-4.1 (dd, 2H), 1.6-1.8 (m, 2H), 1.3 (m, 2H), 1.1 (m, 2H), 0.7 (t, 2H).

Examples 44 and 45

(R)-2-Amino-6-borono-2-(hydroxymethyl)hexanoic acid (1ar) and (S)-2-Amino-6-borono-2-(hydroxymethyl)hexanoic acid (1as)

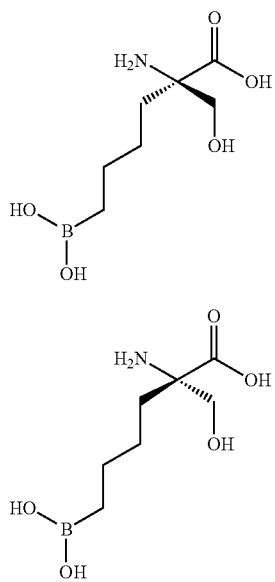

Both of compounds 1ar and 1as were prepared in analogous manner as the compounds synthesized in FIG. 15, as described in detail below.

(S)-tert-Butyl 2-(naphthalene-1-yl)-4,5-dihydooxazole-4-carboxylate (46)

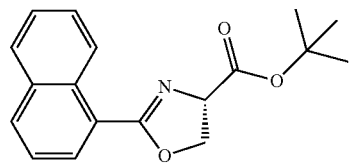

1-Naphthoyl chloride (0.97 g, 5.1 mmol) and ser-OtBu HCl (1.00 g, 5.06 mmol) were dissolved in 30 mL dry DCM and Et$_3$N (1.5 mL, 10.76 mmol) was added. The reaction mixture was stirred for 4 hr at room temperature, diluted with DCM, washed 3× with 1 N HCl, 1× with brine and dried over dried over MgSO$_4$, filtered and concentrated to dryness in vacuo to give 1.51 g (100%) of a white solid. MS (LC/MS, ESI): 316 (M+H), 250 (M−tBu+H).

This reaction product was treated with (diethylamino)sulfur trifluoride (0.79 mL, 6.0 mmol) in 20 mL dry DCM under argon at −78° C. for 2-8 hr. The cold solution was diluted with additional dry DCM and poured into sat NaHCO$_3$ solution and stirred at room temperature for 30 minutes. The layers were separated and the aqueous layer washed 3× with DCM, the organic layer was washed 1× with brine and dried over dried over MgSO$_4$, filtered and concentrated to dryness in vacuo. The product was purified by silica gel chromatography by eluting with 1-10% ethyl acetate/hexane to give 0.99 g (66%) of compound 46 as an oil. MS (LC/MS, ESI): 298 (M+H), 242 (M−tBu+H).

(R)-tert-Butyl 4-(but-2-enyl)-2-(naphthalene-1-yl)-4,5-dihydrooxazole-4-carboxylate (47b)

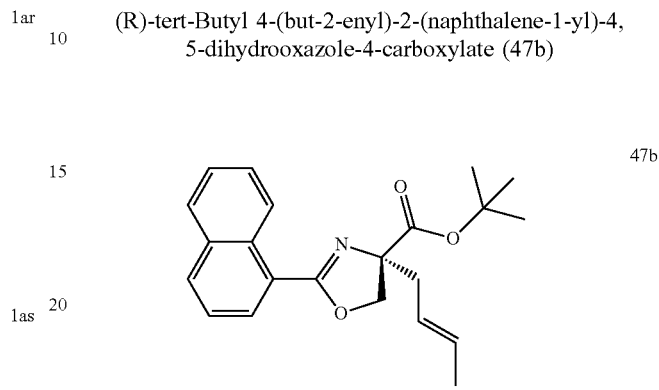

Compound 46 (0.46 g, 1.5 mmol) was dissolved in 4 mL dry DCM under argon and 25 mg (0.033 mmol) of compound 45 and 0.93 g (7.68 mmol) crotyl bromide were added and the mixture cooled to 0° C. To this mixture was added 1.25 g (7.50 mmol) CsOH hydrate and the mixture was stirred vigorously at 0° C. for 12-16 hr. The reaction was quenched with the addition of 5 mL 1 N HCl and diluted with additional DCM. The layers were separated and the organic layer washed 1× with 1 N HCl and 1× with brine and dried over dried over MgSO$_4$, filtered and concentrated to dryness in vacuo. The product was purified by silica gel chromatography by eluting with 1-3% ethyl acetate/hexane to yield 0.24 g (46%) of compound 47b as a clear oil. MS (LC/MS, ESI): 298 (M+H), 242 (M−tBu+H). $^1$H NMR (300 MHz, CDCl$_3$, δ): 7.5-84 (m, 7H), 5.5 (m, 2H), 4-4.4 (m, 2H), 2.5-2.8 (m, 2H), 2.1 (d, 3H), 1.45 (s, 9H).

Chirality analysis of this product indicated that the enantiomeric excess was 40%. The opposite enantiomer was also obtained by the same procedure except that the opposite antipode for the catalyst was used.

Alternatively, both the R and S enantiomers of compound 47 were obtained by alkylation of compound 46 as follows. Compound 46 (0.82 g, 2.8 mmol) was dissolved in 10 mL dry DCM under argon. 0.42 mL (3.5 mmol) crotyl bromide, and 1.07 mL (3.5 mmol) BTPP were added. The mixture was stirred 12-16 hr at room temperature and then concentrated to dryness in vacuo. The product was purified by silica gel chromatography by eluting with 1-3% ethyl acetate/hexane to yield 0.93 g (96%) of racemic compound 47 as a clear oil. The enantiomers of compound 47 were separated on a ChiralPak AD-H chromatography column by eluting 500 mg of compound 47 with 10% ethanol/carbon dioxide to yield 79 mg of peak 1 (47a) and 150 mg of peak 2 (47b). Chiral analysis of these two products indicated that the enantiomeric excess was >98% for each.

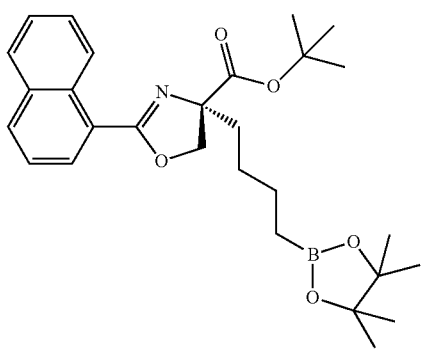

48b

Compound 47b (150 mg) was treated as described in General Procedure E, described above, to yield 120 mg of compound 48b. MS (LC/MS, ESI): 480 (M+H), 424 (M−tBu+H). $^1$H NMR (300 MHz, CDCl$_3$, δ): 7.5-84 (m, 7H), 4-4.4 (m, 2H), 2.0 (m, 2H), 1.3-1.5 (m, 4H), 1.25 (s, 9H), 1.2 (s, 12H), 0.9 (t, 2H).

Next, 120 mg (0.085 mmol) of compound 48b was treated with 6 N HCl at 100° C. for 12-16 hr. The solution was lyophilized to dryness to yield 57 mg of compound 1ar, as a clear glass. MS (LC/MS, ESI): 234 (M+H), 216 (M−H$_2$O+H).

Compound 1as (24 mg) was obtained as a clear glass in a similar fashion starting from compound 47a.

Example 46. 2-Amino-2-(2-(benzyloxy)-2-oxoethyl)-6-boronohexanoic acid hydrochloride (1at)

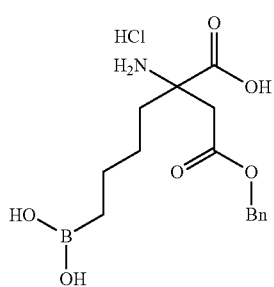

1at

Compound 1at, illustrated above, was synthesized in accordance with the principles illustrated in FIG. 9, starting with compound 16c (wherein R=tert-butyl). Compound 16c (1.50 g, 5.10 mmol) was dissolved in 25 mL anhydrous DCM under argon. Crotyl bromide (1.00 mL, 8.26 mmol) and BTPP (2.30 mL, 7.50 mL) were added to the reaction mixture followed by stirring overnight at room temperature. Product 22 was purified by concentrating the reaction mixture to a puddle, redissolving it in a small amount of DCM, applying it to a dry silica gel column, and eluting it with mixtures of EtOAc/hexane (0.5-2%). MS (LC/MS, ESI): 350 (M+H), 295 (M−tBu+H). $^1$H NMR (300 MHz, CDCl$_3$, δ): 7.4-8.2 (m, 10H), 5.4 (m, 2H), 4.0 (m, 1H), 2.5-2.8 (m, 2H), 2.0 (d, 3H), 1.4 (s, 9H).

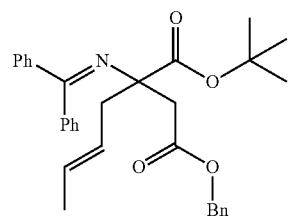

21at

Compound 21at (depicted above), 0.205 g (44%), was obtained using General Procedure C, also described above. MS (LC/MS, ESI): 498 (M+H), 442 (M−tBu+H). $^1$H NMR (300 MHz, CDCl$_3$, δ): 7.4-8.0 (m, 15H), 5.4 (m, 2H), 5.2 (s, 2H), 2.8-3.2 (q, 2H), 2.5-2.8 (m, 2H), 2.0 (d, 3H), 1.4 (s, 9H).

19at

Still referring to FIG. 9, compound 19at (depicted above), 0.130 g (51%), was obtained using General Procedure E, also described above. MS (LC/MS, ESI): 626 (M+H), 570 (M−tBu+H). $^1$H NMR (300 MHz, CDCl$_3$, δ): 7.4-8.2 (m, 15H), 5.2 (s, 2H), 2.8-3.2 (q, 2H), 1.4-1.8 (m, 4H), 1.5 (s, 9H), 1.2 (s, 12H), 0.8 (t, 2H).

Finally, 29 mg (39%) of compound 1at was obtained using General Procedure G, described above. MS (LC/MS, ESI): 306 (M−H$_2$O+H). $^1$H NMR (300 MHz, D$_2$O, δ): 7.3-7.5 (m, 5H), 5.2 (s, 2H), 2.6-2.8 (q, 2H), 1.8-1.9 (m, 4H), 1.4-1.6 (m, 4H), 0.7 (t, 2H).

Examples 47-48

The following compounds listed in Table 3, below, were synthesized in analogous manner as described above for compound 1at. In Table 3, each compound has the following chemical structure (each example in the Table has a different R$^1$ group):

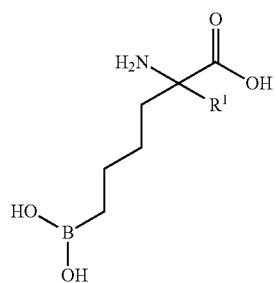

TABLE 3

| Example No. | Compound No. | R¹ | Amount Isolated | MS Data | Physical Appearance |
|---|---|---|---|---|---|
| 47 | 1au | 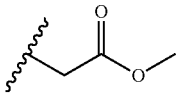 [SMILES: *CC(=O)OC] | 30 mg | 248, 230 | Light tan solid |
| 48 | 1ay | 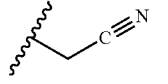 [SMILES: *CC#N] | 19 mg | 215, 197 | Clear glass |

Example 49.
2-Amino-6-borono-2-(2-oxobutyl)hexanoic acid hydrochloride (1aw)

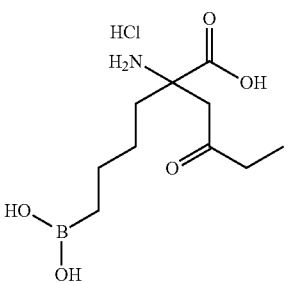

1aw

Compound 1aw was synthesized in accordance with the principles illustrated in FIG. 7.

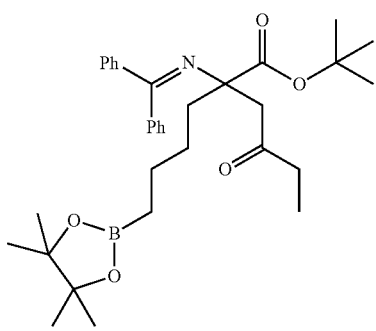

19aw

Referring to FIG. 7, compound 18 (wherein R=tBu, 240 mg, 0.50 mmol) was reacted with 1-bromobutan-2-one (80 mg, 0.525 mmol) using General Procedure C, described above, to give compound 19aw (50 mg, 18%). MS (LC/MS, ESI): 548 (M+H), 492 (M−tBu+H). $^1$H NMR (300 MHz, CDCl$_3$, δ): 7.4-8.2 (m, 10H), 3.0-3.2 (q, 2H), 2.5 (m, 2H), 1.4-1.8 (m, 4H), 1.5 (s, 9H), 1.2 (s, 12H), 1.1 (t, 3H), 0.8 (t, 2H).

Finally, 7 mg of compound 1aw was obtained using General Procedure G, described above. MS (LC/MS, ESI): 227 (M−H$_2$O+H), 245 (M+H). $^1$H NMR (300 MHz, D$_2$O, δ): 3.0-3.1 (q, 2H), 1.8-1.9 (m, 4H), 1.4-1.6 (m, 4H), 1.1 (t, 3H), 0.7 (t, 2H).

Example 50. 2-Amino-6-borono-2-(2-oxo-2-phenyl-ethyl)hexanoic acid hydrochloride (1ax)

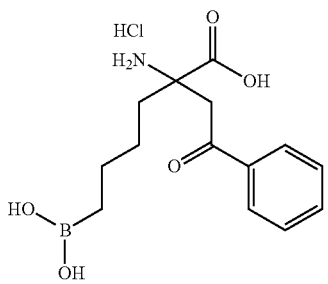

1ax

Compound 1ax (28 mg) was obtained as a clear glass using analogous procedures outlined above for compound 1aw. MS (LC/MS, ESI): 276 (M−H$_2$O+H).

Example 51. 2-Amino-2-(2-(2-aminoethoxy)ethyl)-6-boronohexanoic acid dihydrochloride (1ay)

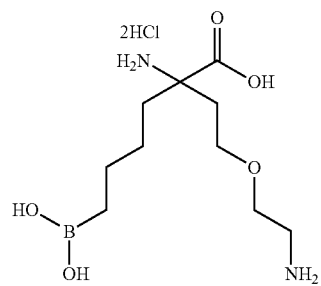

1ay

Compound 1ay was synthesized in accordance with the principles illustrated in FIGS. 8 and 11, as described in detail below.

tert-Butyl 4-(2-(bis(tert-butoxycarbonyl)amino) ethoxy)-2-(diphenylmethyleneamino)butanoate (20ay)

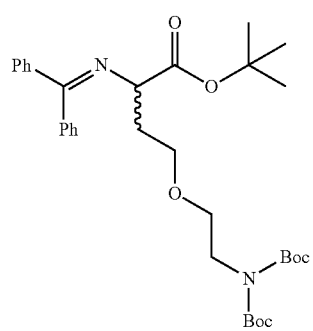

20ay

Compound 20ay, 0.99 g (85%), was obtained using General Procedure B, described above. MS (LC/MS, ESI): 583 (M+H), 527 (M−tBu+H), 483 (M−Boc+H). $^1$H NMR (300

MHz, CDCl₃, δ 7.4-8.0 (m, 10H), 3.95 (t, 1H), 3.6 (t, 2H), 3.4 (m, 4H), 2.2 (m, 2H), 1.5 (s, 9H), 1.45 (s, 9H).

tert-Butyl 2-(2-(2-bis(tert-butoxycarbonyl)amino)
ethoxy-2-(diphenylmethyleneamino)hex-4-enoate
(21ay)

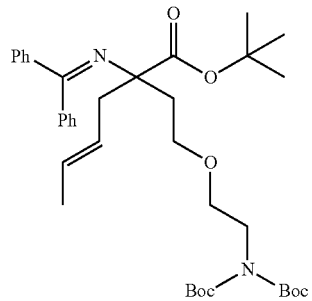

21ay

Compound 21ay, 0.90 g (83%), was obtained using General Procedure C, described above. MS (LC/MS, ESI): 637 (M+H), 581 (M–tBu+H), 537 (M–Boc+H). ¹H NMR (300 MHz, CDCl₃, δ): 7.4-8.0 (m, 10H), 5.4 (m, 2H), 3.6 (t, 2H), 3.4 (m, 4H), 2.5 (m, 2H), 2.2 (m, 2H), 2.0 (d, 3H), 1.5 (s, 9H), 1.45 (s, 9H).

tert-Butyl 2-(2-(2-(bis(tert-butoxycarbonyl)amino)
ethoxy)ethyl)-2-(diphenylmethyleneamino)-6-(4,4,5,
5-tetramethyl-1,3,2-dioxaborolan-2-yl)hexanoate
(19ay)

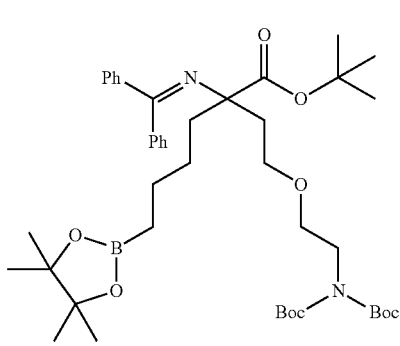

19ay

Compound 19ay, 0.25 g (28%), was obtained using General Procedure E, described above. MS (LC/MS, ESI): 765 (M+H), 709 (M–tBu+H), 665 (M–Boc+H). ¹H NMR (300 MHz, CDCl₃, δ): 7.4-8.0 (m, 10H), 3.6 (t, 2H), 3.4 (m, 4H), 2.5 (m, 2H), 2.2 (m, 2H), 1.4-1.8 (m, 4H), 1.5 (s, 9H), 1.45 (s, 9H), 0.8 (t, 2H).

Finally, 16 mg (73%) of compound 1ay as a clear glass was obtained using General Procedure F, described above. MS (LC/MS, ESI): 263 (M+H), 245 (M–H₂O+H).

Examples 52-54

The following compounds listed in Table 4, below, were synthesized in analogous manner as described above for compound 1ay. In Table 4, each compound has the following chemical structure (each example in the Table has a different R¹ group):

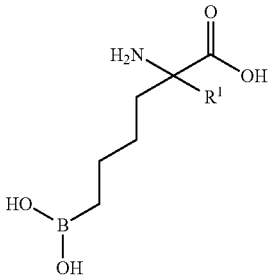

TABLE 4

| Example No. | Compound No. | R¹ | Amount Isolated | MS Data | Physical Appearance |
|---|---|---|---|---|---|
| 52 | 1az | ![piperidine-butyl] | 20 mg | 301, 283 | White flocculent powder |
| 53 | 1ba | ![piperazine-butyl] | 20 mg | 302, 285 | White powder |

TABLE 4-continued

| Example No. | Compound No. | R¹ | Amount Isolated | MS Data | Physical Appearance |
|---|---|---|---|---|---|
| 54 | 1bb | ~~~~~~~NH₂ | 13 mg | 247, 229 | Clear glass |

Example 55. 2-Amino-6-borono-2-(2-(2-(4-cyanobenzamid)ethoxy)ethyl)hexanoic acid trifluoroacetate (38a)

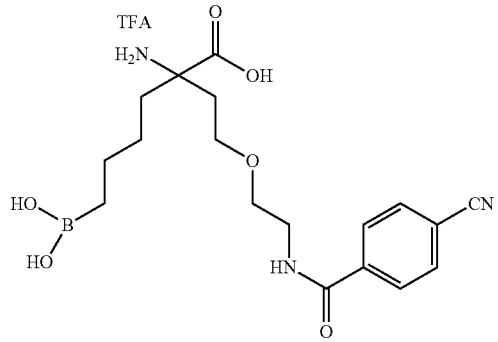

38a

Compound 38a (8 mg as a white powder) was prepared from compound 19ay in accordance with the principles illustrated in FIG. 12 and described in General Procedure J, described above. MS (LC/MS, ESI): 392 (M+H), 374 (M−$H_2O$+H).

Examples 56-67

The following compounds listed in Table 5, below, were synthesized in analogous manner as described above for compound 38a. In Table 5, each compound has the following chemical structure (each example in the Table has a different R¹ group):

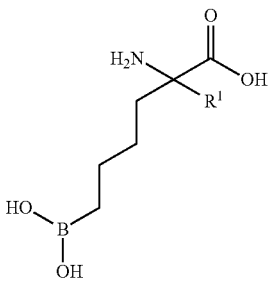

TABLE 5

| Example No. | Compound No. | R¹ | Amount Isolated | MS Data | Physical Appearance |
|---|---|---|---|---|---|
| 56 | 38b | ~~~~O~~~N(H)~C(O)CH₃ | 12 mg | 304, 286 | Light tan powder |
| 57 | 39a | ~~~~O~~~NH-C(O)-NH-C₆H₄-OMe | 16 mg | 412, 394 | White powder |
| 58 | 38c | ~~~~(piperidine-N-acetyl) | 7 mg | 343 | White powder |

TABLE 5-continued

| Example No. | Compound No. | R¹ | Amount Isolated | MS Data | Physical Appearance |
|---|---|---|---|---|---|
| 59 | 39b | *piperidine linked via C4-butyl chain, N-C(O)-NH-(3-methoxyphenyl)* | 6 mg | 450, 432 | Light tan powder |
| 60 | 38d | *butyl-piperazine-N-C(O)-CH₃* | 6 mg | 344, 326 | Light tan powder |
| 61 | 38e | *butyl-piperazine-N-C(O)-(4-cyanophenyl)* | 6 mg | 431, 413 | White powder |
| 62 | 39c | *butyl-piperazine-N-C(O)-NH-(3-methoxyphenyl)* | 6 mg | 451, 433 | White powder |
| 63 | 40a | *pentyl-NH-SO₂-(4-methylphenyl)* | 26 mg | 401, 383 | White powder |
| 64 | 38f | *pentyl-NH-C(O)-(3,5-difluorophenyl)* | 18 mg | 387, 369 | White powder |
| 65 | 38g | *pentyl-NH-C(O)-O-CH₂-phenyl* | 12 mg | 381, 363 | White powder |
| 66 | 38h | *pentyl-NH-C(O)-CH₃* | 8 mg | 289, 271 | White powder |
| 67 | 39d | *pentyl-NH-C(O)-NH-CH₂-(3-methoxyphenyl)* | 17 mg | 396, 378 | White powder |

Example 68.
2-Amino-4-(2-hydroxyguanidino)-2-methylbutanoic acid dihydrochloride (54a)

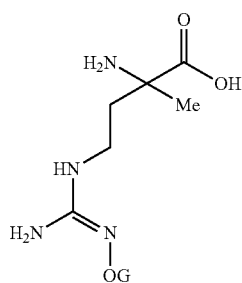

54a

Compound 54a was prepared in accordance with the synthesis illustrated in FIG. 16, wherein $R^1$ is a methyl group.

tert-Butyl 3-cyano-2-(diphenylmethyleneamino)-2-methyl propanoate (49a)

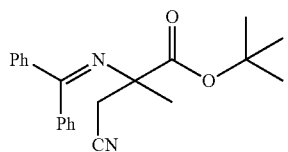

49a

Compound 49a, 0.90 g (80%), was prepared from compound 20ao using General Procedure C, described above. MS (LC/MS, ESI): 349 (M+H), 293 (M−tBu+H). $^1$H NMR (300 MHz, CDCl$_3$, δ): 7.4-8.0 (m, 10H), 2.9-3.3 (m, 2H), 1.6 (s, 3H), 1.4 (s, 9H).

tert-Butyl 2-(tert-butoxycarbonylamino)-3-cyano-2-methylpropanoate (50a)

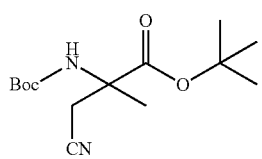

50a

Compound 49a, 500 mg (1.4 mmol), was treated with 2.5 mL 1 N HCl/THF (1:2) for 2 hr at room temperature. Ethyl acetate was added to the reaction mixture and the layers separated. The aqueous layer was washed two additional times with EtOAc and then the pH of the aqueous layer was adjusted to about 10 by the addition of 1 N NaOH. This aqueous solution was washed with DCM 3× and the DCM was concentrated to dryness in vacuo to give 250 mg of an oil. This was immediately dissolved in 3 mL THF and 340 mg (1.5 mmol) of di-tert-butyl dicarbonate was added. This mixture was stirred for 48 hr and ethyl acetate and 0.1 N HCl was added to the mixture. The layers were separated and the organic solution was washed 1× with brine, dried over MgSO$_4$, filtered and concentrated to dryness in vacuo to give an oil. This oil was purified by silica gel chromatography by eluting with mixtures of EtOAc/hexane (5-10%) to give purified compound 50a (275 mg, 70%). MS (LC/MS, ESI): 285 (M+H), 229 (M−tBu+H). $^1$H NMR (300 MHz, CDCl$_3$, δ): 5.2 (m, 1H), 2.9-3.3 (m, 2H), 1.6 (s, 3H), 1.45 (s, 9H), 1.4 (s, 9H).

tert-Butyl 4-amino-2-(tert-butoxycarbonylamino)-2-methylbutanoate hydrochloride (51a)

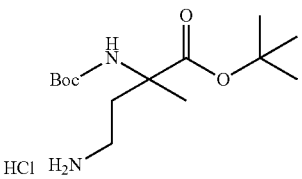

51a

In a Parr hydrogenation bottle, 240 mg of compound 50a (0.84 mmol) was dissolved in 10 mL dry methanol and 0.84 mL of 1 N HCl was added to the solution. PtO$_2$ (50 mg) was added and a hydrogen gas atmosphere (60 psi) was introduced. The hydrogen atmosphere was recharged as needed to keep this pressure maintained and the reaction mixture was vigorously mixed for 24 hr. The reaction mixture was again filtered over Celite brand diatomaceous earth, and the solvent concentrated in vacuo to give compound 51a (270 mg, 100%) as a light brown solid. MS (LC/MS, ESI): 289 (M+H), 233 (M−tBu+H). $^1$H NMR (300 MHz, DMSO-d6, δ): 2.7 (m, 2H), 2.3 (m, 2H), 1.6 (s, 3H), 1.45 (s, 9H), 1.4 (s, 9H).

tert-Butyl 2-(tert-butoxycarbonylamino)-4-cyanamido-2-methylbutanoate (52a)

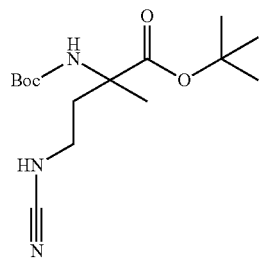

52a

Compound 51a, 150 mg (0.462 mmol), was dissolved in 5 mL dry methanol and CNBr (53 mg, 0.51 mmol) and NaOAc (100 mg, 1.20 mmol) were added to this solution. The reaction mixture was stirred for 48 hr at room temperature and an additional 10 mg of CNBr was added with continued stirring for 24 hr at room temperature. The reaction mixture was concentrated in vacuo, ethyl acetate and water were added to the solid residue, and the layers were separate and the aqueous solution washed 2× with ethyl acetate. The organic solution was washed 1× with brine, dried over MgSO$_4$, filtered and concentrated to dryness in vacuo to give compound 52a (140 mg, 99%) as a light brown solid. MS (LC/MS, ESI): 314 (M+H), 258 (M−tBu+H).

tert-Butyl 2-(tert-butoxycarbonylamino)-4-(2-hydroxyguanidino)-2-methylbutanoate (53a)

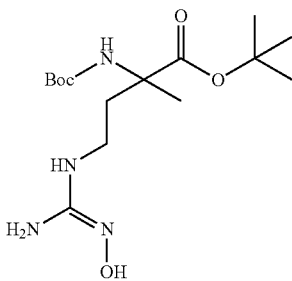

53a

Compound 52a, 94 mg (0.30 mmol), was dissolved in 4 mL dioxane and 40 mg of hydroxylamine hydrochloride (0.58 mmol) and 100 mg of $Na_2CO_3$ (1.20 mmol) were added to this solution. The reaction mixture was heated at 70° C. for 4 hr, cooled to room temperature, and ethyl acetate and water was added to the reaction mixture. The layers were separated and the aqueous layer was washed 2× with EtOAc. The organic solution was washed 1× with brine, dried over $MgSO_4$, filtered and concentrated to dryness in vacuo to give a glassy residue. This product was purified by silica gel chromatography by eluting with 3% MeOH/DCM to give compound 53a (60 mg, 58%) as a white glass. MS (LC/MS, ESI): 347 (M+H), 291 (M−tBu+H). $^1$H NMR (300 MHz, $CD_3OD$, δ): 2.8 (m, 2H), 2.3 (m, 2H), 1.6 (s, 3H), 1.45 (s, 9H), 1.4 (s, 9H).

Finally, compound 54a (40 mg) was obtained by treating compound 53a with 6 N HCl/THF (1:1) at room temperature for 4 hr. The solvents were removed in vacuo to give a white glass. MS (LC/MS, ESI): 191 (M+H). $^1$H NMR (300 MHz, $D_2O$, δ): 2.4 (m, 2H), 2.0 (m, 2H), 1.7 s, 3H).

Example 69. Biological Assay of Arginase Inhibition

Quantitative determination of arginase activity was performed by a colorimetric method using the QuantiChrom™ Arginase Assay Kit available from BioAssay Systems (Hayward, Calif., Catalog No. DARG-200), which was used according to the manufacture's protocol. Briefly, the method utilizes a chromogen that forms a colored complex specifically with urea produced in the arginase reaction. See, Mellerup, "Colorimetric method for rapid determination of serum arginase," Clin. Chem. 13, 900-08 (1967). The intensity of the color is directly proportional to the arginase activity in the sample.

The rate of urea production was measured in the presence of twelve different concentrations of each potential inhibitor compound. The half maximal inhibitory concentration ($IC_{50}$) was determined by constructing a dose-response curve. As $IC_{50}$ values are dependent upon the measurement conditions, the $IC_{50}$ values are converted to the inhibitor binding affinity ($K_i$) using the Cheng-Prusoff equation and the measured affinity constant ($K_m$) of L-arginine. See, e.g., Cheng et al., "Relationship between the inhibition constant ($K_1$) and the concentration of inhibitor which causes 50 percent inhibition ($I_{50}$) of an enzymatic reaction," Biochem. Pharmacol. 22, 3099-108 (1973).

The inhibitor binding affinities for both human arginase I and II ("hArgI" and "hArgII," respectively) are listed below in Table 6.

TABLE 6

| Compound No. | $K_i$ | |
|---|---|---|
| | hArgI | hArgII |
| ABH | +++ | +++ |
| Rac-ABH | +++ | ++ |
| Nor-NOHA | + | + |
| 1a | + | + |
| 1d | +++ | +++ |
| 1aa | ++ | ++ |
| 1ao | +++ | ++ |
| 1ap | ++ | ++ |
| 1aq | +++ | ++ |
| 1aw | ++ | ++ |
| 1ax | ++ | ++ |
| 1e | ++ | ++ |
| 1ad | ++ | ++ |
| 1as | + | + |
| 1ar | +++ | +++ |
| 54a | + | + |
| 1az | +++ | +++ |
| 1ba | ++ | ++ |
| 38b | + | + |
| 39a | ++ | ++ |
| 38a | ++ | ++ |
| 1h | +++ | ++ |
| 39c | ++ | ++ |
| 1bb | +++ | +++ |
| 40a | ++ | ++ |

"+++" = $10^{-10} < K_i < 10^{-8}$ M;
"++" = $10^{-8} < K_i < 10^{-7}$ M; and
"+" = $10^{-7} < K_i < 5 \times 10^{-7}$ M.
"ABH" and "nor-NOHA" (illustrated in FIG. 18) and Rac-ABH (racemic ABH) are control samples.

In Table 6, the $K_i$ values reflect the potency of these molecules to inhibit the catalytic activity of arginase to produce urea from the substrate L-arginine. Lower $K_i$ values signify more effective enzyme inhibition. Those compounds with the lowest (most potent) to the highest $K_i$ values (least potent) are identified by "+++," "++," and "+," respectively. The potencies of these examples (except the non-racemic compounds compounds 1ar and 1as) should be compared to that of the closest prior art, racemic-ABH ("Rac-ABH") in Table 6. That is, racemic materials were compared to racemic controls. Thus, there are several examples that have similar potencies to Rac-ABH. Furthermore, if one synthesizes the single enantiomers of one of these examples, compound 1aq, and compares the potency to the active enantiomer of ABH, then one observes that one enantiomer (namely compound 1ar) is not only as potent as ABH, but is significantly (almost two orders of magnitude) more potent than the other enantiomer (compound 1as).

The structure-activity relationship for compound 1d is noteworthy because the phenoxypropyl derivative is as potent as Rac-ABH. However, compound 1ak without the aryl ring is less potent. If the phenoxy oxygen atom of compound 1d is moved closer to the α-C by one atom while maintaining the same atom distance as in the benzylic ether of compound 1aa, then potency is lost. In addition, replacing the phenoxy oxygen of compound 1d by a carbon atom as in compound 1e also results in a lost of potency. Shortening the alkyl chain by one carbon atom as in the phenoxyethyl compound 1ad also results in a potency loss. Thus, there appears to be definitive structure-activity features that results in increased potency at the molecular target, arginase, in these α,α-disubstituted derivatives.

In accordance with the foregoing observations, the $R^1$ groups can be selected to target binding interactions in the outer active site cleft and the region flanking the outer active site clefts of arginase I and II, such that the new compounds bind more tightly than their respective parent compounds. Furthermore, the Cα-R¹ groups in the compounds of formula Ia or formula Ib of the invention can be varied to alter pharmaceutically important properties, such as crystal phase or shelf stability, absorption, biodistribution, metabolism, excretion, water solubility, lipophilicity, and the like. The Cα-R¹ groups of the invention can also be varied to enhance influx or prevent efflux of the compound by cellular transport proteins.

Accordingly, those skilled in the art will appreciate that numerous changes and modifications can be made to these exemplary embodiments of the invention and that such changes and modifications can be made without departing from the spirit of the invention. Contemplated equivalents of the compounds described herein include compounds that otherwise correspond thereto and that have the same general properties thereof (e.g., functioning as arginase inhibitors), wherein one or more simple variations of substituents are made that do not adversely affect the therapeutic or diagnostic efficacy of the compound. In general, the compounds of the present invention may be prepared by the methods illustrated in the reaction schemes as, for example, described herein, or by modifications thereof, using readily available starting materials, reagents, and conventional synthesis procedures. In these reactions, it is also possible to make use of variants that are in themselves known, but are not mentioned herein.

It will be appreciated by those skilled in the art that compounds of the invention may contain a chiral center, and they may be isolated in optically active or racemic forms. Some compounds may also exhibit polymorphism. It is therefore to be understood that the present invention encompasses any racemic, optically active, polymorphic, tautomeric, zwitterionic, or stereoisomeric form, or mixture thereof, of a compound of the invention, which possesses the useful properties described herein.

It is, therefore, intended that the appended claims cover all such equivalent variations as fall within the true spirit and scope of the invention.

What is claimed is:
1. A compound of formula IA:

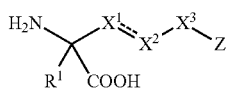

IA or a stereoisomer, lactone prodrug, or pharmaceutically-acceptable salt thereof, wherein:
said dashed line represents an optional double bond;
Z is

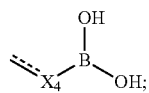

$X^1$ is —(CH$_2$)—;
$X^2$ is —(CH$_2$)—;
$X^3$ is —(CH$_2$)—;
$X^4$ is —(CH$_2$)—;
$R^1$ is ethyl, n-propyl, isopropyl, n-butyl, isobutyl, sec-butyl, tert-butyl, hydroxy($C_1$-$C_4$)alkyl, ($C_2$-$C_4$)alkenyl, ($C_6$-$C_{10}$)aryl($C_1$-$C_4$)alkyl, ($C_4$-$C_{10}$)heteroaryl($C_1$-$C_4$)alkyl, ($C_2$-$C_{10}$)heterocycloalkyl($C_1$-$C_4$)alkyl, ($C_6$-$C_{10}$)aryloxy($C_1$-$C_4$)alkyl, ($C_4$-$C_{10}$)heteroaryloxy($C_1$-$C_4$)alkyl, —$R^x$—C(=O)—$R^y$, —$R^x$—O—$R^z$, —$R^x$—O—$R^x$—NR$^3$R$^5$, —$R^x$—NR$^3$R$^5$ or ($C_1$-$C_4$)alkyl-B—(OH)$_2$;
each $R^x$ is independently ($C_1$-$C_4$)alkylenyl;
$R^y$ is ($C_1$-$C_4$)alkyl, hydroxyl, ($C_1$-$C_6$)alkoxy or ($C_6$-$C_{10}$)aryl;
$R^z$ is ($C_1$-$C_4$)alkyl;
$R^3$ is H;
$R^4$ is ($C_1$-$C_4$)alkyl or H; and
$R^5$ is —C(=O)—($C_1$-$C_4$)alkyl, —C(=O)—($C_6$-$C_{10}$)aryl, —SO$_2$—($C_6$-$C_{10}$)aryl, —C(=O)NR$^3$R$^4$ or —C(=O)—NR$^4$($C_6$-$C_{10}$)aryl.

2. The compound according to claim 1, wherein said compound of formula IA has the structure of a compound of formula Ia:

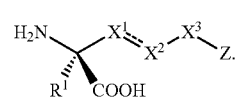

Ia

3. The compound according to claim 1, wherein,
$R^1$ is ethyl, n-propyl, isopropyl, n-butyl, isobutyl, sec-butyl, tert-butyl, hydroxy($C_1$-$C_3$)alkyl, ($C_3$-$C_4$)alkenyl, ($C_6$)aryl($C_1$-$C_4$)alkyl, ($C_5$)heteroaryl($C_1$)alkyl, ($C_4$-$C_5$)heterocycloalkyl($C_3$)alkyl, ($C_6$)aryloxy($C_2$-$C_3$)alkyl, ($C_6$)heteroaryloxy($C_3$)alkyl, —$R^x$—C(=O)—$R^y$, —$R^x$—O—$R^z$, —$R^x$—O—$R^x$—NR$^3$R$^5$, —$R^x$—NR$^3$R$^5$ or ($C_4$)alkyl-B—(OH)$_2$;
each $R^x$ is independently ($C_1$-$C_4$)alkylenyl;
$R^y$ is ($C_2$)alkyl, hydroxyl, ($C_1$)alkoxy or ($C_6$)aryl;
$R^z$ is ($C_2$)alkyl;
$R^3$ is H;
$R^4$ is ($C_1$)alkyl or H; and
$R^5$ is —C(=O)—($C_1$)alkyl, —C(=O)—($C_6$)aryl, —SO$_2$—($C_6$)aryl, —C(=O)NR$^3$R$^4$ or —C(=O)—NR$_4$($C_6$)aryl.

4. The compound according to claim 3, wherein $R^1$ is ethyl.
5. The compound according to claim 3, wherein $R^1$ is n-butyl, isobutyl, sec-butyl or tert-butyl.
6. The compound according to claim 3, wherein $R^1$ is ($C_3$)alkenyl.
7. The compound according to claim 3, wherein $R^1$ is ($C_4$)alkenyl.
8. The compound according to claim 3, wherein $R^1$ is hydroxy($C_1$)alkyl.
9. The compound according to claim 3, wherein $R^1$ is hydroxy($C_3$)alkyl.
10. The compound according to claim 3, wherein $R_1$ is ($C_6$)aryl($C_1$)alkyl.
11. The compound according to claim 3, wherein $R_1$ is ($C_6$)aryl($C_4$)alkyl.
12. The compound according to claim 3, wherein $R^1$ is ($C_4$)heterocycloalkyl($C_3$)alkyl.
13. The compound according to claim 3, wherein $R^1$ is ($C_5$)heterocycloalkyl($C_3$)alkyl.
14. The compound according to claim 3, wherein $R^1$ is ($C_6$)aryloxy($C_2$)alkyl.
15. The compound according to claim 3, wherein $R^1$ is ($C_6$)aryloxy($C_3$)alkyl.
16. The compound according to claim 3, wherein each $R^x$ is independently ($C_1$)alkylenyl.

17. The compound according to claim 3, wherein each $R^x$ is independently $(C_2)$alkylenyl.

18. The compound according to claim 3, wherein each $R^x$ is independently $(C_4)$alkylenyl.

19. The compound according to claim 1, wherein said compound is selected from the group consisting of 2-Amino-2-benzyl-6-boronohexanoic acid;
2-Allyl-2-amino-6-boronohexanoic acid;
2-Amino-2-(4-boronobutyl)succinic acid;
2-Amino-6-(borono-2-(3-phenoxypropyl)hexanoic acid;
2-Amino-6-borono-2-(4-phenylbutyl)hexanoic acid;
2-Amino-6-borono-2-(3-(4-chlorophenoxy)propyl) hexanoic acid;
2-Amino-6-borono-2-(3-(4-methoxyphenoxy)propyl) hexanoic acid;
2-Amino-6-borono-2-(3-(4-fluorophenoxy)propyl) hexanoic acid;
2-Amino-6-borono-2-(3-(4-nitrophenoxy)propyl) hexanoic acid;
2-Amino-2-(3-(benzo[d][1,3]dioxol-5-yloxy)propyl)-6-boronohexanoic acid;
2-Amino-6-borono-2-(3-(4-(trifluoromethyl)phenoxy) propyl)hexanoic acid;
2-Amino-6-borono-2-(3-(3-methoxyphenoxy)propyl) hexanoic acid;
2-Amino-6-borono-2-(3-(3-phenoxyphenoxy)propyl) hexanoic acid;
2-Amino-6-borono-2-(3-(3-isopropylphenoxy)propyl) hexanoic acid;
2-Amino-2-(3-(biphenyl-4-yloxy)propyl)-6-boronohexanoic acid;
2-Amino-2-(3-(biphenyl-3-yloxy)propyl)-6-boronohexanoic acid;
2-Amino-6-borono-2-(3-(3-(trifluoromethyl)phenoxy) propyl)hexanoic acid;
2-Amino-6-borono-2-(3-(4-(trifluoromethylthio)phenoxy)propyl)hexanoic acid;
2-Amino-6-borono-2-(3-(2,6-difluorophenoxy)propyl) hexanoic acid;
2-Amino-6-borono-2-(3-(o-tolyloxy)propyl)hexanoic acid;
2-Amino-6-borono-2-(3-(p-tolyloxy)propyl)hexanoic acid;
2-Amino-2-(3-(4-aminophenoxypropyl)-6-boronohexanoic acid;
2-Amino-6-(borono-2-(pyridin-3-ylmethyl)hexanoic acid;
2-Amino-2-(benzyloxyethyl)-6-boronohexanoic acid;
2-Amino-6-borono-2-(2-methoxyethyl)hexanoic acid;
2-Amino-6-borono-2-(2-(p-tolyoxy)ethyl)hexanoic acid;
2-Amino-6-borono-2-(2-(3-chlorophenoxy)ethyl) hexanoic acid;
2-Amino-6-borono-2-(2-(3-methoxyphenoxy)ethyl) hexanoic acid;
2-Amino-6-borono-2-(2-(3-nitrophenoxy)ethyl)hexanoic acid;
2-Amino-6-borono-2-(2-(3-(morpholinosulfonyl)phenoxy)ethyl)hexanoic acid;
2-Amino-2-(2-(3-aminophenoxy)ethyl)-6-boronohexanoic acid;
2-Amino-6-borono-2-(3-hydroxypropyl)hexanoic acid;
2-Amino-6-borono-2-(4-boronobutyl)hexanoic acid;
2-Amino-2-(4-boronobutyl)hex-4-enoic acid;
2-Amino-6-borono-2-(2-(2-methoxyethoxy)ethyl) hexanoic acid;
2-Amino-6-borono-2-isobutylhexanoic acid;
2-Amino-6-borono-2-(hydroxymethyl)hexanoic acid;
(R)-2-Amino-6-borono-2-(hydroxymethyl)hexanoic acid;
(S)-2-Amino-6-borono-2-(hydroxymethyl)hexanoic acid;
2-Amino-2-(2-(benzyloxy)-2-oxoethyl)-6-boronohexanoic acid;
2-Amino-6-borono-2-(2-methoxy-2-oxoethyl)hexanoic acid;
2-Amino-6-borono-2-(cyanomethyl)hexanoic acid;
2-Amino-6-borono-2-(2-oxobutyl)hexanoic acid;
2-Amino-6-borono-2-(2-oxo-2-phenylethyl)hexanoic acid;
2-Amino-2-(2-(2-aminoethoxy)ethyl)-6-boronohexanoic acid;
2-Amino-6-borono-2-(3-(piperidin-4-yl)propyl)hexanoic acid;
2-Amino-6-borono-2-(3-(piperazine-1-yl)propylhexanoic acid;
2,6-Diamino-2-(4-boronobutyl)hexanoic acid;
2-Amino-6-borono-2-(2-(2-(4-cyanobenzamid)ethoxy) ethyl)hexanoic acid;
2-(2-(2-Acetamidoethoxy)ethyl)-2-amino-6-boronohexanoic acid;
2-Amino-6-borono-2-(2-(2-(3-(3-methoxyphenyl)ureido) ethoxy)ethyl)hexanoic acid;
2-(3-(1-Acetylpiperidin-4-yl)propyl)-2-amino-6-boronohexanoic acid;
2-(3-(4-Acetylpiperazin-1-yl)propyl)-2-amino-6-boronohexanoic acid;
2-Amino-6-borono-2-(3-(4-(4-cyanobenzoyl)piperazine-1-yl)propyl)hexanoic acid;
2-Amino-6-borono-2-(3-(4-(3-methoxyphenylcarbamoyl)piperazin-1-yl)propyl)hexanoic acid;
2-Amino-6-borono-2-(4-(4-methylphenylsulfonamido) butyl)hexanoic acid;
2-Amino-6-borono-2-(4-(3,5-difluorobenzamido)butyl) hexanoic acid;
6-Acetamido-2-amino-2-(4-boronobutyl)hexanoic acid;
2-amino-6-borono-2-(4-(3-(3-methoxyphenyl)ureido)butyl)hexanoic acid; and
pharmaceutically acceptable salts thereof.

20. The compound according to claim 19, wherein said pharmaceutically acceptable salts comprise at least one hydrochloric acid and trifluoroacetic acid addition salt of said compound.

21. A composition, comprising at least one compound of claim 1 or a pharmaceutically acceptable salt thereof; and a pharmaceutically-acceptable carrier.

22. A method of inhibiting arginase in a mammal, comprising administering to said mammal an effective amount of a compound of claim 1 or a pharmaceutically acceptable salt thereof.

* * * * *